United States Patent [19]

Stevens et al.

[11] Patent Number: 4,858,614

[45] Date of Patent: Aug. 22, 1989

[54] METHODS OF AND APPARATUS FOR POSITIONING AND AIMING AN ULTRASONIC PROBE

[76] Inventors: Jerry D. Stevens; Donald R. Steele; Donald A. Gorney, Jr., all c/o Lawrence Medical Systems, 1100 Avenida Acaso, Camarillo, Calif. 93010

[21] Appl. No.: 188,356

[22] Filed: Apr. 29, 1986

[51] Int. Cl.⁴ .............................................. A61B 8/00
[52] U.S. Cl. ............................................... 128/661.07
[58] Field of Search ....................... 128/661.08–661.10, 128/662.09; 73/861.25

[56] References Cited

U.S. PATENT DOCUMENTS

| | | | |
|---|---|---|---|
| 3,561,430 | 2/1971 | Filler, Jr. ........................ | 128/661.07 |
| 4,416,286 | 11/1983 | Iinuma et al. ................... | 128/661.09 |
| 4,509,526 | 4/1985 | Barnes et al. .................... | 128/661.1 |
| 4,796,634 | 1/1989 | Huntsman et al. .............. | 128/662.01 |

OTHER PUBLICATIONS

Baker, D. W. et al., "Pulsed Ultrasonic Doppler Blood-Flow Sensing", IEEE Trans. on Sonics & Ultrasonics, vol. SU-17, No. 3, Jul. 1970, pp. 170–184.

Doriot, P. A. et al., "Quantitative Analysis of Flow Conditions in Simulated Vessels and Large Human Arteries and Veins by Means of Ultrasound", Conf. Proc. of the 2D. Europ. Congress on UTS in Medicine, Munich Germany, (May 12–16, 1975) pp. 160–168.

Primary Examiner—Francis Jaworski
Attorney, Agent, or Firm—Hughes & Multer

[57] ABSTRACT

A method of aiming an ultrasonic transducer at the center of a blood vessel such as a descending aorta. Automatic gain control is employed to amplify the transducer output signal to a constant level, and the transducer is manipulated until the gain in the amplifier circuitry reaches a minimum. The transducer output signal is used in calculating the cardiac output of the patient and/or his or her cardiac index and/or systemic vascular resistance.

30 Claims, 32 Drawing Sheets

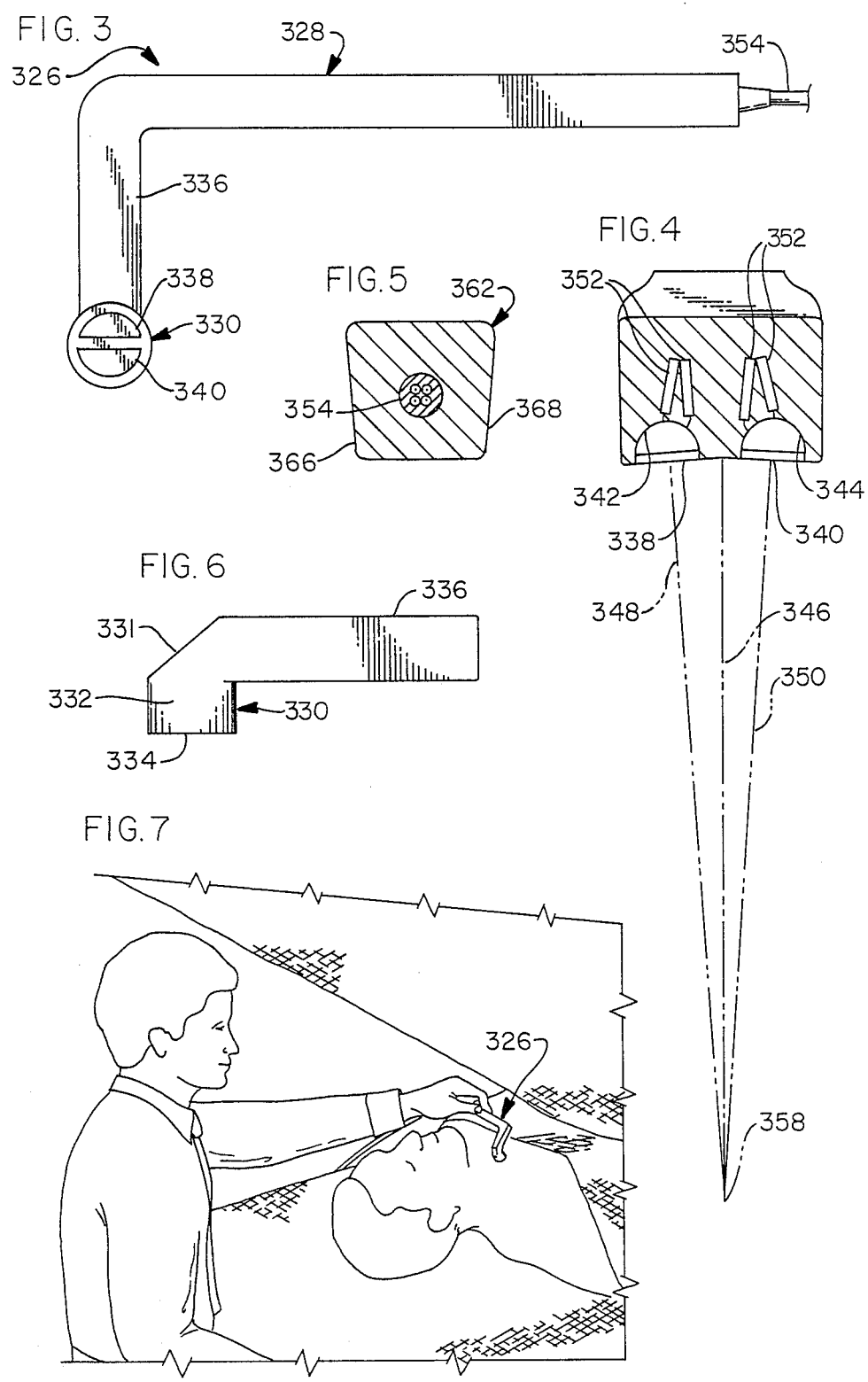

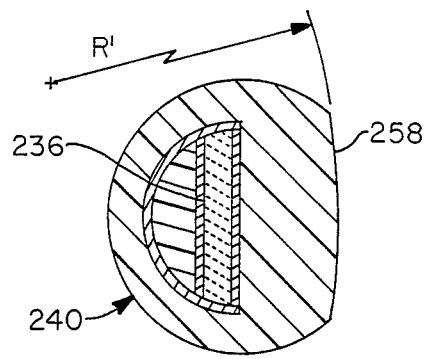
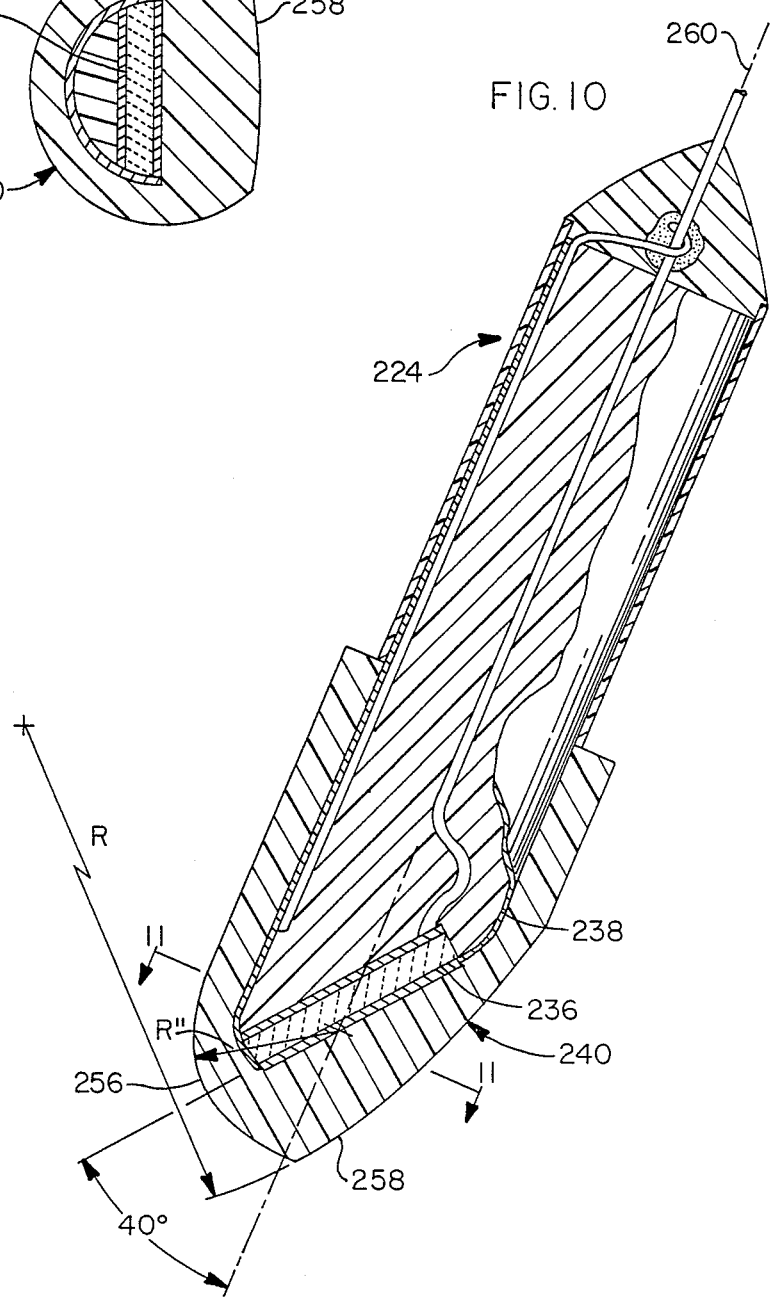

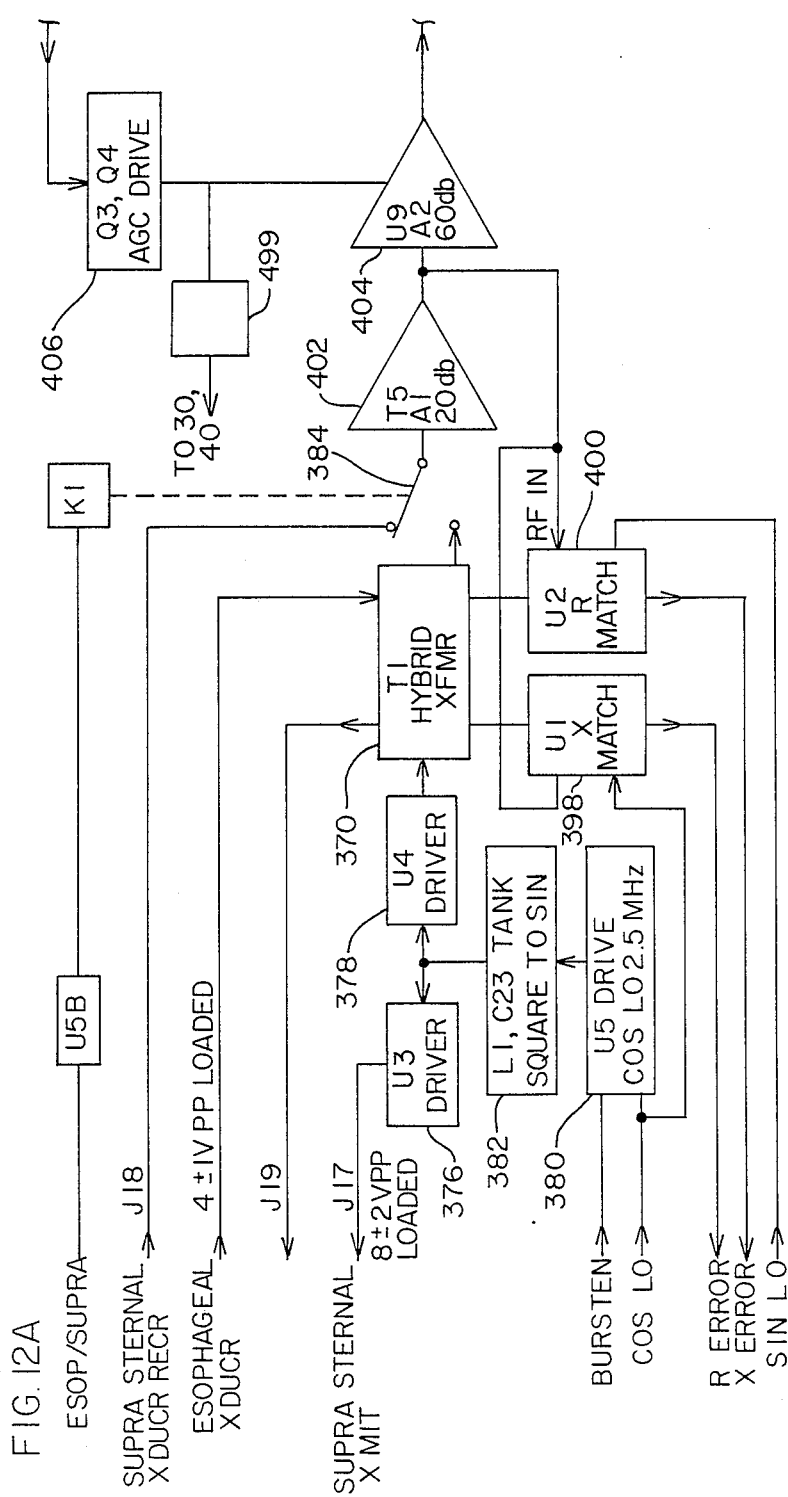

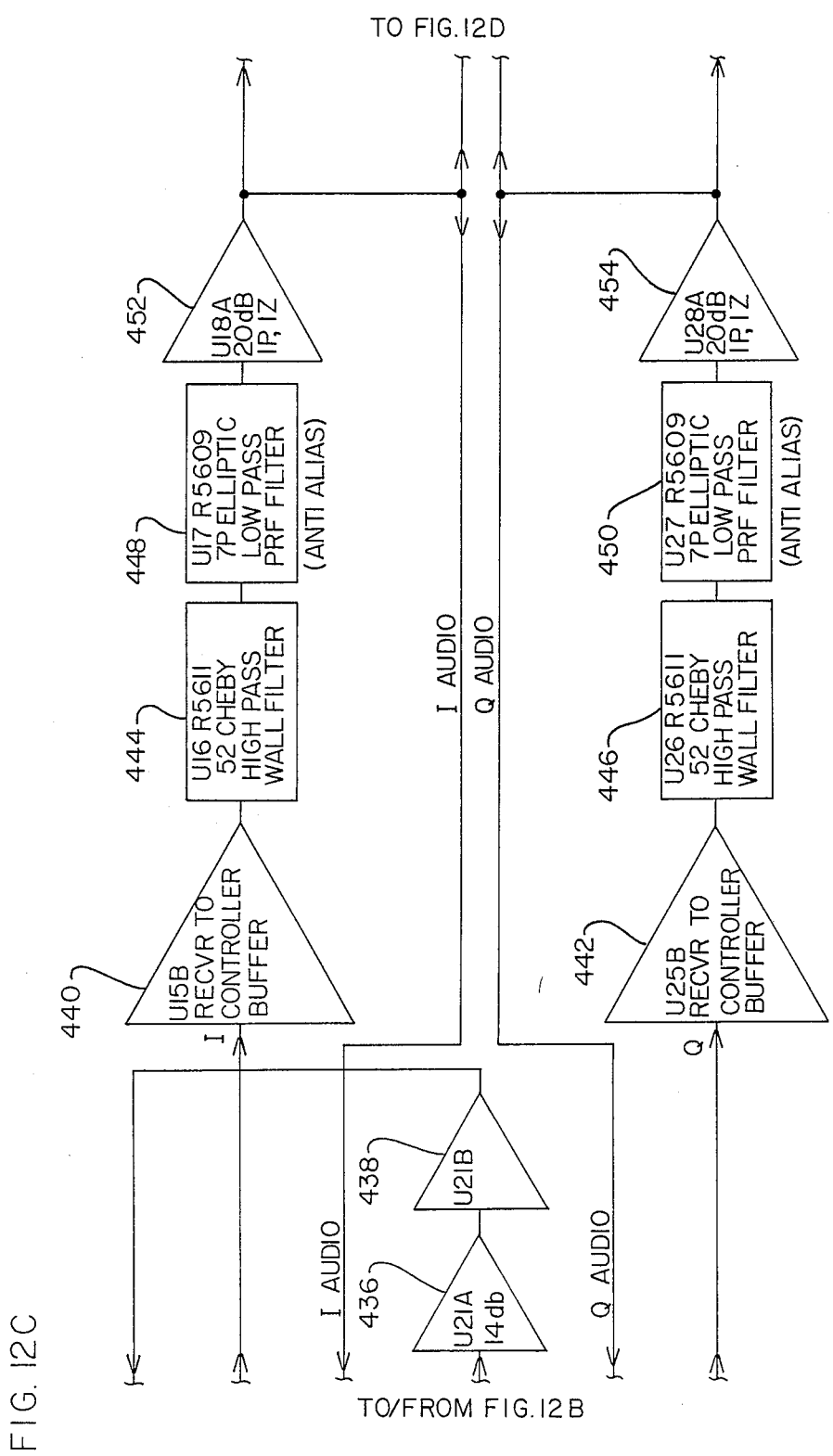

METHODS OF AND APPARATUS FOR POSITIONING AND AIMING AN ULTRASONIC PROBE

RELATION TO OTHER PATENT DOCUMENTS

The following patent documents are hereby incorporated into this specification by reference:

U.S. patent No. 4,509,526 issued 9 Apr. 1985 to Barnes et al. for METHOD AND SYSTEM FOR NON-INVASIVE ULTRASOUND DOPPLER CARDIAC OUTPUT MEASUREMENTS, and allowed U.S. patent application No. 763,992 filed 9 Aug. 1985 by Huntsman et al. for METHODS AND APPARATUS FOR MONITORING CARDIAC OUTPUT (now U.S. patent No. 4796,634 issued 10 January 1989)

TECHNICAL FIELD OF THE INVENTION

The present invention relates to the provision of novel, improved methods of an apparatus for positioning esophageal probes.

BACKGROUND OF THE INVENTION

It is not uncommon for undetected bleeding to occur during surgical procedures because of an unintentionally severed vein or artery. The ensuing loss of blood can result in serious deterioration in the patient's condition, or even in death, if it is not promptly stemmed.

Blood pressure and pulse rate are monitored by the anethesiologist during a surgical procedure, and these parameters provide valuable information on the patient's condition. However, because systemic vascular resistance can increase dramatically during episodes of blood loss such as those just described, it may be as long as four or five minutes after serious bleeding develops or a blood vessel is severed before an appreciable decrease in pulse rate or blood pressure occurs. Currently, serious undetected losses of blood can occur in periods of this magnitude because as much as 35 percent of a patient's blood may be lost before there is a noticeable decrease in blood pressure. By then, however, the patient may be going into shock or suffering other complications attributable to the loss of blood. Although blood pressure and pulse may remain relatively constant for this extended period of time, cardiac output begins to decrease coincidentally with the loss of blood. Hence, by monitoring this parameter, loss of blood can be detected much earlier than would otherwise be the case. This permits the surgical team to take prompt remedial action, hopefully forestalling the deterioration in the patient's condition that might have occurred had the loss of blood gone unchecked.

Variations in cardiac output can also be utilized to detect other unwanted changes in the patient's condition such as the onset of ischemia of the heart muscle or an anesthetic reaction, again permitting remedial action to be taken before there is any significant deterioration in the patient's condition.

Thermal dilution is one technique which has heretofore been employed to measure cardiac output. In that technique, a thermal dilution catheter carrying a thermistor on its tip is inserted through an incision into the jugular vein and threaded through that vessel and the right side of the patient's heart into the pulmonary artery. A saline solution is then injected through the catheter into the patient's bloodstream, typically at a temperature of 0° C. This solution mixes with the blood flowing through the pulmonary artery, momentarily reducing the temperature detected by the catheter tip thermistor. Standard thermodynamic equations allow the cardiac output to be determined from this drop in temperature and the volume of saline solution which produced the temperature drop.

The thermal dilution technique of measuring cardiac output has the disadvantage that it is highly invasive and therefore potentially capable of damaging the anatomical structures through which the catheter is threaded. In fact, in a small percentage of cases (one to two percent), serious complications result from employment of the thermal dilution technique.

Also, the mere presence of the catheter in the pulmonary artery may result in localized clotting of the blood flowing through that vessel. This can obstruct the orifice through which the saline solution is discharged or produce an insulating layer around the thermistor. In both cases, the results will be highly inaccurate.

Finally, the thermal dilution technique is time consuming as it may take as long as 30 minutes to place the catheter; and only a limited number of measurements per hour of cardiac output can be made. Changes in a patient's condition requiring prompt remedial action may therefore not be detectable by the thermal dilution technique.

Because of the disadvantages discussed above, the thermal dilution technique for measuring cardiac output is generally employed only if the patient is undergoing cardiac surgery or is sufficiently ill that surgery poses a risk of cardiac failure.

The Fick method is another technique for measuring cardiac output that has heretofore been employed to some extent. In it, blood samples are taken at two different points in the circulatory system, one just downstream of the patient's aorta and the other in the pulmonary artery. The concentrations of oxygen in these arteries are compared, and the resulting value is combined with the amount of carbon dioxide being expelled by the patient to provide a measurement of cardiac output.

The Fick technique has the disadvantage that the measurements are complex and can easily require a day of analysis before cardiac output can be ascertained. This makes the Fick technique useless in the operating theatre where up-to-the-minute information is required to keep the patient in a stable condition.

Of the techniques for measuring cardiac output discussed above, thermal dilution is the most widely employed.

The drawbacks and disadvantages of the above-discusssed techniques for measuring cardiac output are eliminated in the method of measuring cardiac output described in above-cited Patent No. 4,509,526.

In the method of measuring a patient's cardiac output disclosed in the '526 patent, the diameter of the patient's ascending aorta is determined by a pulsed-echo transducer placed on his or her chest, and the systolic velocity of the blood flowing through that artery is determined by insonification of the aorta with an ultrasonic suprasternal notch probe. This second, also external probe makes available Doppler or frequency-shifted electromagnetic signals which are analyzed and converted from the time domain into discrete frequency components by digital fast Fourier transform. The Doppler shifted frequency components of the return signal are converted to velocities, and the latter are employed to calculate a systolic velocity integral.

Multiplying the systolic velocity integral by the cross-sectional aortic area yields beat-by-beat cardiac stroke volumes of the patient; summing the stroke volumes over a predetermined number of consecutive beats and then dividing by the time spanning the predetermined number of beats (in other words, multiplying by the heart rate) yields the patient's cardiac output.

The patented cardiac monitoring apparatus facilitates direct operator interaction with the apparatus over the course of the measurement protocol via a touch sensitive visual display which, inter alia: instructs the operator at each step of the sequence and responds to the election of operator options with failsafe features that guard against the entry of invalid data and otherwise minimize operator error. The operator may interact without extensive training, and the system provides the benefits of microprocessor control including fast data processing without elaborate hardware or software.

Within operational limits, the patented cardiac monitoring system will insist upon the entry of required data, will limit the entry of certain data to values within statistically anticipated ranges, and will assist the operator in optimizing the measurement of variable parameters.

The method for measuring cardiac output which is practical with the apparatus disclosed in the '526 patent is significantly superior to any previously available techniques for providing this vital information. The patented technique for determining cardiac output is noninvasive and therefore does not subject the patient to the risk of infection or anatomical damage or require surgery as is the case in those cardiac output measuring techniques employing a catheter. And the patented method permits cardiac output to be monitored on a continuous, up-to-the present-moment basis. Nevertheless, the patented technique does have its disadvantages. The equipment is expensive and heavy, and extensive operator training is required.

Pending application No. 763,992 discloses a technique for measuring cardiac output and related parameters which eliminates the drawbacks of the approach disclosed in the '526 patent. The equipment utilized in carrying out the method is simpler; less expensive; and easier to operate, significantly reducing the amount of operator training that is required to use it.

In the novel method and apparatus for monitoring cardiac output to which the '992 application is devoted, an ultrasonic esophageal probe is substituted for the suprasternal notch probe used to monitor systolic velocity in the system disclosed in the '526 patent. This probe monitors the blood flowing through the patient's descending aorta rather than his ascending aorta. This velocity is scaled to the velocity of the blood flowing in the patient's ascending aorta, and the result is combined with a number representing the area of the patient's ascending aorta to produce a cardiac output value.

This substitution of an ultrasonic esophageal probe for the suprasternal notch probe employed in the patented equipment is important when the system is used during surgery. The preferred type of esophageal probe does not interfere with the operating field as does a suprasternal notch probe of the type disclosed in the '526 patent. In addition, unless esophageal surgery is involved, the probe is out of the sterile field, which is an obvious advantage. Furthermore, this probe replaces the esophageal stethoscope which would be employed in any event so that, in effect, another measurement of the patient's condition can be monitored without further invasion of the patient's body.

The blood flowing through a patient's descending aorta is only about 70 percent of that flowing through his ascending aorta, the remainder having been distributed to the patient's subclavian and carotid arteries before the descending aorta is reached. Consequently, in the cardiac output measuring apparatus disclosed in the '992 application, provision is made for scaling the systolic velocity measured with the esophageal probe by an appropriate conversion factor to the velocity which would have been obtained if the flow in the patient's ascending aorta were instead monitored.

The proportioning of the blood pumped by a patient's heart between the descending aorta and those other blood vessels discussed above will vary from patient-to-patient. Consequently, the suprasternal notch probe technique of measuring systolic velocity disclosed in the '526 patent is preferably used to determine an accurate conversion factor for each patient.

The technique for providing the aortic area value that is disclosed in the '992 application is also completely different from the patented technique. In the latter, aortic diameter is measured by insonification of the patient's ascending aorta and converted to aortic area. The approach described in the '992 application instead employs a predictively determined value of aortic diameter for determining cardiac output. This has the advantage that it makes the cardiac monitoring equipment much simpler to use, lighter, and less expensive than that disclosed in the '526 patent.

After the apparatus disclosed in the '992 application was put into widespread clinical use, it was found that the aiming of the esophageal probe by the provided for techniques sometimes led to less than optimal results. This is because the aiming technique in question made use of a signal related to the peak velocity of the blood flowing through the patient's descending aorta, and it was proved that the peak velocity may occur in a region well removed from the centerline of the descending aorta while a transducer aimed at the aortic centerline produced a signal which, when converted to cardiac output, most accurately reflected the patient's actual cardiac output.

SUMMARY OF THE INVENTION

In the cardiac monitoring apparatus disclosed in the '992 application, the output from the ultrasonic transducer of the esophageal probe is amplified to a constant level to facilitate the calculation of cardiac output. We have now found that: (1) the level of the gain employed in that amplifier circuit to keep its output constant accurately reflects the peak systolic velocity of the blood flowing through a vessel such as a human's descending aorta, (2) the gain in the amplifier section of the signal processing circuitry is the lowest when the transducer of the esophageal probe is aimed directly at the center of the decending aorta, and (3) the gain level rapidly increases if the transducer is aimed only a few degrees °to either side of the aortic centerline.

We have accordingly invented, and disclosed herein, a novel method of aiming an esophageal probe (or other ultrasonic transducer) at a vessel with the flow characteristics just described in which advantage is taken of the peak flow velocity/gain level relationship to aim an ultrasonic transducer at the center of a vessel being monitored. A signal indicative of gain level can be employed to drive visual and/or audio outputs which can be monitored by the operator. He or she can, accordingly, simply monitor such an output unitl it: (1) reaches a peak, indicating that optimal aiming has been accomplished; or (2) at least exceeds a given reference level indicative of an acceptable level of aiming (this presupposes that the gain signal has first been inverted or subtracted from a reference signal so that the signal driving the display will increase in magnitude as the transducer is more accurately aimed toward the selected target). Subsequent changes in gain also provide valuable information—e.g., that the probe has shifted and needs to be repositioned.

Our novel technique for aiming an ultrasonic transducer also:

1. allows faster aiming and positioning of the transducer;
2. produces more accurate results;
3. allows more room for accidental shifting of the transducer during use since it starts out pointed at the center of the patient's aorta;
4. lessens the frequency of offline conditions and consequent necessity for reaiming;
5. assures that the apparatus in which the transducer is incorporated is operating in a range which is optimized for the existent conditions by minimizing the distance to the target and selecting the path with the least signal loss;
6. reduces the possibility of interference from other sources; and
7. assures that ultrasonic transducer is pointed at the appropriate target.

OBJECTS OF THE INVENTION

From the foregoing, it will be apparent to the reader that one primary and important object of the present invention resides in the provision of novel, improved methods of and apparatus for monitoring such hemodynamic factors as cardiac output, cardiac index, and systemic vascular resistance.

A related, also important and primary object of our invention reside in the provision of cardiac monitoring methods and apparatus which differ from those disclosed in copending application No. 763,992 (now U.S. Patent No. 4796,634) in that a superior technique for aiming an ultrasonic esophageal transducer employed to monitor systolic flow velocity in a patient's aorta is made available.

Still other important objects of our invention will be apparent to the reader from the foregoing and the appended claims and as the ensuing detailed description and discussion proceeds in conjunction with the accompanying drawings.

BRIEF DESCRIPTION OF THE DRAWINGS

In the drawings:

FIG. 3 is a bottom view of the probe;

FIG. 4 is a section through the probe taken substantially along line 4—4 of FIG. 2;

FIG. 5 is a section through the probe taken substantially along line 5—5 of FIG. 2;

FIG. 6 is an end view of the probe;

FIG. 7 is a view of an ultrasonic probe as illustrated in FIG. 2 positioned in a supine patient's suprasternal notch by an operator standing behind his head;

FIG. 10 is a partial section through the esophageal probe illustrated in FIG. 8;

FIG. 11 is a section through FIG. 10;

DETAILED DESCRIPTION OF THE INVENTION

Figure 1:
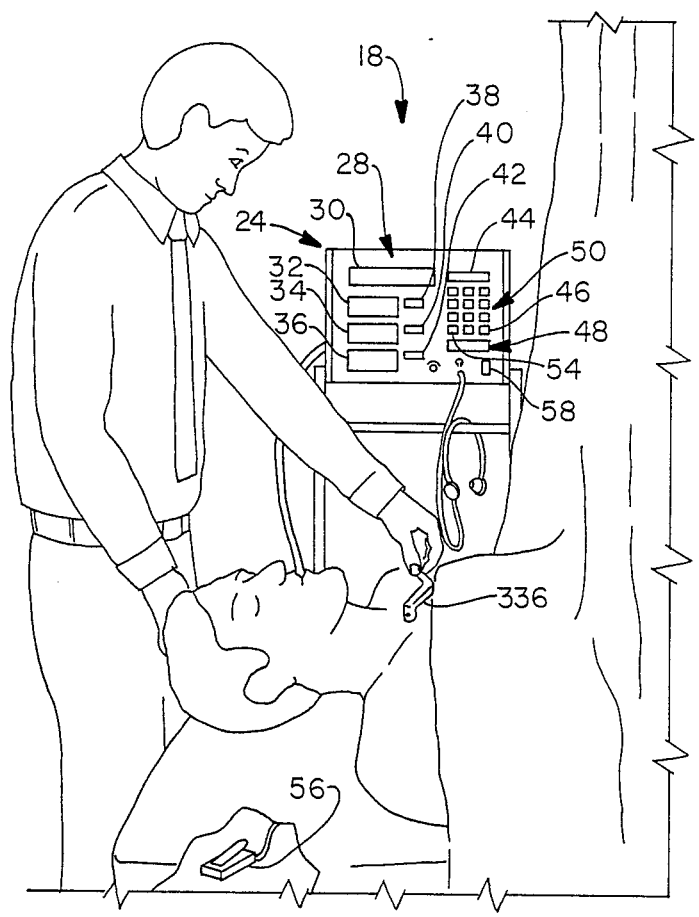
FIG. 1 is a pictorial view of apparatus for monitoring the cardiac output of a human patient and related parameters; this apparatus is constructed in accord with, and embodies, the principles of our invention.

As discussed above, the novel cardiac monitoring apparatus disclosed herein is designed to: (1) provide an ultrasonic probe-generated signal indicative of the systolic velocity of the blood flowing through the patient's ascending aorta; (2) convert or scale that signal to one representative of the velocity of the body flowing through the patient's ascending aorta; (3) compute the patient's cardiac output from the scaled up systolic velocity signal and the area of the patient's ascending aorta; and (4) facilitate the aiming of the ultrasonic probe toward the center of the patient's descending aorta so that the computed value will as accurately as possible reflect the patient's actual cardiac output.

In the interest of maximizing efficiency and reliability of results, software is preferably employed to establish a plurality of signal sampling rates based upon corresponding ranges of statistically anticipated systolic velocities for the patient under examination. High and low threshold values are selected for these separate velocity ranges; systolic velocity is monitored to determine its value within a given one of the ranges as measured with reference to the selected threshold values; and the signal sampling rate is adjusted to that one of the sampling rates corresponding to the systolic velocity.

Cardiac monitoring apparatus employing the principles of the present invention initially processes data at the first sampling rate while monitoring the velocity signal. Upon the occurrence of systolic velocities in excess of the high threshold value for the first range, the system automatically adjusts the sampling rate to the second rate for further processing. Monitoring the velocities continues, then with reference to both a high and low threshold value within the second range. Systolic velocities lower than the low threshold cause a downward adjustment to the first sampling rate, while velocities in excess of the high threshold for the second range adjust the sampling rate to the third range. Should the third rate be selected, and subsequent monitoring reveal systolic velocities lower than a low threshold for that range, an adjustment in the sampling rate to the second rate is made. In this manner, processing of data is correlated with the appropriate velocity range, enhancing processing capabilities while simplifying system hardware and software.

An audible indication of systolic velocity is also made available to the operator by an audio signal with a frequency directly proportional to velocity.

A conventional frequency spectrum analyzer converts the analog time domain velocity signal appearing at the esophageal probe into its digital frequency domain counterpart at a sampling rate determined by the criteria discussed above and, in more detail, in Patent No. 4,526,509. A spectrum analysis is typically completed once every 2.5 to 10 milliseconds, depending upon the sampling rate dictated by the systolic flow velocity of the blood being monitored.

There is a peak frequency in each sampling period. The peak frequencies which are associated with each cardiac cycle (or heartbeat) collectively constitute a velocity profile signal which is accurately indicative of the actual systolic velocity of the patient's aortic blood flow. The velocity profile signal is integrated over the time of the cardiac cycle, producing a systolic flow velocity integral. Stroke volume is computed from the integrated profile and the patient's predictively determined aortic diameter, and his cardiac output is calculated by summing n stroke volumes and dividing the sum by the time span of the n cardiac cycles for which stroke volumes were determined.

We pointed out above that a systolic flow velocity measured by insonification of the patient's ascending aorta with an ultrasonic suprasternal notch probe is employed to generate a scaling factor in our novel cardiac monitoring apparatus. The frequency-shifted signal made available by the suprasternal notch probe is processed in the same manner as the signal generated by the also previously discussed ultrasonic esophageal probe and for the same reasons.

Both stroke volume and cardiac output are measurements that can be employed to advantage in determining a patient's bodily condition. Related, and perhaps equally useful, indicia of a patient's condition are stroke index and cardiac index. As discussed above, cardiac index is cardiac output normalized across the general population by dividing that measure by the patient's body surface area so that one can make a determination of a patient's condition simply by comparing the patient's cardiac index to a standard.

Stroke index is useful for the same reasons and is determined in an analagous manner; viz., by dividing stroke volume by the patient's body surface area.

Our novel cardiac monitoring apparatus is designed to also make the calculations necessary to determine stroke index and cardiac index.

Another calculation which that apparatus is designed to make is systemic vascular resistance. We pointed out earlier herein that systemic vascular resistance (blood pressure divided by cardiac output) is particularly useful in developing a drug regime for a patient requiring medical intervention.

Referring now to the drawing, FIG. 1 depicts cardiac monitoring apparatus 18 embodying and constructed in accord with the principles of the present invention. Among the major components of this apparatus is an ultrasonic esopageal probe 220 which is employed to measure the systolic velocity of the blood flowing through a patient's descending aorta. Cardiac monitoring apparatus 18 also includes a suprasternal notch probe 326 which is employed on a one-time or infrequent basis to provide a scale factor for converting the velocity measured by probe 220 to the velocity of the blood flowing through the patient's ascending aorta. Other major components of the cardiac output monitoring apparatus are: (1) a Zilog Z8000 series microprocessor (not shown) for performing the just-described conversion and for computing cardiac output and the other parameters discussed above from the calculated velocity and the area of the patient's ascending aorta, (2) a transmitter/receiver system for driving the ultrasound transducer of esophageal probe 220 and for converting frequency-shifted ultrasonic energy reflected from the blood flowing through the patient's descending aorta to the transducer to a usable electrical signal of constant amplitude, and (3) circuitry for interfacing the signal processing circuitry with the microprocessor.

The transmitter/receiver circuits, the computer interface, and the microprocessor are housed in a cabinet 24 which also includes a touch-sensitive monitor 28 with a two-line, 20 character per line display 30 labeled ADVISORY; dual-mode LED displays 32, 34, and 36 for: cardiac output and heart rate, cardiac index and signal level, and SVR (systemic vascular resistance) ejection time.

Heart rate, signal level, and ejection time are displayed during the positioning of ultrasonic esophageal probe 220 and ultrasonic suprasternal notch probe 326; they assist the operator in optimally orienting the ultrasonic probes. Specifically, the aorta has a different duration of systole or ejection time than other major blood vessels in its vicinity. By observing the EJECTION TIME display, therefore, the operator can ascertain whether the return signal is one reflected from the patient's aorta or from a different blood vessel.

SIGNAL LEVEL is used in positioning the ultrasonic probe. More particularly, as was discussed briefly above and as will be discussed in more detail hereinafter, the gain in the receiver section of the system illustrated in FIG. 12 is automatically adjusted as necessary by the Zilog microprocessor to maintain a constant output level, and the amount of gain is utilized in aiming the ultrasonic esophageal probe, it having been found by us that: (1) the gain in the receiver circuit is a minimum when the ultrasonic transducer of the esophageal probe is aimed at the center of the patient's descending aorta, and (2) this aim provides the most accurate results.

SIGNAL LEVEL, in this respect and in accord with the principles of the present invention, is an inverse of the automatic gain voltage applied to the circuit (see FIG. 12) which is provided in cardiac monitoring apparatus 18 to process the output signal from esophageal probe 220 and convert that signal to a frequency-shifted signal of constant amplitude. Because the gain voltage is at its minimum when the transducer of esophageal probe 220 is aimed at the center of the patient's descending aorta, the operator can accurately aim the probe by rotating it until the number displayed by LED 34 is maximized. Thereafter, SIGNAL LEVEL is displayed in advisory 30 while apparatus 18 is in the monitoring mode. The value displayed in advisory 30 will decrease if the probe shifts. Thus, a shift in the position of the probe of sufficient magnitude to require repositioning can be identified by monitoring advisory 30.

Ejection time can be employed to insure that esophageal probe 220 is aimed at the patient's descending aorta (proper) and not his or her innominate artery (incorrrect). A high ejection time (typically above 400) usually indicates that the probe is aimed at the innominate artery and should be repositioned. Also, if the ejection time is too high, a message "ET HIGH REPOS PROBE" will appear in display 30. A corresponding message will appear if ET is too low.

LED displays 38, 40, and 42 with the legends HEART RATE, SIGNAL LEVEL, and EJECTION TIME and the associated value-indicating LED's 32, 34, and 36 are backlighted when the monitor is operating in the set-up mode just discussed.

Also available on monitor 28 of the cardiac monitoring apparatus are touch-sensitive areas that furnish START OVER, REVISE, and ADVANCE keys 44, 46, and 48 and a keyboard 50 with keys 1 through 0 and a minus key 54, which is employed to enter a negative blood pressure in measuring cardiac index and systemic vascular resistance.

We pointed out above that aortic diameter is one of the factors utilized by cardiac monitoring apparatus 18 in computing cardiac output (and cardiac index and systemic vascular resistance). The aortic diameter of the patient's ascending aorta may be known, and that known value can be entered directly into the programs run by the microprocessor of cardiac monitoring apparatus 18 as will become apparent hereinafter. Alternatively, the age, height, weight, and sex of the patient are determined and his or her aortic diameter predictively determined from these parameters by employing the following, simple and unique, predictive algorithm:

$$AD = C_1 + [C_2 \times AGE] \times [C_3 \times SEX] + [C_4 \times HEIGHT] + [C_5 \times WEIGHT] \quad (1)$$

where:
$C_1$ is in the range of 8.06 to 14.88,
$C_2$ is in the range of 0.055 to 0.077,
AGE is the age of the patient in years,
$C_3$ is in the range of $-2.43$ to $-1.57$,
SEX is 0 if the patient is a male and one if the patient is a female,
$C_4$ is in the range of 0.108 to 0.208,
HEIGHT is the height of the patient in inches,
$C_5$ is in the range of 0.010 to 0.018, and
WEIGHT is the weight of the patient in pounds.

The value of the constants in Equation (1) that we presently prefer to use are:
$C_1$: 11.47
$C_2$: 0.066
$C_3$: $-2.0$
$C_4$: 0.158
$C_5$: 0.014

Referring now to FIGS. 2–7, we pointed out above that suprasternal notch probe 326 is employed in generating a scaling factor. This is used to scale the systolic velocity of the blood flowing through the patient's descending aorta to the systolic velocity of the blood flowing through the ascending aorta. The latter value is needed to compute the patient's cardiac output (or cardiac index or systemic vascular resistance).

Suprasternal notch probe 326 includes a handle 328 and a transducer head 330 integral therewith. Transducer head 330 has a sloping top wall 331 and curved side walls 332, giving the transducer head 330 a generally oval cross-sectional configuration as shown in FIG. 3 and a trapezoidal profile as shown in FIG. 6. The bottom or lower end of the transducer head is essentially flat when viewed from the side; it has a shallow V-configuration when seen from the front (FIG. 5).

In the embodiment of the invention shown in the drawing, the lower end 334 of transducer head 330 extends below the bottom side or surface 336 of probe handle 328. This is an important feature of probe 326 as it furnishes sufficient clearance for the operator to wrap his fingers around the handle 328 of probe 326 when the head of the probe is positioned in the patient's suprasternal notch. This facilitates the tactile positioning and manipulation of the probe within the patient's suprasternal notch.

Flat, D-shaped transducers 338 and 340 are flush-mounted in cavities 342 and 344 in the lower end 334 of transducer head 330 with the transducers canted toward a longitudinal plane 346 extending vertically through the transducer head as is shown in FIG. 4.

The illustrated transducers 338 and 340 are of the conventional piezoelectric crystal type; and these will, accordingly, not be described further herein. They can be cemented in place by an appropriate adhesive, for example.

Referring now specifically to FIG. 4, ultrasonic energy is propagated from transducer 338 along path 348. This energy, doppler-shifted in frequency, is reflected from the patient's aortic structure and the blood flowing through that vessel back to receptor transducer 340 along path 350.

Transducer 338 and 340 are connected to an external energy source (not shown) through leads 352 incorporated in a conventional insulated cable 354. This cable passes through the head 330 and hand 328 of probe 326 (see FIGS. 4 and 5) and, externally of the probe, terminates in a conventional six-prong connector 356.

As shown in FIG. 4, the path 348 of the propagated ultrasonic energy and the path 350 of the reflected, frequency-shifted energy converge in a focal zone 358 which embraces the patient's ascending aorta. In a probe of the character under discussion, this zone should have a focal point which is preferably approximately seven centimeters from the lower end 334 of transducer head 330.

Figure 2:
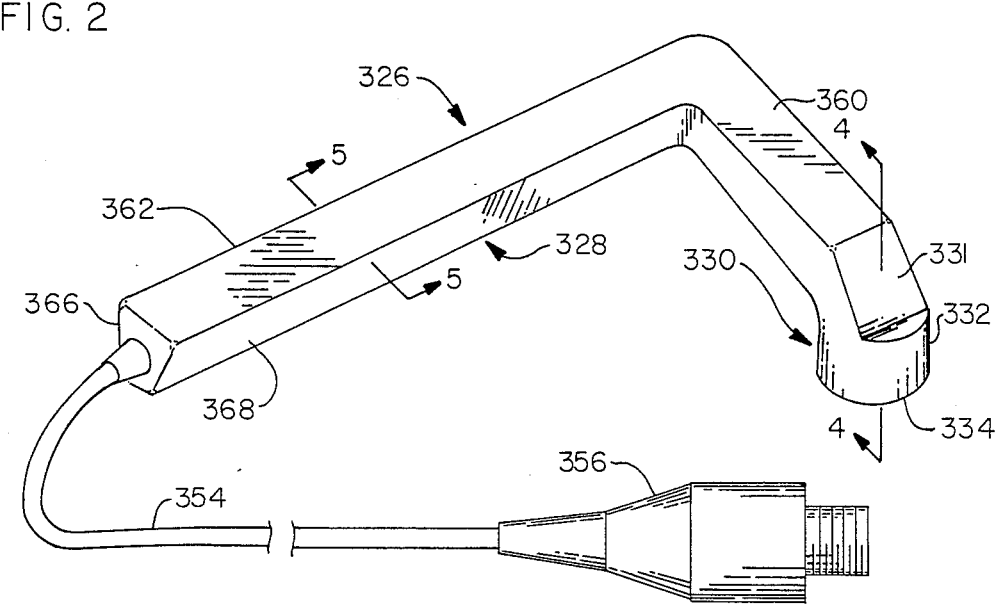
FIG. 2 is a perspective view of an ultrasonic, suprasternal notch probe employed in the apparatus of FIG. 1 to generate a scaling factor.

Referring now primarily to FIGS. 2 and 3, the handle 328 of suprasternal notch probe 326 has a proximate, horizontal portion 360 and, extending at a severe, preferably 90°, angle therefrom, a second, also horizontal, distal portion 362.

As is readily apparent from the drawings, the preferred cross-sectional configuration of handle 328 is one which is approximately rectangular but with the side walls 366 and 368 of the handle's distal portion tapering slightly toward each other from the top toward the bottom of the handle to provide the most secure grasp and optimal operation comfort.

In positioning and aligning the transducer head 330 of ultrasonic probe 326 in a patient's suprasternal notch, the anesthesiologist or other person employing the probe reaches past the head of the patient and introduces the transducer head 330 of the probe within the patient's suprasternal notch (see FIG. 7). This maneuver is typically effected while the operator's attention is directed to the monitor 28 of cardiac monitoring apparatus 18 (as discussed above, the information displayed on the monitor assists him or her in properly positioning the probe). Thereafter, the transducer head may be rotated, shifted rectilinearly, and tilted, again with attention focused on the monitor, until that display shows that the position of the probe has been optimized.

With the operator's fingers and thumb pressed against the distal handle portion 362 of probe 326, a secure grip which optimizes control over these manipulations of the probe with minimal, or even no, view of the patient's suprasternal notch or of transducer head 330 is conveniently available.

The ultrasonic probe 326 illustrated in FIGS. 2-7 and discussed above is configured for use by a right-handed operator positioned behind the head of a supine or reclining patient. An L-shaped, mirror image configuration is provided for left-handed operators. Alternatively, a handle with a T-shaped configuration may be employed so that the probe can be used by either a left-handed or right-handed operator.

Figure 8:
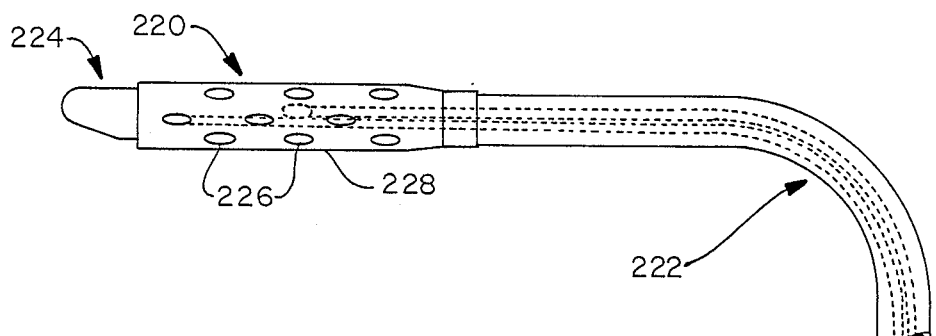
FIG. 8 is a side view of an ultrasonic, single crystal, continuous wave esophageal probe employed in the apparatus of FIG. 1 to measure the systolic velocity of the blood flowing through the descending aorta of the patient.
Figure 9:
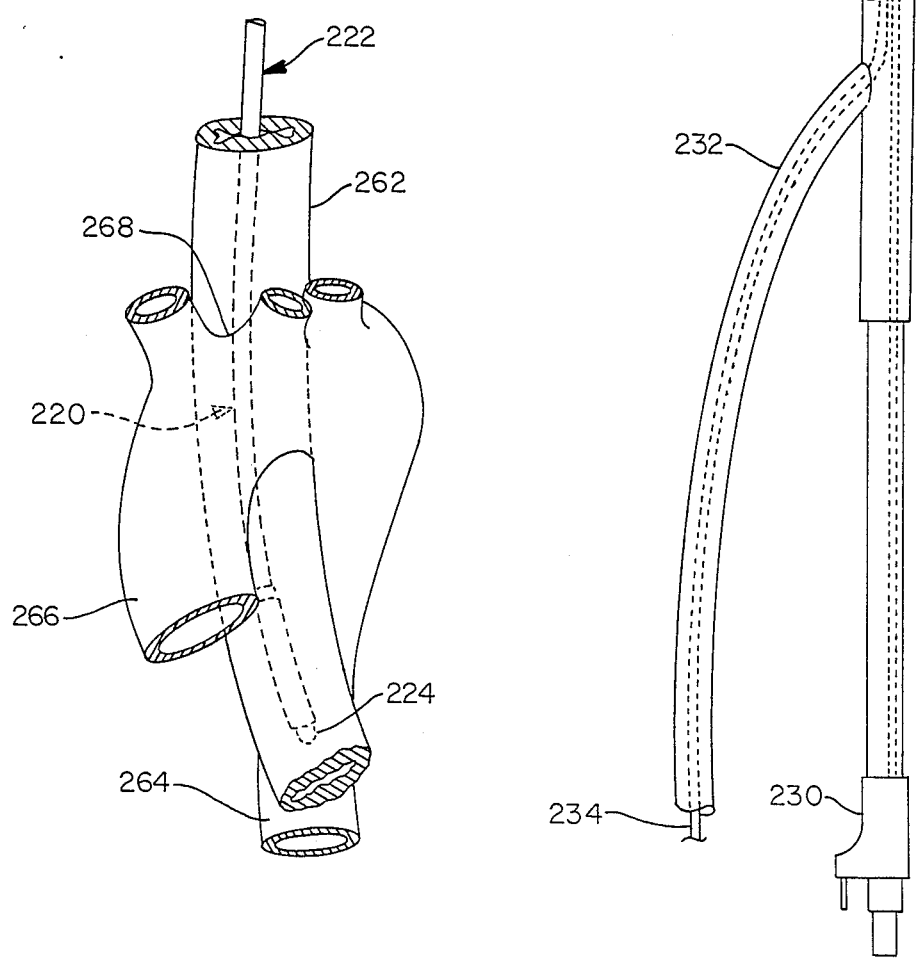
FIG. 9 shows the relation between the esophagus and descending aorta of the patient and the esophageal probe of FIG. 8 in one of the locations it may be caused to assume in that aorta in order to monitor the systolic velocity of the blood flowing therethrough.

Referring now to FIGS. 8-11, the esophageal probe 220 employed to ultrasonically measure the systolic velocity of the blood flowing through the patient's descending aorta consists of an esophageal stethoscope 222 and, mounted on the lower end of the latter, an ultrasonic transducer tip 224 (all references to direction assume that esophageal probe 220 is oriented as shown in FIG. 9).

Esophageal stethoscope 222 is a flexible, hollow tube with acoustical ports 226 in its lower end. An acoustically transparent sleeve 228 is sealed to the tube around ports 226 to keep mucous and other substances in the esophagus from clogging the acoustical ports.

An acoustical coupling 230 is fitted to the upper end of esophageal stethoscope 222. This is employed to connect the esophageal stethoscope to one of conventional character, allowing the physician or other person employing the stethoscope to listen to the patient's breathing, heart sounds, etc. Acoustical coupling 230 also houses leads from a thermistor (not shown) in the lower end of the esophageal stethoscope. That thermistor may be provided so that the patient's body temperature can be monitored as is sometimes advantageous during surgery.

The esophageal probe 220 shown in FIG. 8 also has a flexible, branching tube 232. This contains leads 234 from its ultrasonic transducer crystal or crystals depending on whether a single or double crystal transducer is employed.

Referring still to FIG. 8, the major components of the esophageal probe's transducer tip 224 also include a transducer such as the illustrated single crystal, disc- or D-shaped piezoelectric transducer 236; a support 238 for the transducer; and a lens 240.

Of importance, in conjunction with of transducer tip 224, is the compound curvature of transducer lens 240. That lens is employed to converge the beam of ultrasonic energy propagated from transducer 236 and to steer that beam at a selected, preferably 45°, angle toward the descending aorta of the patient whose systolic blood velocity is being monitored. The compound curvature of the lens eliminates the air bubble problems that have plagued heretofore proposed esophageal probes by allowing the patient's esophageal wall to collapse tightly around the tip 224 of probe 220. This accoustically couples transducer 236 through the mucous in the esophagus to the esophageal wall. Because the esophagus is in intimate contact with the descending aorta over a significant portion of the latter's length, the result is an entirely acceptable acoustic coupling between the transducer and the descending aorta.

As is best shown in FIGS. 10 and 11, lens 240 has a generally arcuate cross-section and a nose 256 which is similarly configured when viewed in longitudinal section as shown in FIG. 8. That part 258 of the lens which steers the beam of energy emitted from transducer 236 is arcuate in both cross- and longitudinal section.

In the transducer tip 224 illustrated in FIG. 11, piezoelectric crystal 236 is mounted at an angle of 40° with respect to the longitudinal centerline 260 of the tip. The compound curvature of lens 240, because of the refraction of the ultrasonic energy in that lens, causes the beam of ultrasonic energy propagated from transducer 236 to be directed at an angle of 45° relative to the descending aorta of the patient whose systolic blood velocity is being monitored.

The esophageal probe 220 just described is introduced into the patient's mouth, typically after he or she is anesthesized, and (preferably) passed first downwardly and then upwardly through the patient's esophagous until transducer tip 224 is opposite the patient's descending aorta. A thus properly located esophageal probe is illustrated in FIG. 9. In that figure, the patient's esophagus is identified by reference character 262, his or her descending aorta by reference character 264, the ascending aorta of the patient by reference character 266, and his or her aortic arch by reference character 268.

The esophagus collapses tightly around tip 224 of the probe after the probe is inserted. As discussed above, this furnishes the wanted acoustical coupling from transducer crystal 236 through the esophagus 262 of the patient to his descending aorta 264. The contact of the esophageal wall stabilizes the transducer over an extended period of time.

As will be apparent from FIG. 9, esophageal probe 220 can readily be rotated in the patient's esophagus 262 after it has been passed down through the esophagus. This allows transducer 224 to be so directed toward aorta 264 as to provide optimal coupling between the transducer and the descending aorta of the patient.

Typically, transducer 236 will be positioned in the mid to lower thoracic region of the patient. Often, optimal results may be achieved by positioning the transducer opposite the aortic arch of the patient or in the region where the esophagus passes through his or her diaphragm. The latter location is preferred because the esophagus is necked down as it passes through the diaphragm. This further promotes acoustical coupling between the probe and the esophageal wall.

Referring to FIG. 12 of the drawing, the system employed to process the signal outputted from the transducer 236 of esophageal probe 220 is employed, in one important respect, to keep the frequency-shifted return signal from being blanketed by the transmitted signal employed to excite the transducer into an ultrasonic energy emitting mode. One key component in the scheme is a hybrid transformer. That transformer is illustrated in FIGS. 12A and identified by reference character 370. Hybrid transformers and their mode of operation are described in more detail in HYBRID TRANSFORMERS PROVE VERSATILE IN HIGH-FREQUENCY APPLICATIONS, Gross, T. A. O. Gross & Associates, Lincoln, Massachusetts.

Also provided in the system shown in FIG. 12 are a transmitter 372 and a receiver 374 which are respectively employed to excite piezoelectric crystal 236 of probe 220 and to process the reflected, frequency-shifted signal available from that transducer.

As best shown in FIG. 12A, transmitter 372 includes drivers 376, 378, and 380 and an LC tank 382. Driver 380 is continuously driven with a 2.5 MHz square wave signal designated COS LO. The tank circuit 382 converts the square wave pulses to a sinusoidal voltage which is amplified by driver 378 and applied to piezoelectric crystal 236 of esophageal probe 220 to excite that transducer.

As mentioned above, receiver 374 is provided to process the systolic velocity indicative, Doppler-shifted signals detected by transducer 236. It can also be employed to process frequency-shifted signals available from suprasternal notch probe 326.

A two-position switch 384 (see FIG. 12A) allows either a: (1) single crystal esophageal probe, or (2) dual crystal esophageal probe or suprasternal notch probe mode of operation to be selected. In the latter two modes of operation, hybrid transformer 370 is bypassed.

The power of the transmitted signal may be as much as 127 to 130 dbm greater than that of the reflected, frequency-shifted signal simultaneously available at transducer 236 in the continuous wave mode of operation for which the single crystal esophageal probe 220 is designed. Because receiver 374 will typically have a dynamic range of only 60 dbm, the transmitted signal would consequently blanket the wanted return signal absent the employment of hybrid transformer 370 or other scheme to block the transmitted signal from receiver 374.

Feedback is employed to dynamically balance the primary coils (not shown) of hybrid transformer 370. Also, the characteristics of the signal propagated from the transducer are effected by pressure and temperature, and these parameters constantly vary in a patient's body. The feedback continuously compensates for variations in these parameters.

Referring still to FIG. 12A, the active elements of the feedback control utilize phase detectors and are identified by reference characters 398 and 400. The inputs to the phase detectors are signals representing the sums of and differences between the frequency of the signal from transducer 236 and a reference signal. The outputs from these detectors are designated COS LO and SIN LO. If the frequency-shifted signal is in phase with the transmitted signal, the signal designed COS LO will be generated in the detector of active circuit element 400 and used to balance the hybrid transformer primary windings. If the transmitted and frequency-shifted signals are out-of-phase, the SIN LO signal will appear and be used to precision tune the inductance in the primary windings of the hybrid transformer to the transducer 236 of a particular esophageal probe 220.

The frequency-shifted signals reflected from bones or other large anatomical structures are blocked from receiver 374 because the hybrid transformer 370 and associated circuits shown in FIG. 12A discriminates between reflected signals of different frequencies. The reflected signals of interest will typically have a frequency ranging from 100 to 10,000 Hz away from the frequency propagated from transducer 236. With signals of this character present, the primary and secondary windings of the hybrid transformer are coupled and the signal transmitted to receiver 374. In contrast, the unwanted signals will typically have much lower frequencies. The detectors in active circuit elements 398 and 400 perceive a slow signal in the same manner as they do a signal originating from transmitter 372, and they balance the impedance in the hybrid transformer primary coils as necessary to cancel the slower moving signal.

From hybrid transformer 370, the frequency-shifted signal of interest, typically having frequency components of 2.5 MHz plus 100–1,000 Hz and 2.5 MHz minus 100–10,000 Hz, is amplified in amplifier 402 (see FIG. 12B) after the frequency-shifted velocity indicative return signal is picked off for the detectors in active circuit elements 298 and 400. After amplification, the return signal is transmitted to an integrated amplifier circuit 404 which is automatic gain controlled and converts the frequency-shifted signal to one of more-or-less constant amplitude; i.e., to one with frequency—the flow velocity related component—as the variable. It is the level of this gain which is utilized in accord with the principles of our invention, and in a manner discussed in more detail hereinafter, to aim the transducer 236 of esophageal probe 220 at the center of the patient's descending aorta 264 and thereby make probe 220 capable of generating a signal from which an accurate measure of the patient's output can be produced.

The gain to amplifier circuit 404 is controlled by an AGC drive controller 406.

The output from automatic gain controlled amplifier circuit 404, a systolic velocity indicative signal, is amplified in a radio frequency amplifier 409. The amplified signal is transmitted to mixers 410 and 411. The return signal is multiplied by COS in one mixer and by SIN in the other as is conventional in a quadrature circuit. The mixers generate in-phase and quadrature signals identified as I and Q in FIG. 12B.

The next stage in receiver 374 consists of a pair of DC notches 412 and 414 which are passive, high-pass filters. These are followed by integrated track-and-hold circuits 416 and 418 which allow receiver 374 to be employed in a pulse as well as a continuous wave mode of operation. Next in line are two-stage amplifiers—420/422 and 424/426.

Figure 12B:
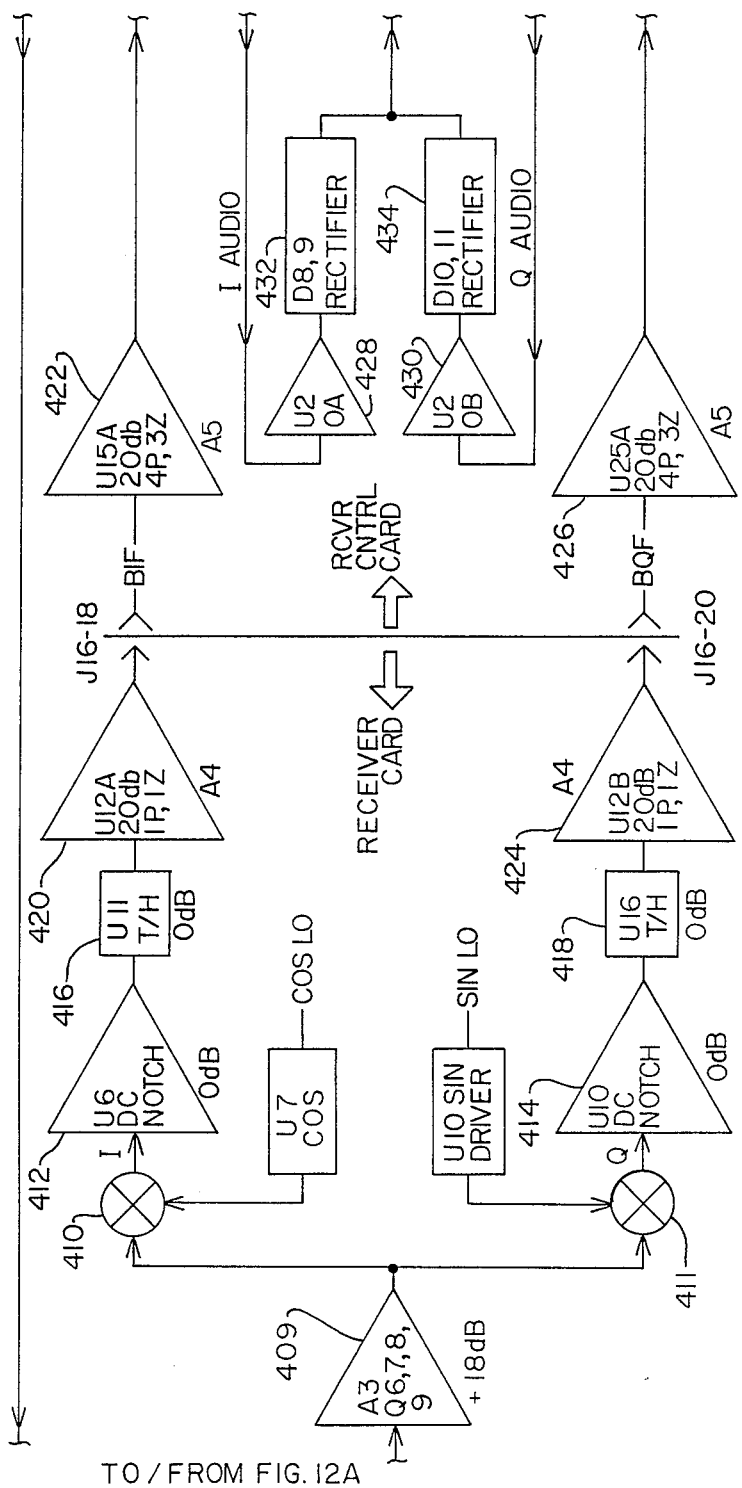
FIG. 12 shows the relationship among FIGS. 12A–12D which, taken together, constitute a block diagram of a transmitter for exciting the transducer of the esophageal probe illustrated in FIGS. 8-11 and a receiver for processing frequency-shifted energy transmitted to it from the transducer of the esophageal probe.
Figure 12D:
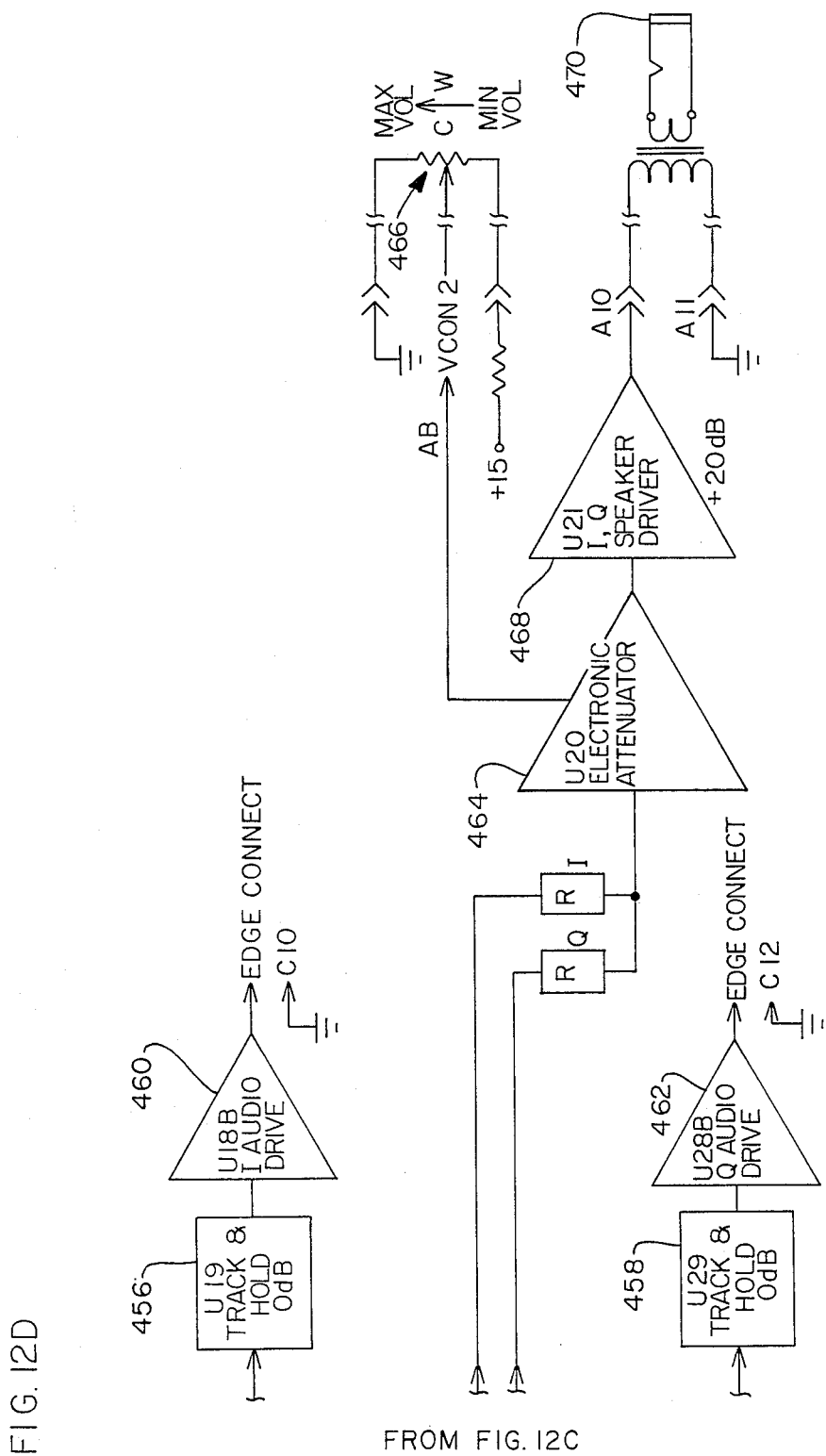

After the second stage of amplification, the I and Q channels are split between the receiver circuitry shown in FIGS. 12B–12D and detectors 428 and 430 which generate the feedback signals for automatic gain controller 406. The signals from detectors 428 and 430 are converted to DC signals in rectifiers 432 and 434, and the rectified signals are summed with the gain of the summation signal being increased in amplifier 436. The amplified signal is applied to integrator 438 which is a low-pass filter. Rectification is employed so that the feedback signal available from integrator 438 will represent the amplitude of the frequency-shifted signal made available to receiver 374 from the transducer 236 of the esophageal probe 220.

As is shown in FIG. 56E, the I and Q signals are also applied to buffers 440 and 442. These active circuit elements provide impedance matching of the circuit with automatic gain control feedback detectors 428 and 430.

To filter out any remaining components of the frequency-shifted signal that would have the frequencies associated with reflection of the transducer propagated energy from large anatomical structures such as bones and slow moving structures such as lungs, the signals processed in buffers 440 and 442 are transmitted to high-pass filters 444 and 446. These are conventional integrated circuits designed to filter out low frequencies.

Systems such as those illustrated in FIG. 12 can confuse very high frequency signals with low frequency signals if both arise simultaneously. To eliminate very high frequency components of the I and Q signals, they are processed through low-pass, anti-alias PRF filters 448 and 450. These are also conventional integrated circuits.

The filtered signal components are amplified in amplifiers 452 and 454 and applied to integrated track-and-hold circuits 456 and 458. These conventional circuits hold the analog signal components designated I and Q so that they can be converted to digital signals and processed by the fast Fourier transform technique described in Patent No. 4,509,526.

The final active circuit components 460 and 462 illustrated in FIG. 12 are conventional audio drives which provide buffering between the circuit components just described and those (not shown) in which the analog-to-digital conversions of signal components I and Q are performed. These, and the components for converting the return signal appearing at transducer 236 to a visual display of the systolic velocity of the blood flowing through a patient's descending aorta, are not shown in the drawings and will not be discussed herein because they are not part of the present invention and because those systems components can be akin to the corresponding circuit elements of the equipment disclosed in Patent No. 4,509,526.

As is shown in FIG. 12C, the in-phase and quadrature signal components designated I and Q are also picked off between amplifier 452 and track-and-hold circuit 456 and between amplifier 454 and track-and-hold circuit 458. These signal components are combined, and the resulting signal is applied to an attenuator 464 which is conventional and acts as an audio volume control. Volume can be adjusted by a potentiometer 466 available to the operator of the cardiac monitoring apparatus 18 in which esophageal probe 220 and transmitter/receiver 372/374 are incorporated.

From volume control 464, the processed signal indicative of the patient's systolic velocity is applied to a speaker driver 468. This drives a speaker 470 which allows the operator to listen to the blood flowing through the patient's descending aorta.

Figure 13:
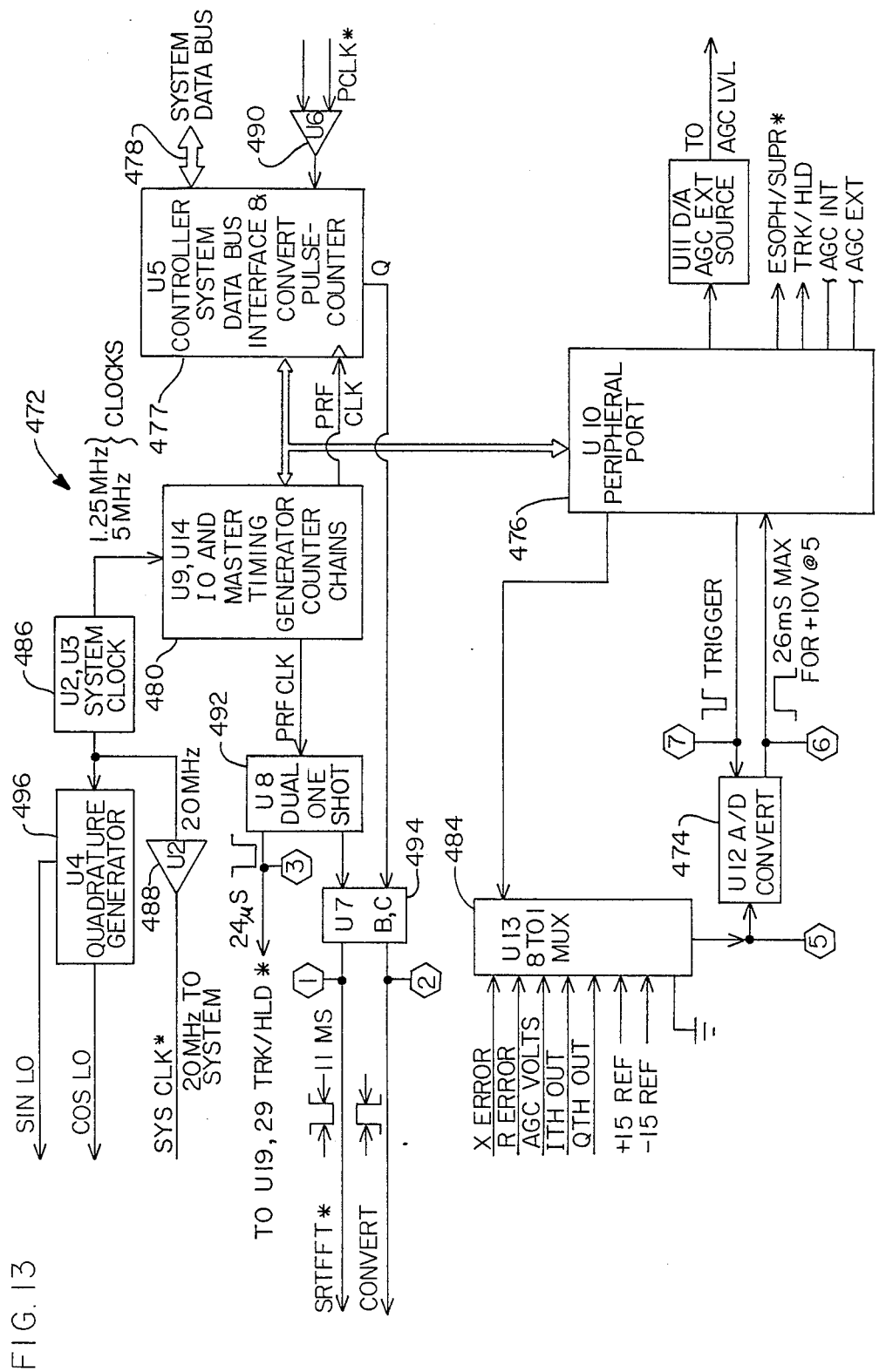
FIG. 13 is a block diagram of an interface which can be employed to couple the signal processing circuitry to a microprocessor or other general purposes computer incorporated in the apparatus of FIG. 1.

It will be apparent to the reader that the transmitter/receiver system just discussed is intended to be computer controlled. An appropriate interface between the transmitter/receiver hardware and the Zilog 8000 microprocessor controlling the operation of that hardware (not shown) is illustrated in FIG. 13 and identified by reference character 472. Among the active circuit devices in interface 472 is an analog-to-digital converter 474. This converter enables the computer to ascertain whether the inductance in the receiver circuitry is properly matched to the transducer 236 in probe 220 and whether the impedances in the primary windings of hybrid transformer 370 are balanced. It also allows the computer to identify the amount of gain being affected by automatic gain controller 406. The signals designated +15 Ref and −15 Ref can also be digitized to ascertain whether the transmitter/receiver system is operating properly.

In addition to the analog-to-digital converter, interface 472 includes a peripheral port 476 and a controller 477. The latter is an integrated circuit that provides an interface between: (a) a system data bus 478, and (b) peripheral port 476 and master timing generator 480.

The master timing generator allows the transmitter/receiver controlling computer to set clock rates which control high-pass wall filters 444 and 446 and anti-aliasing filters 448 and 450 as well as the four track-and-hold circuits 416, 418, 456, and 458.

Peripheral port 476 controls various ones of the active circuit elements in the transmitter/receiver system, such as the switch 384 which determines whether receiver 374 will accept signals from an esophageal or a suprasternal notch probe and the several track-and-hold circuits. Peripheral port 476 also controls the operation of an 8:1 multiplexer 484 through which the signals to be analyzed are brought into analog-to-digital converter 474.

Also incorporated in interface 472 is a clock 486 which controls the operation of the transmitter/receiver system. And another active circuit component included in interface 472 is a buffer 488 for the clock pulses.

Circuit element 490 gates clock pulses into the interface controller 477; and circuit elements 492 and 494 are, respectively, a dual one-shot and a flip-flop which provide appropriate signals for controlling the operation of the track-and-hold circuits and electrically interface the transmitter and receiver with the host computer.

Finally, interface 472 includes a quadrature generator 496 which generates the reference signals SIN LO and COS LO discussed above.

The operation of the novel cardiac monitor 18 discussed above and illustrated in FIG. 1 will be apparent from the ensuing discussion of FIGS. 17–55. These figures depict the instructions and other messages that appear on the advisory 30 of screen 28 as the operator of cardiac monitoring apparatus 18 follows the protocol we employ to measure the cardiac output of a patient.

Figure 17:
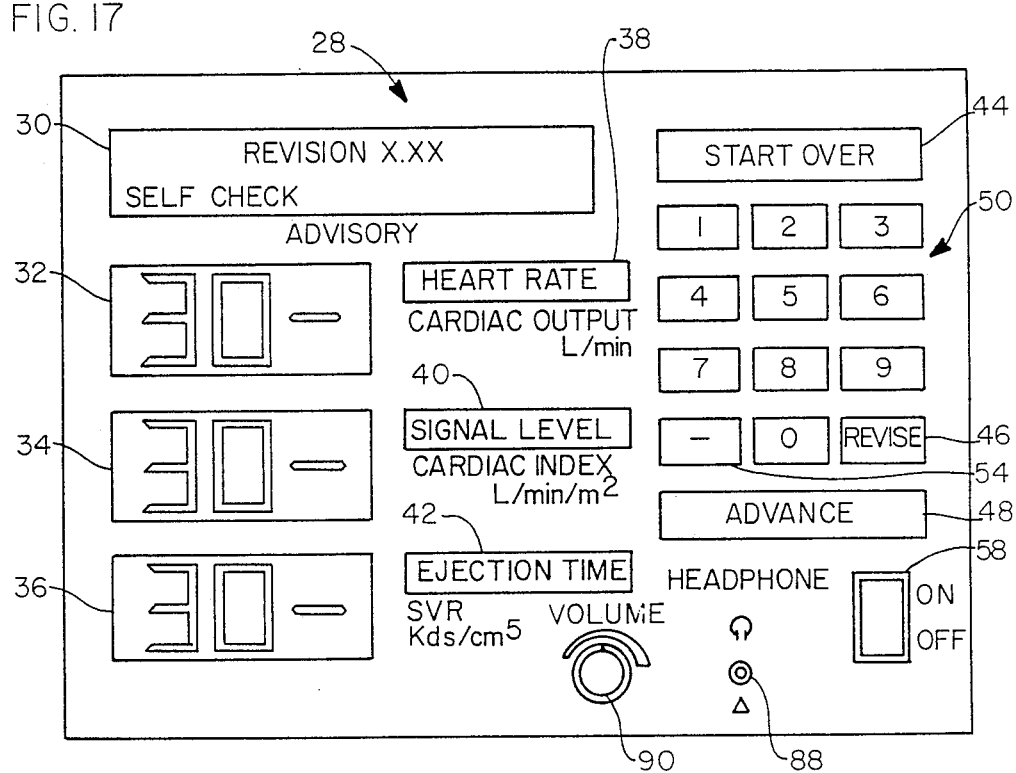
FIGS. 17-55 are illustrations of the visual display of the cardiac output monitoring apparatus shown in FIG. 1; these Figures show the prompts and advisories that appear as the operator sets the cardiac monitoring apparatus up to monitor a patient's cardiac output (and/or cardiac index and/or systemic vascular resistance) and shows the type of information that is displayed when the cardiac monitoring apparatus has been set up and is operating in the monitoring mode.

Turning first to FIG. 17, the initial step in this procedure is to press on-off switch 58. That turns the monitoring apparatus 18 on and initiates a self-check of the apparatus. LED displays 32, 34 and 36 are illuminated with the number 30 when the self-check starts. This number decreases at the rate of one digit per second and indicates that the self-check is in progress.

Keyboard 50 ignores all attempts to input data through it while the self-check is in progress.

Figure 18:
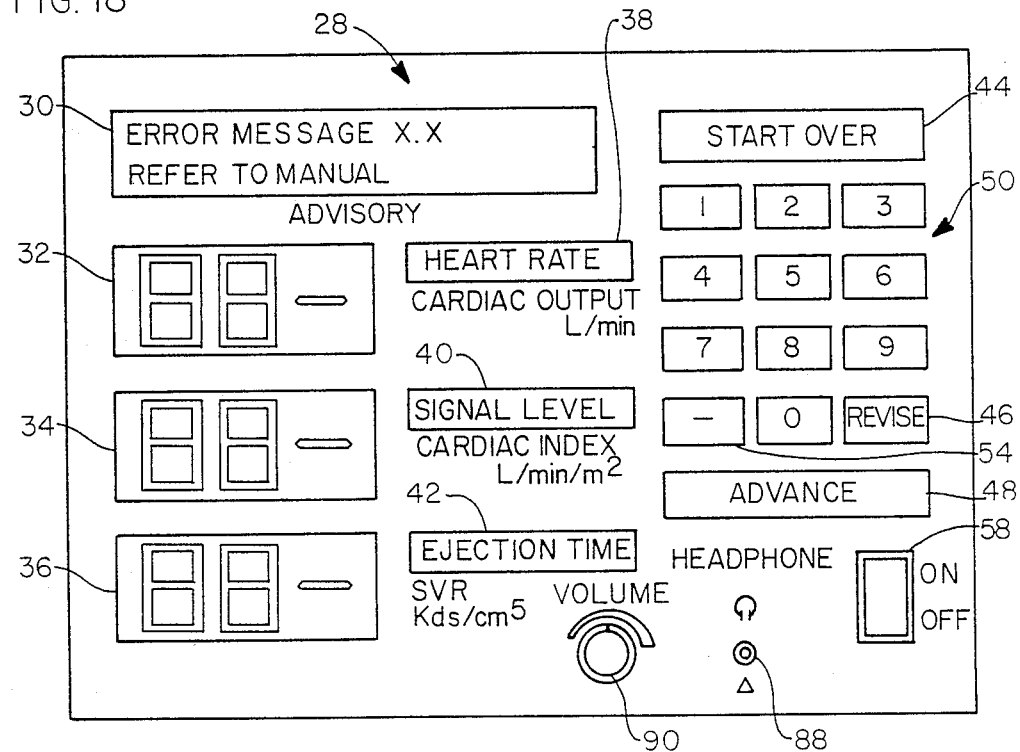

If a real or suspected fault is detected during the course of the cardiac monitor self-check, the LED displays will stop counting; advisory 30 will continue to ignore inputs; and the error message shown in FIG. 18 will appear on screen 28. The illustrated error message is not displayed if the cardiac monitor 18 has not been correctly set up; i.e., if the ultrasonic esophageal probe 220 has not been connected. Instead, screen 28 will display the message NO ESOPH PROBE DETECTED, ADVANCE IF OK, or FIX.

Figure 19:
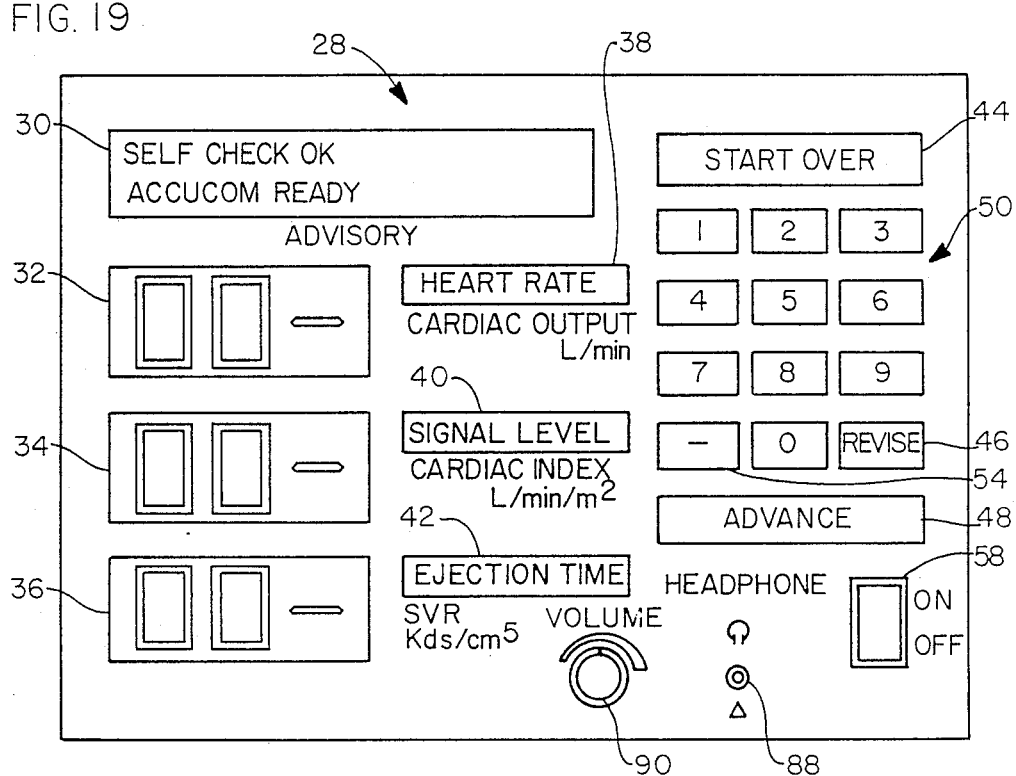

Upon completion of the self-check, the double digit 00 in LED displays 32, 34, and 36 will flash on and off three times at the rate of one cycle per second; and advisory 30 will display the message shown in FIG. 19, indicating that the cardiac monitor is operating satisfactorily and that the cardiac output measuring sequence can be initiated. Keyboard 50 will continue to ignore inputs.

When he has been advised that the machine is in a ready status, the operator pushes ADVANCE key 48. This results in advisory 30 displaying a message (shown in FIG. 20) which instructs the operator to select the measurement he wishes to obtain—cardiac output, cardiac index, systemic vascular resistance—or any combination of the foregoing measurements. Cardiac output, cardiac index, and systemic vascular resistance are selected by depressing keys 1, 2, and 3, respectively, on keyboard 50. The number of the key which has been pressed in the measurement selection step flashes on message unit 30. In addition, bars appear in the appropriate LED display 32, 34, and 36 as a measurement is selected.

Keyboard 50 ignores attempts to enter instructions through the other keys while one or more of the foregoing measurements are being selected.

Table 1 below shows the measurements which can be selected and the figure of the drawing which has the advisory message for each of the seven possible selections.

| Drawing FIG. | Measurement (s) Selected |
| --- | --- |
| 21 | Cardiac Output |
| 22 | Cardiac Output and Cardiac Index |
| 23 | Cardiac Output, Cardiac Index, and Systemic Vascular Resistance |
| 24 | Cardiac Index |
| 25 | Systemic Vascular Resistance |
| 26 | Cardiac Output and Systemic Vascular Resistance |
| 27 | Cardiac Index and Systemic Vascular Resistance |

Figure 28:
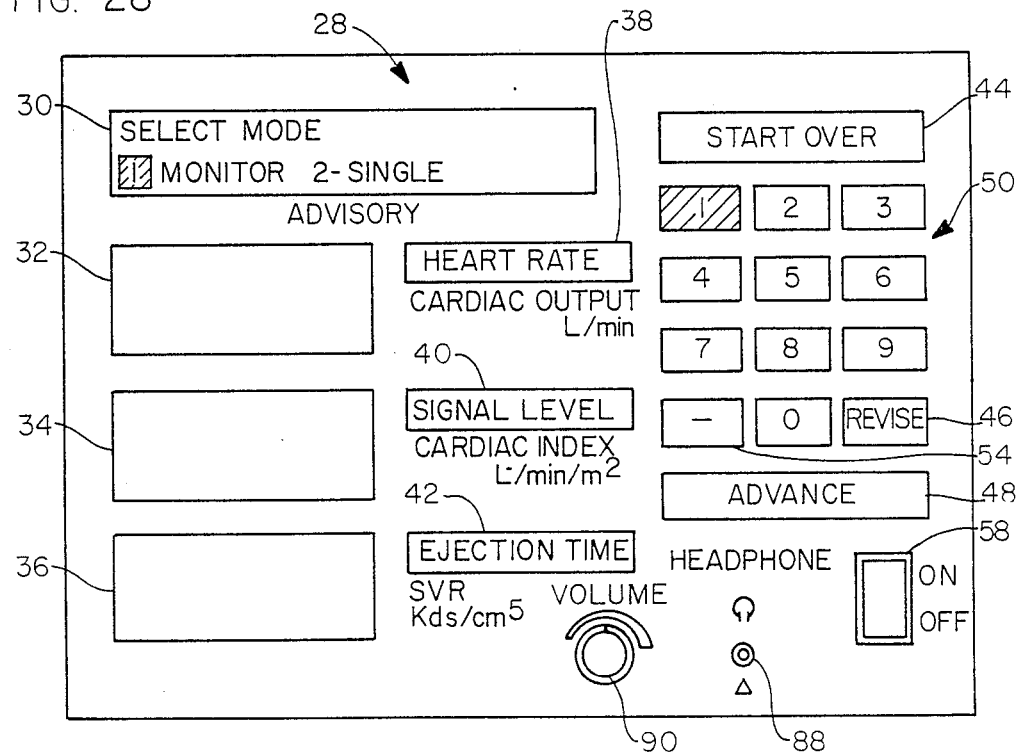

Following the selection of one or more of the foregoing measurements, the operator proceeds to the next step in the measurement protocol by pressing ADVANCE key 48, causing advisory 30 to display the SELECT MODE message shown in FIG. 28. This instructs the operator to elect either a continuous mode of measurement or a single mode. The former (shown selected in FIG. 28) is wanted in circumstances where it is desirable to continuously monitor a measurement such as the cardiac output of a patient undergoing surgery. The single mode of measurement (FIG. 29) is employed for training and when suprasternal notch probe 326 is used as discussed above to provide the one-time or infrequent determination of the systolic blood flow velocity through the patient's ascending aorta for the generation of a scaling factor.

Figure 29:
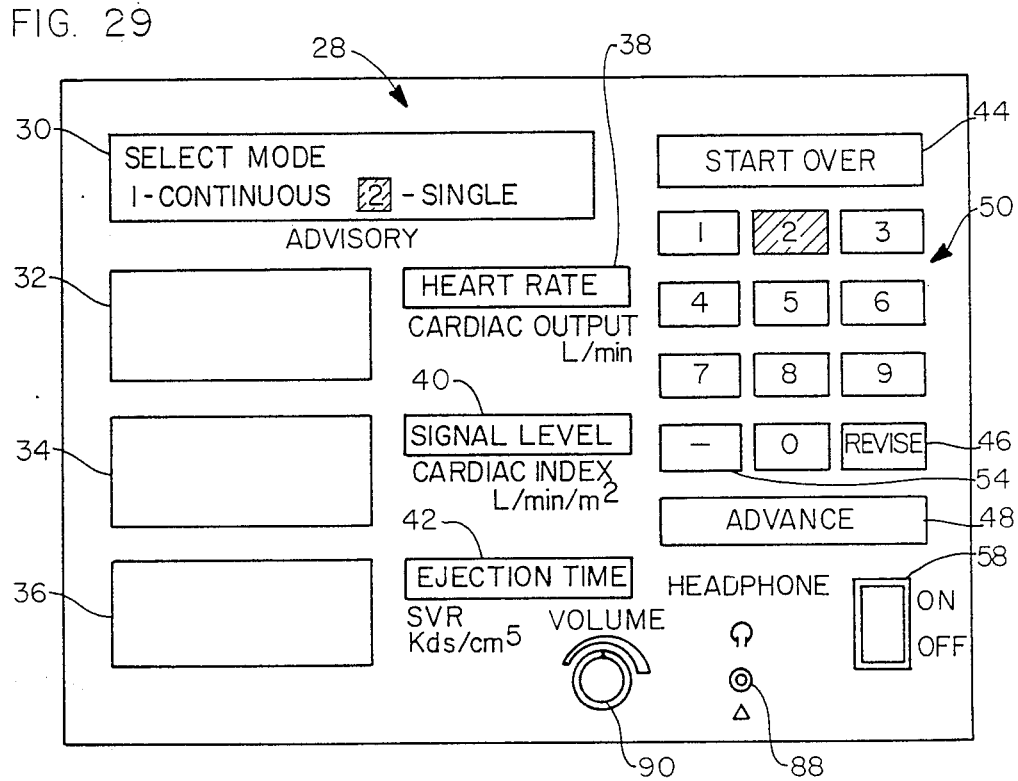

Only one mode may be selected. A second entry erases the first entry. As shown in FIGS. 28 and 29, the number 1 flashes in advisory 30 if the continuous mode of measurement is selected; "2" flashes if the single mode is selected.

Appropriate ones of the LED displays 32, 34, and 36 remain lit to identify the measurement or measurements that the operator elected.

Figure 20:
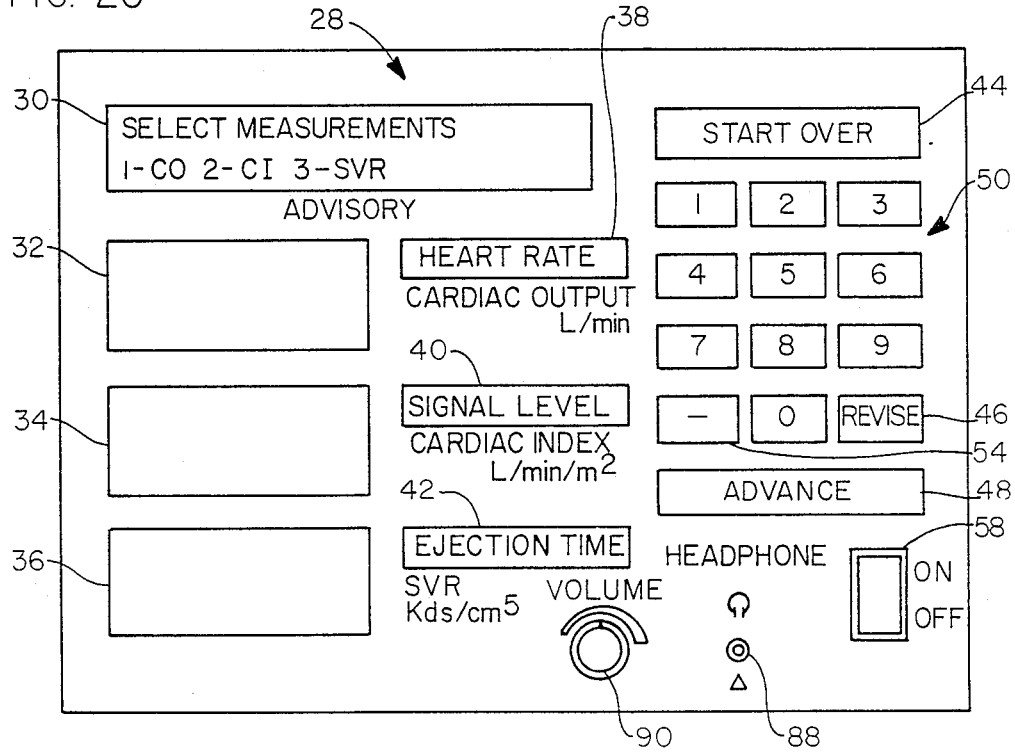
Figure 21:
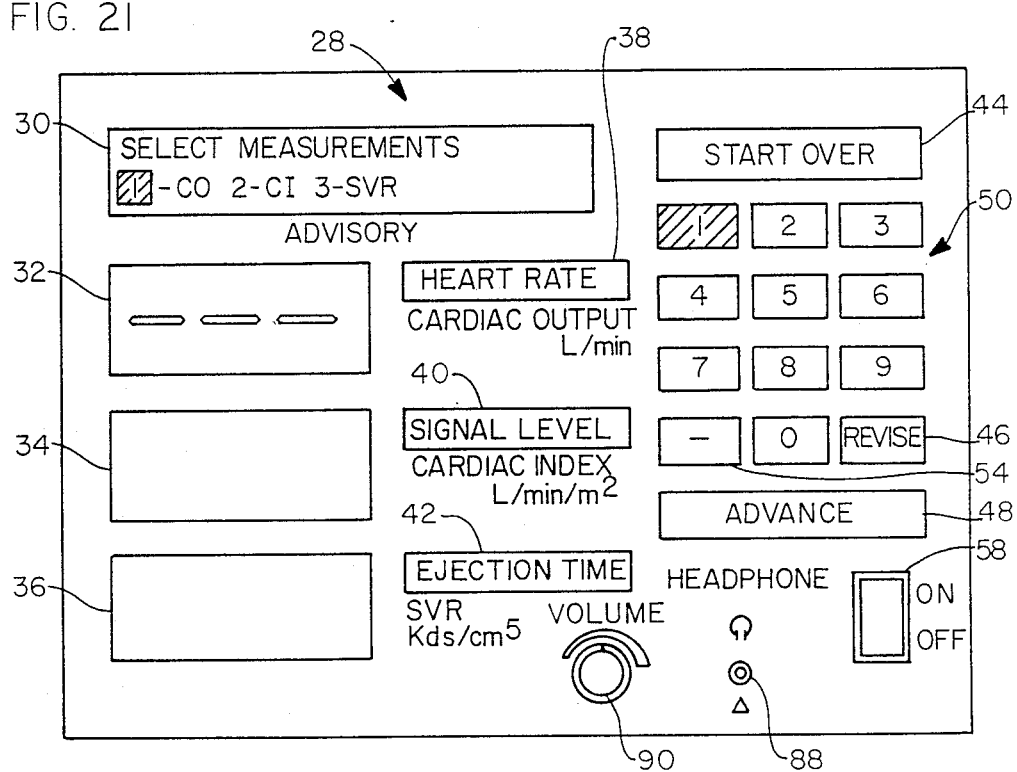
Figure 22:
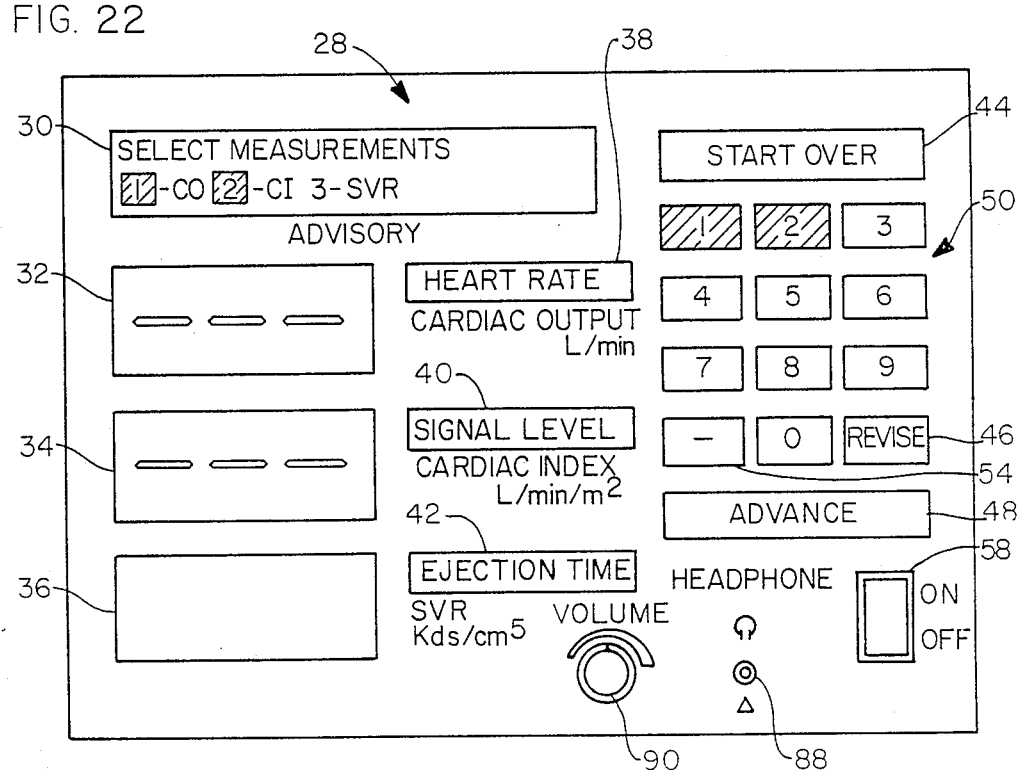
Figure 23:
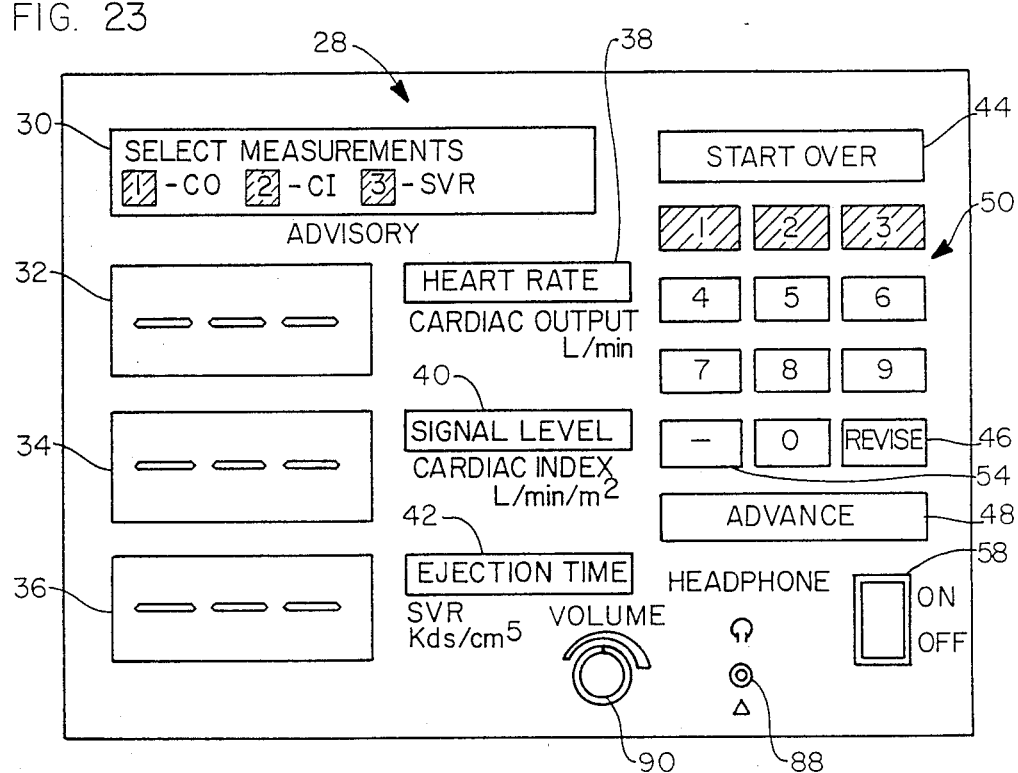
Figure 24:
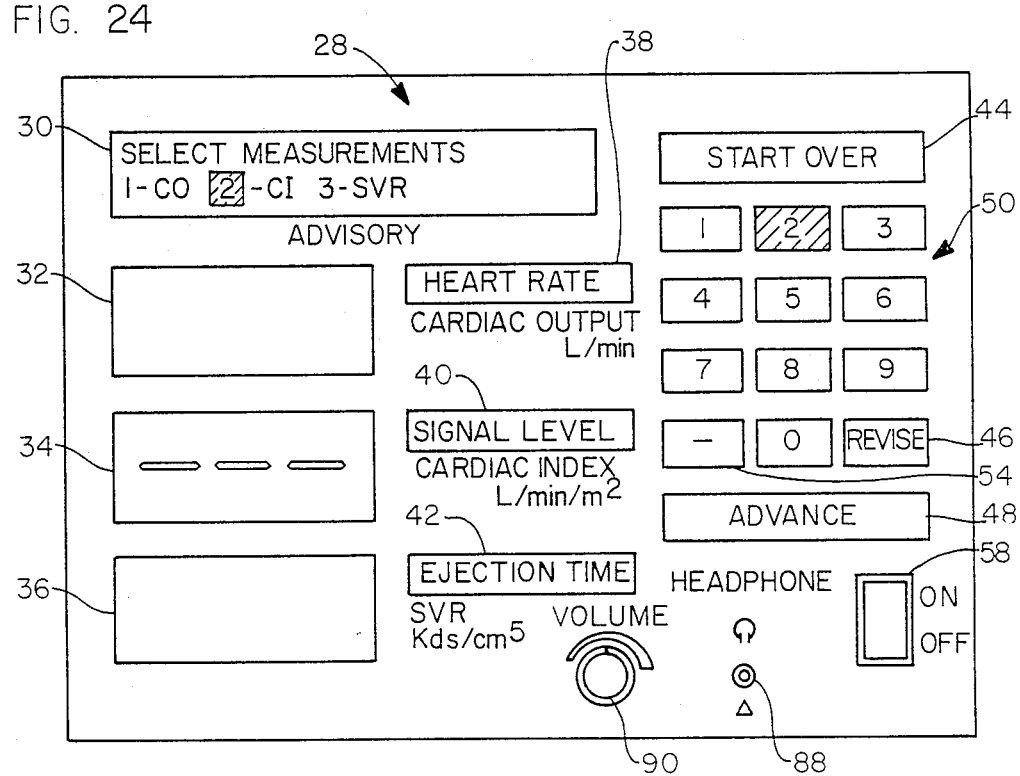
Figure 25:
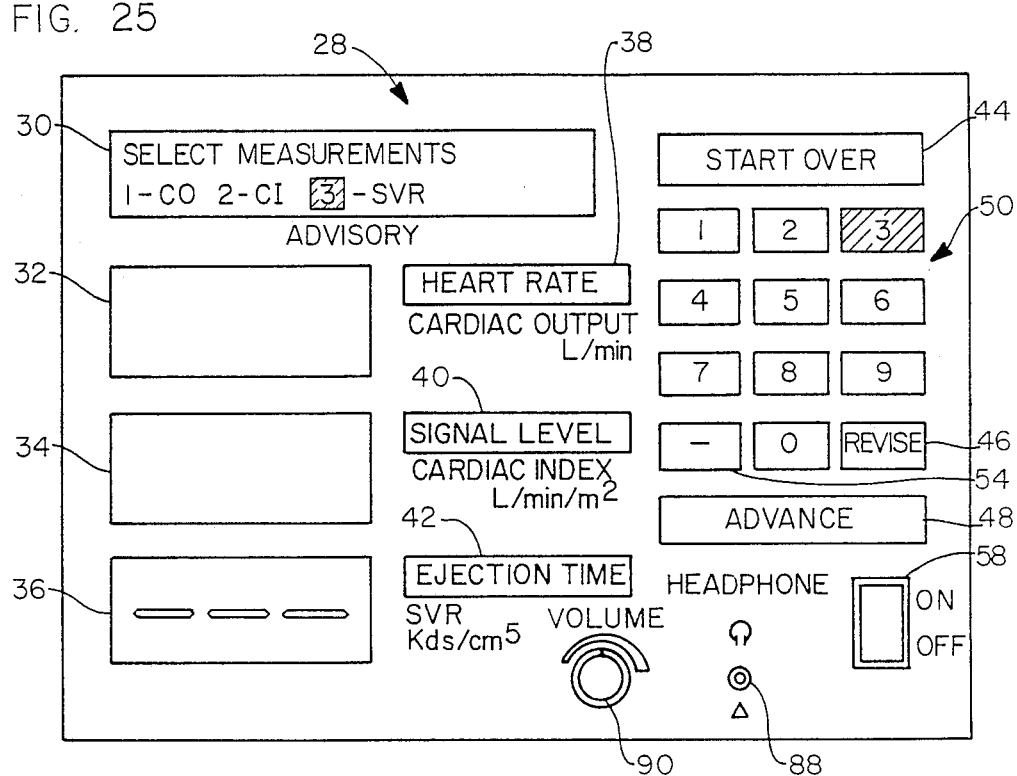
Figure 26:
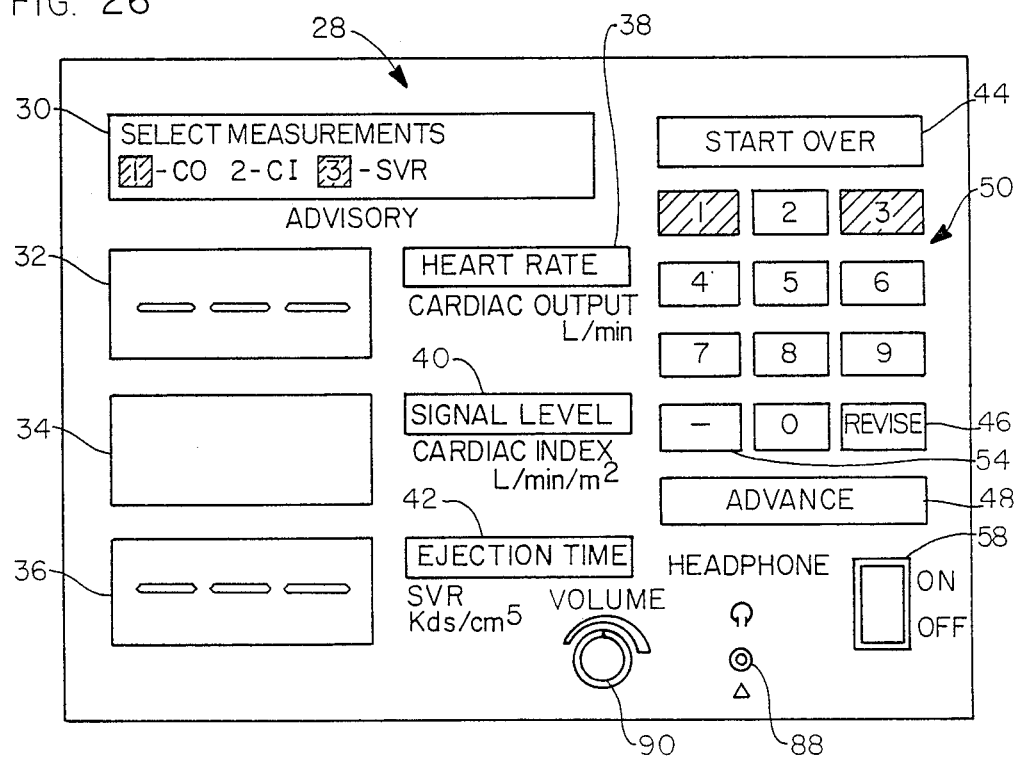
Figure 27:
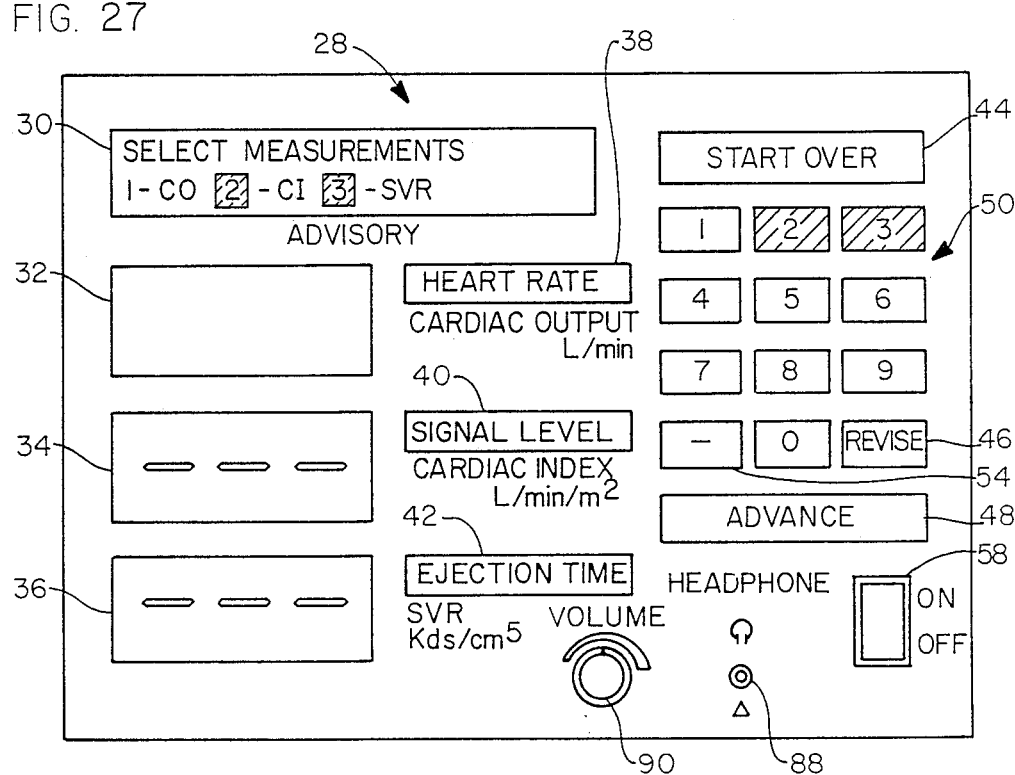
Figure 30:
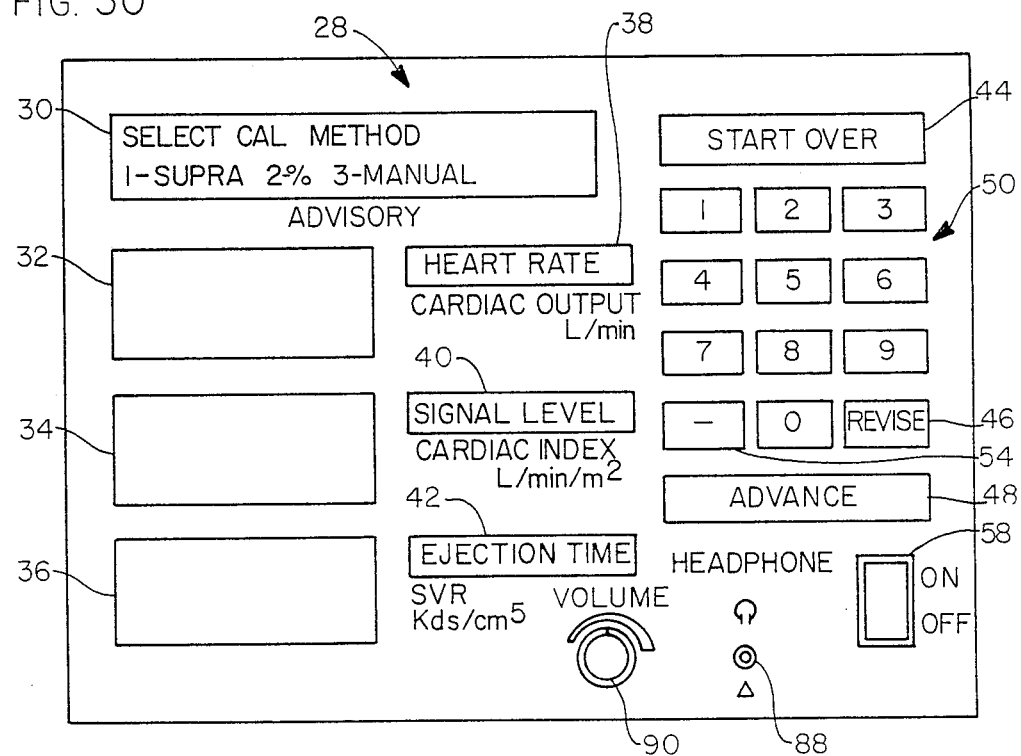
Figure 31:
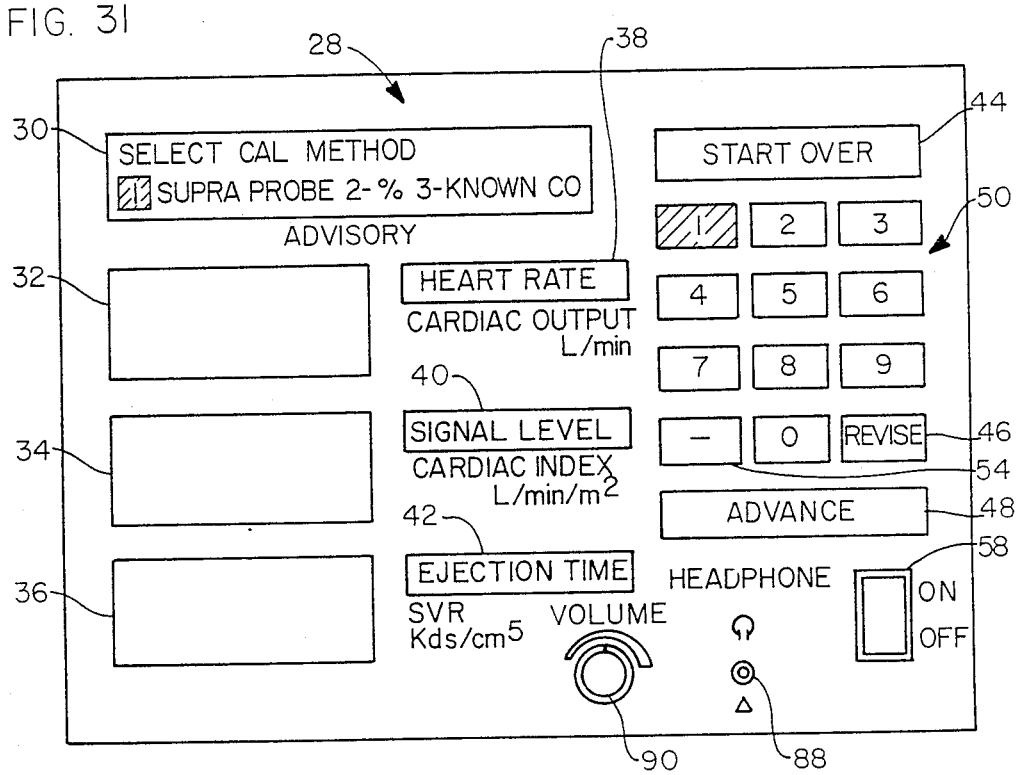
Figure 32:
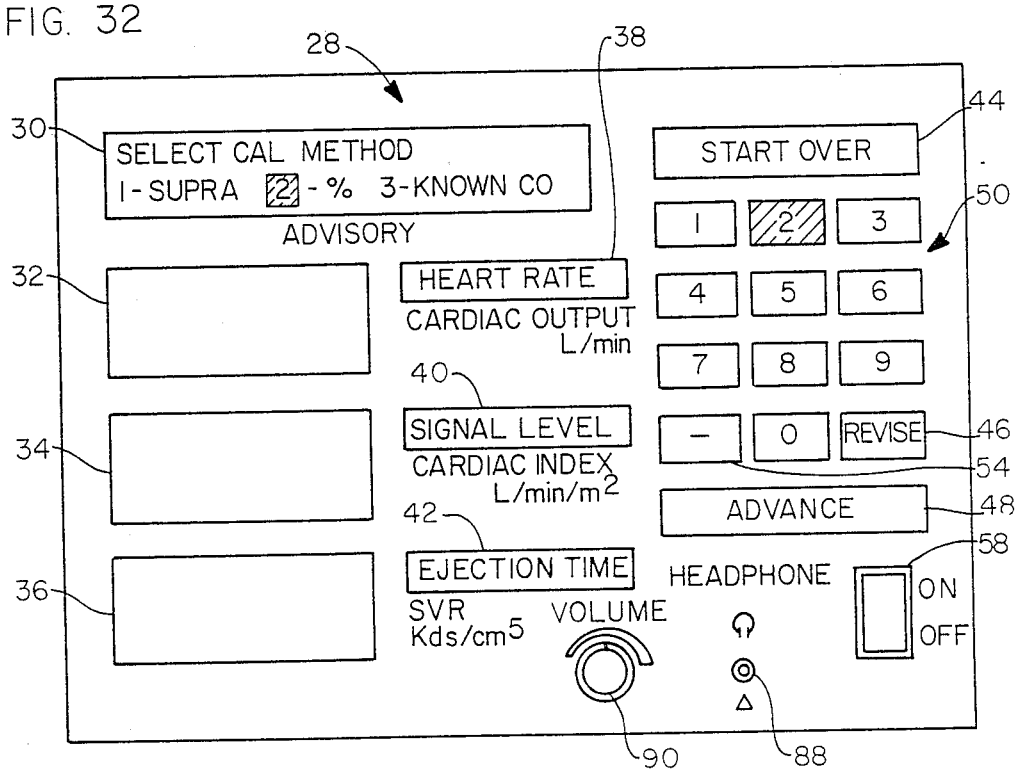

The operator can now press either START OVER key 44 or REVISE key 46 if he wishes to select a different measurement, or he can press ADVANCE key 48 to proceed to the next step in the operating sequence which is labeled SELECT CAL MODE in FIG. 30 (in this and the other steps of the protocol for measuring cardiac output, the pressing of REVISE key 46 will backspace the program one step unless indicated otherwise) and the pressing of START OVER key 44 will return the program running in apparatus 18 to the step shown in FIG. 20.

Figure 33:
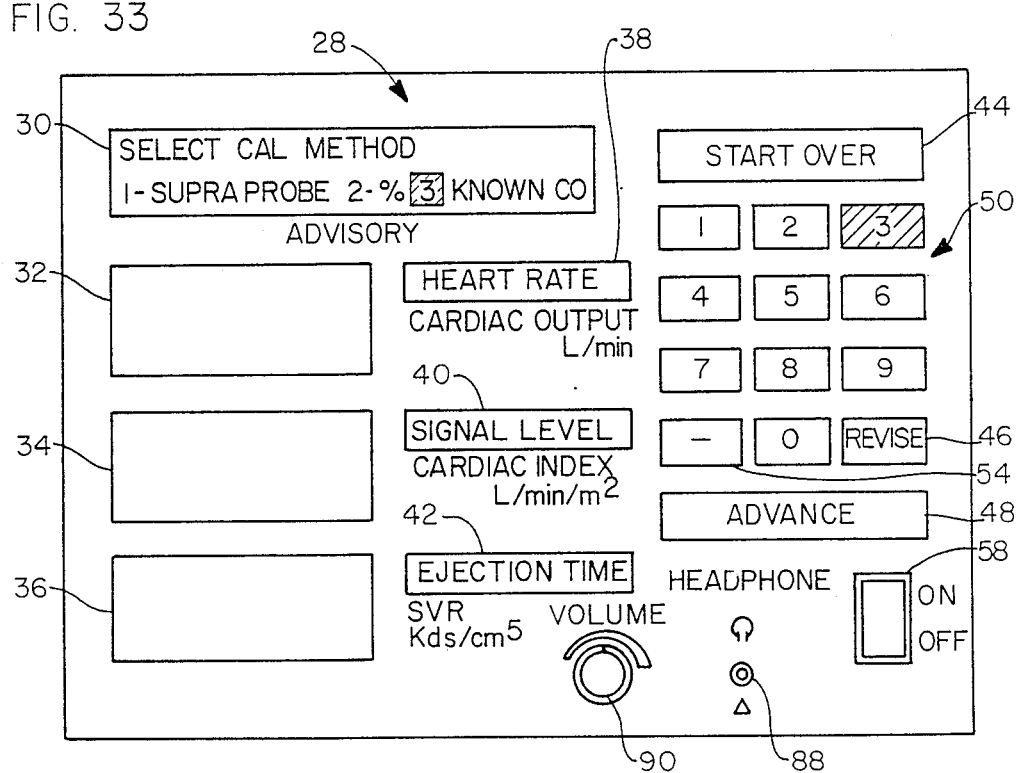

Pressing ADVANCE key 48 after key 1 brings up the SELECT CAL METHOD advisory shown in FIG. 30. The advisory also instructs the operator to press key 1 of keyboard 50 if the suprasternal notch probe method of calibrating the systolic flow velocity is to be employed (FIG. 31), to press key 2 if the trending mode of monitoring the patient is to be used (FIG. 32), and to press key 3 if a known calibration factor is to be used (FIG. 33). In the trending mode, monitoring apparatus 18 monitors increases and decreases in the patient's cardiac output (and/or cardiac index and/or systemic vascular resistance) and displays the result as a percentage of a baseline value.

As is also shown (see FIGS. 31, 32, and 33), the numeral 1 flashes if key 1 is depressed to select the suprasternal notch mode of calibration while the numeral 2 flashes if key 2 is depressed to select the trending mode of monitoring, and key 3 flashes if that key is depressed as it is when a known calibration (or scaling) factor is decided upon.

Only one calibration is permitted. A second selection will void the first.

The appropriate LED display or displays 32, 34, and 36 remain lighted to advise the operator of his choice of measurement or measurements.

Figure 34:
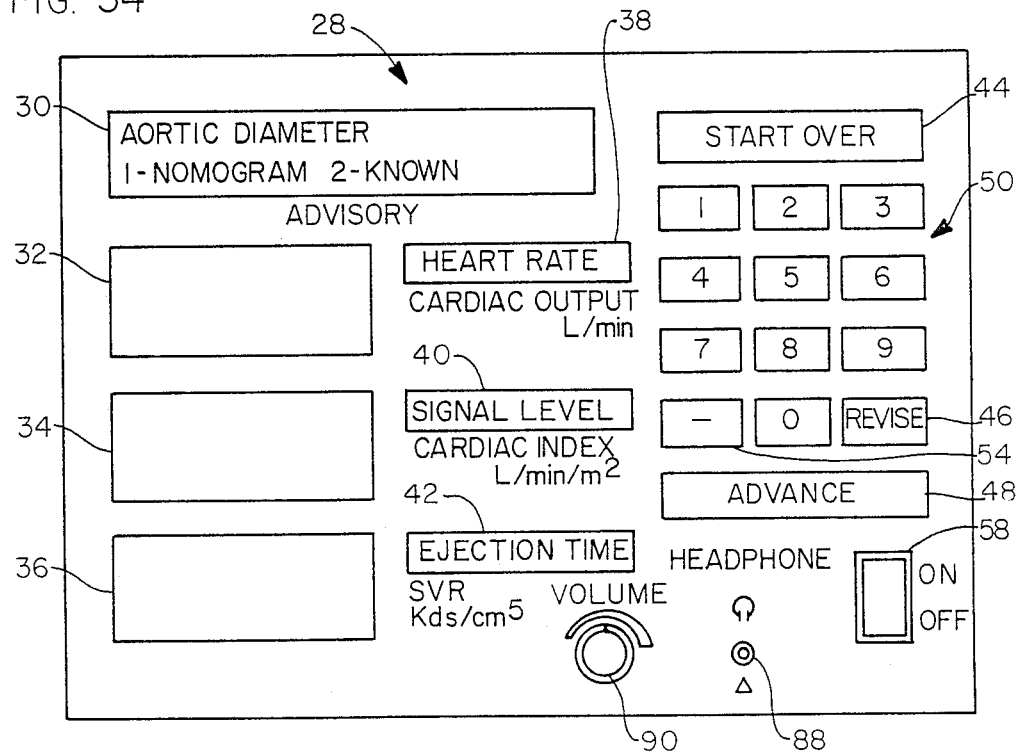
Figure 35:
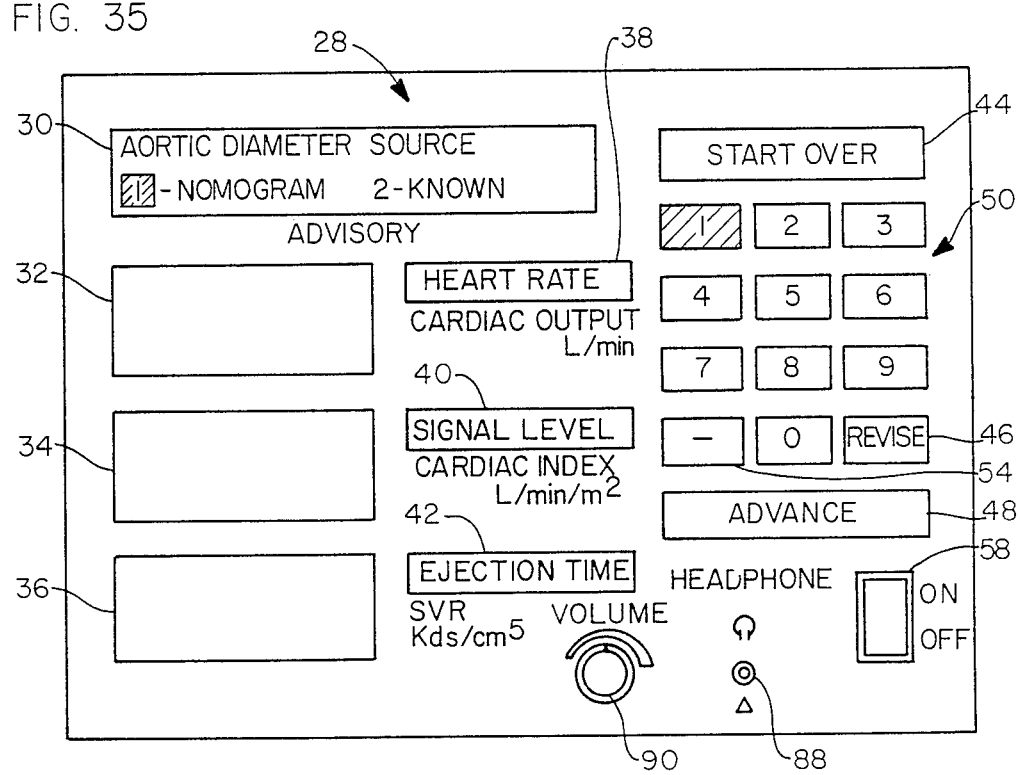

The pressing of ADVANCE key 48 following the electrion of the calibration method brings up the prompt AORTIC DIAMETER SOURCE shown in FIG. 34. Two choices are available. The diameter of the patient's ascending aorta may be automatically calculated from his height, weight, age, and sex by solving the algorithm set forth above. Alternatively, this diameter may be known and the election be to use the known value.

Key 1 is pushed to elect the NOMOGRAM method, and key 2 is pushed to select KNOWN. The number 1 will flash on message unit 30 if NOMOGRAM is selected (see FIG. 35), and numeral 2 will flash if KNOWN is chosen (see FIG. 36).

Only one selection is permitted with a subsequent entry voiding a preceding one.

Appropriate LED displays, 32, 34, and 36 remain lighted.

Figure 36:
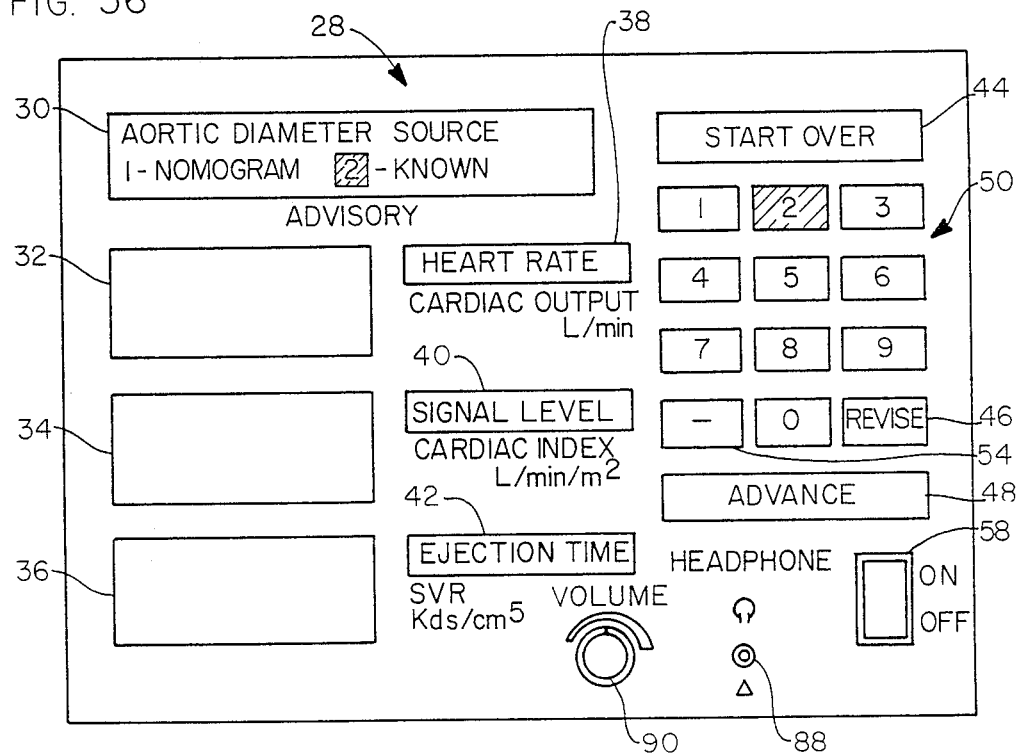
Figure 36A:
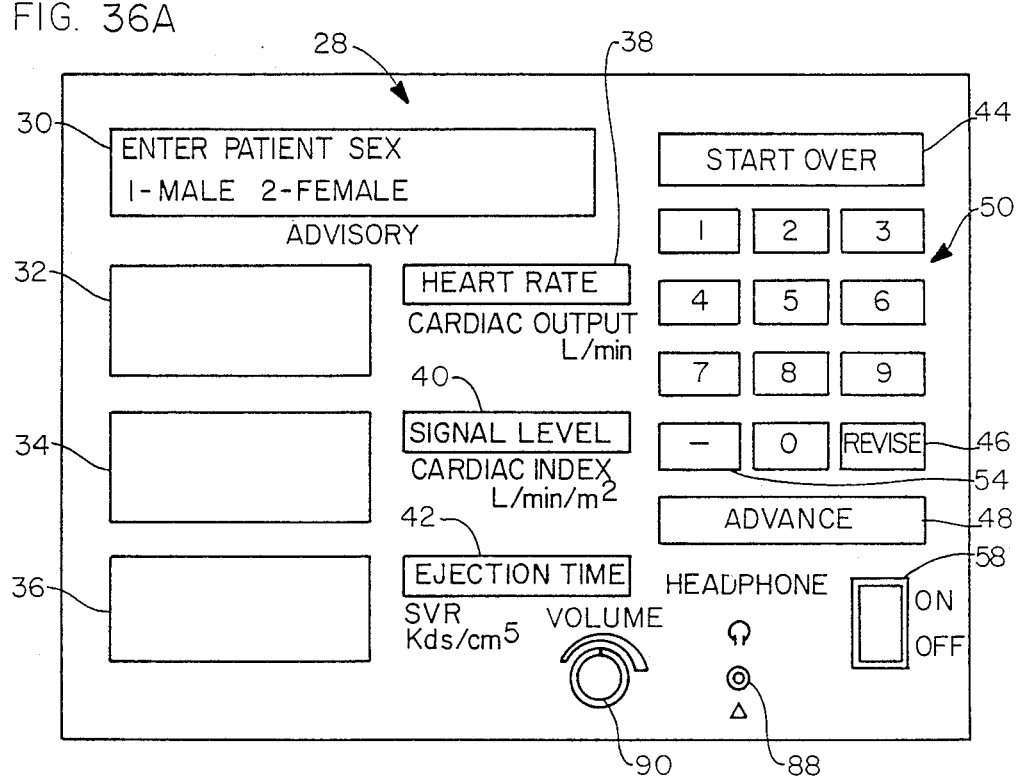

The operator may proceed to the next step in the operating sequence by pressing ADVANCE key 48. The depression of key 48 after key 1 has been depressed to select the nomogram method of providing the patient's aortic diameter brings up the advisory ENTER PATIENT'S SEX shown in FIG. 36A. The advisory also instructs the operator to press key 1 if the patient is a male and to press key 2 if she is a female.

Figure 37:
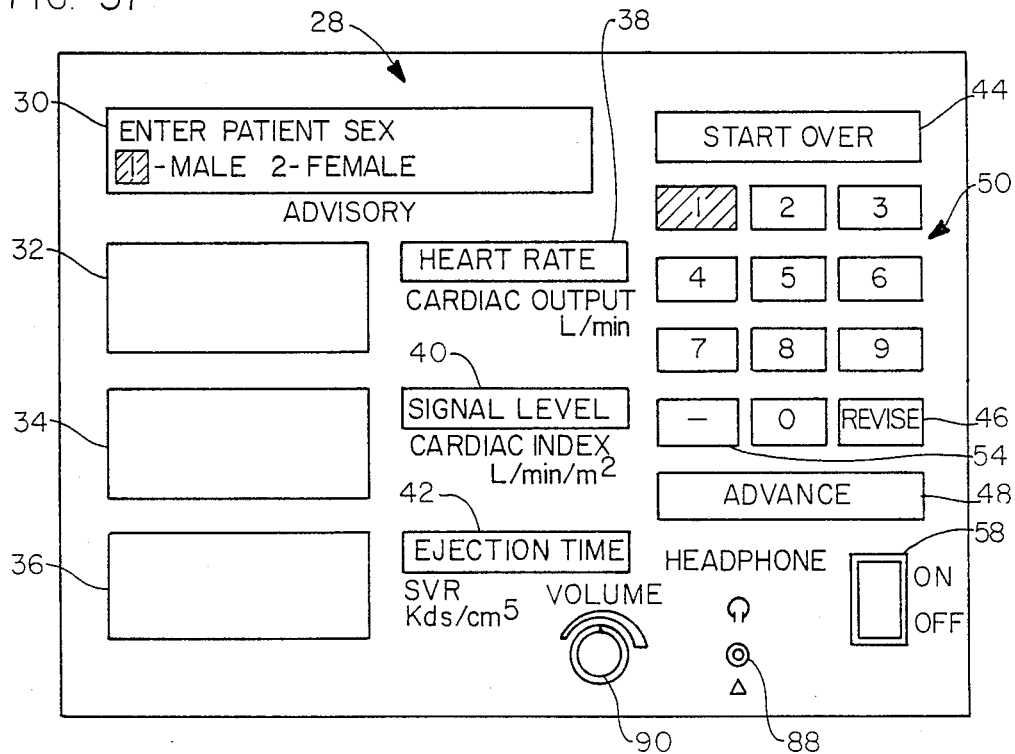
Figure 38:
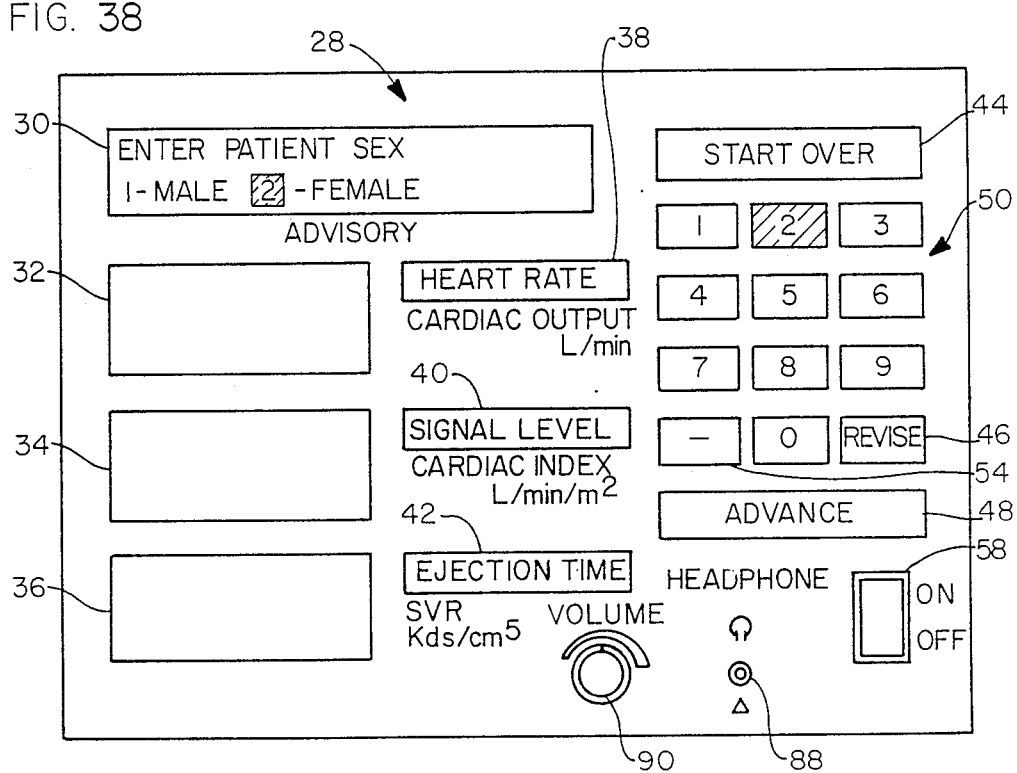

The numeral 1 will flash on the advisory if key 1 is pressed, and the numeral 2 will flash if key 2 is pressed (see FIGS. 37 and 38, respectively). Only one choice is permitted; any subsequent entry voids the preceding one.

Again, the appropriate LED displays 32, 34, and 36 remain lighted so that the operator will remain aware of the measurements (cardiac output, cardiac index, and systemic vascular resistance) that have been elected.

Figure 39:
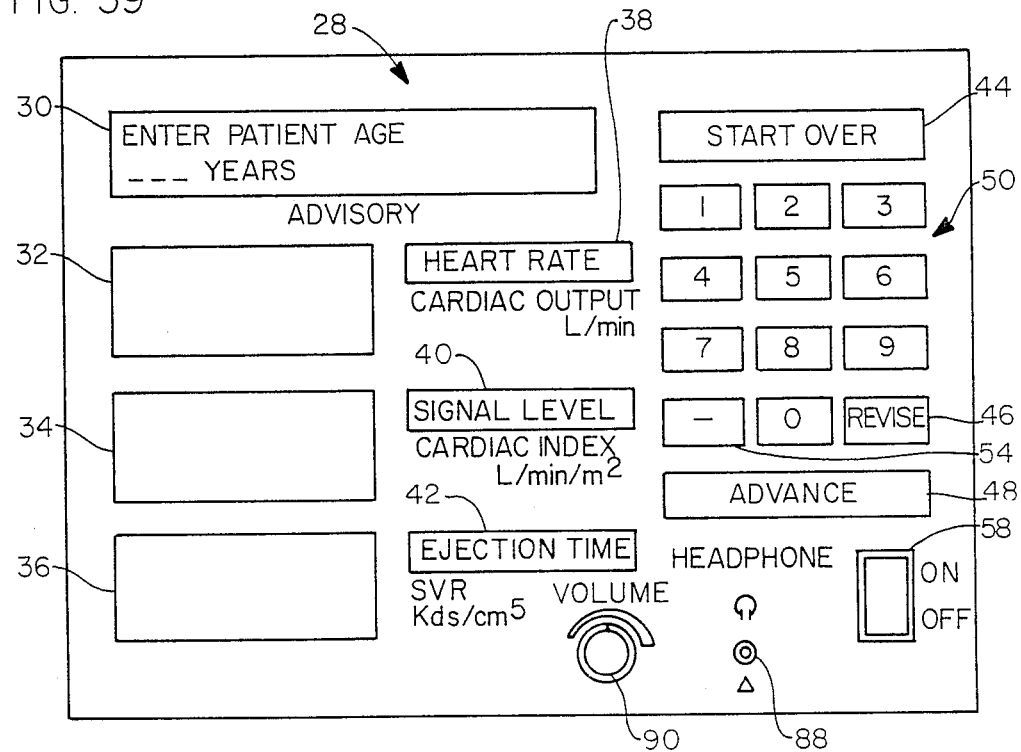

To advance to the next step in the operating sequence, the operator presses ADVANCE key 48, bringing up an instruction to enter the patient's age. The prompt, ENTER PATIENT'S AGE, is shown in FIG. 39.

The patient's age (in years) is entered by pressing the appropriate keys on keyboard 50. The numbers which are entered (maximum of three) are displayed in the advisory 30 so that the operator can visually confirm that he has correctly entered the patient's age.

The appropriate LEDS 32, 34, and 36 still remain lighted to call to the operator's attention the measurement choices he has made.

Figure 40:
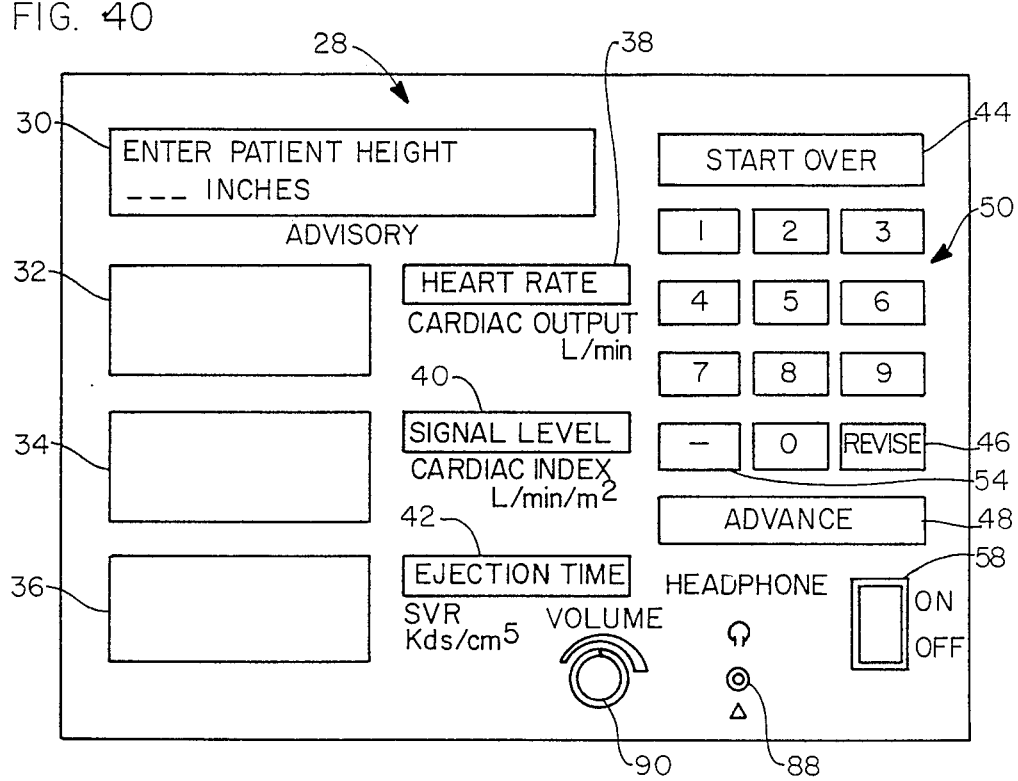
Figure 41:
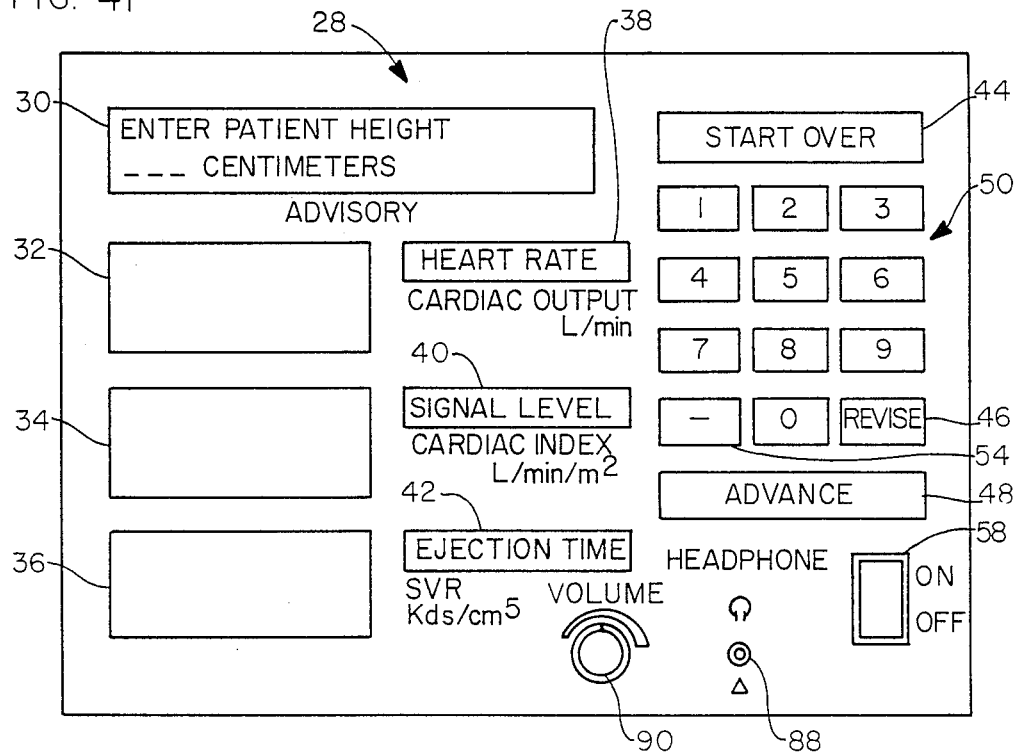
Figure 42:
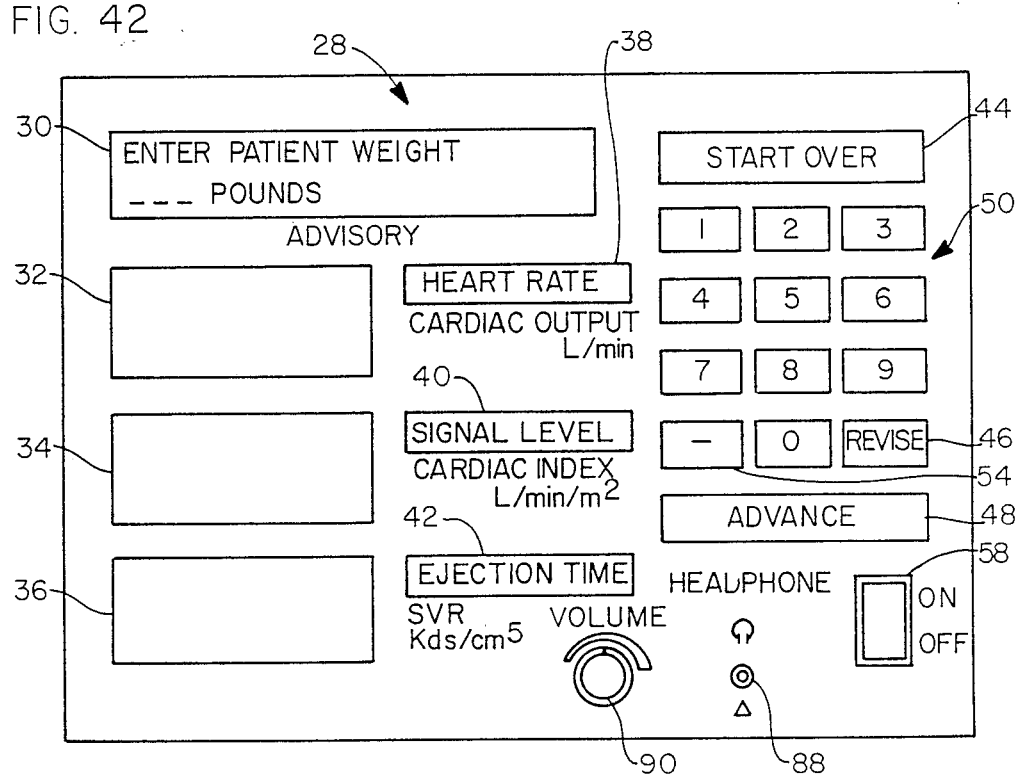

Pressing the ADVANCE key 48 after the patient's age has been entered brings up the instruction ENTER PATIENT HEIGHT (FIGS. 40 and 41). The patient's height is entered in English (FIG. 40) or metric (FIG. 41) units by pushing not more than three keys on keyboard 50. The entry is displayed in advisory 30, allowing the operator to confirm that the entry was correctly made.

The LED displays remain unchanged at this point.

Cardiac monitor 18 is programmed to automatically identify the system of measurement used in entering the patient's height. It will be appreciated that this is easily accomplished because the sets of numbers are quite different in the two systems. For example, if the patient is six feet tall, 72 will be entered if the information is available in the English system while 178 will be entered if the information is instead in the metric system.

After the height entry has been completed, the operator presses ADVANCE key 48 to bring up the next prompt in the sequence employed to set cardiac monitoring apparatus 18 up for the monitoring mode. This prompt (see FIGS. 42 and 43) is designated ENTER PATIENT WEIGHT.

Figure 43:
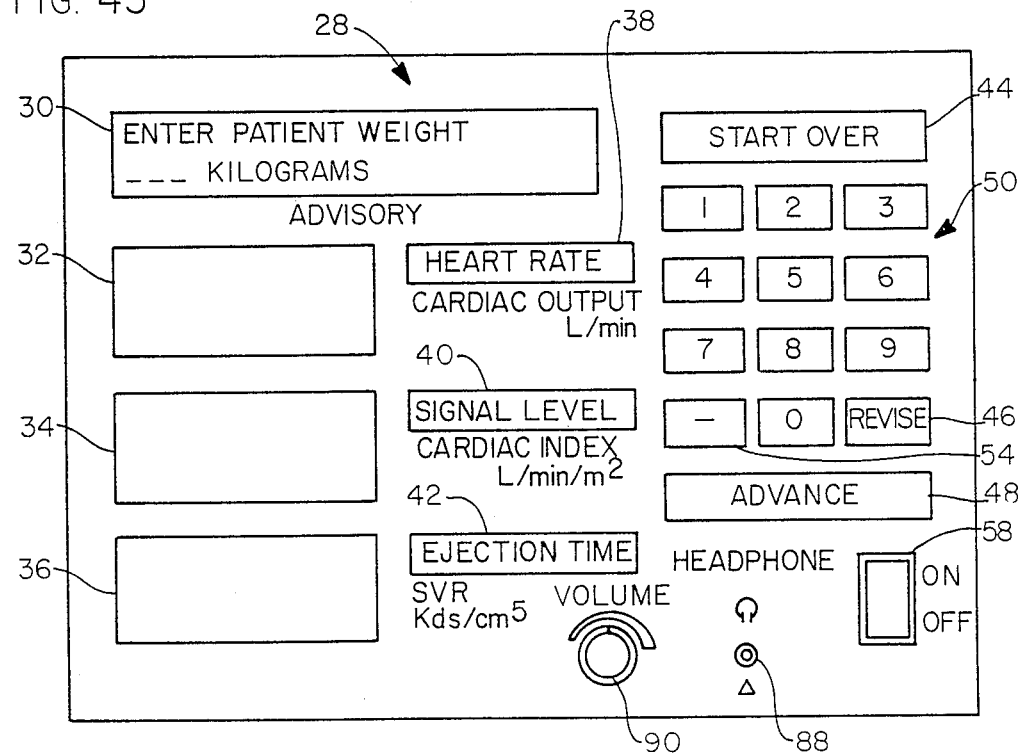
Figure 44:
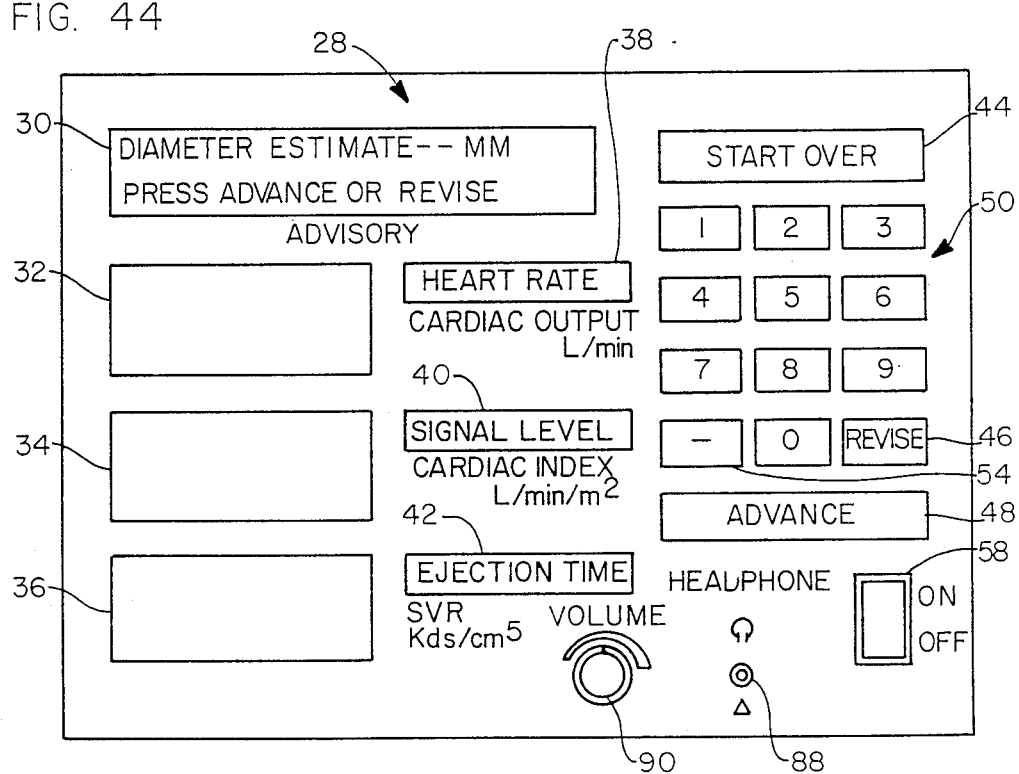
Figure 45:
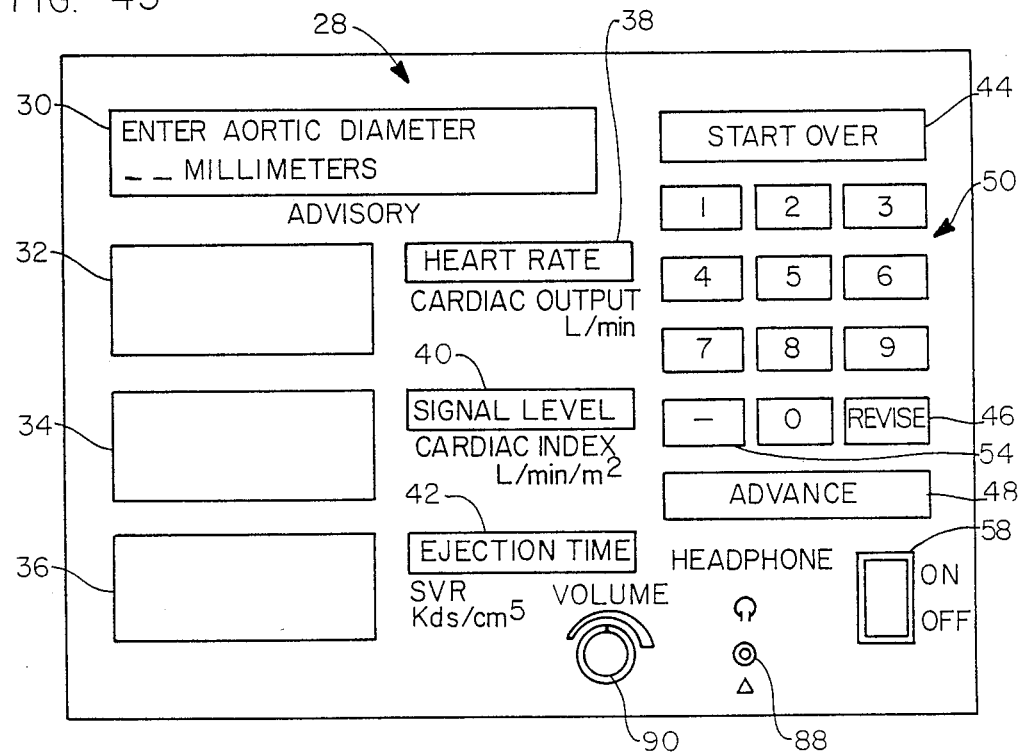

The patient's weight is entered from keyboard 50, and it may be entered in either pounds (FIG. 42) or in kilograms (FIG. 43). Again the cardiac monitor is capable of discriminating between English and metric system entries without input from the operator.

No more than three weight indicating digits can be entered. These are displayed in advisory 30, again allowing the operator to confirm that his entry was properly made.

After the patient's weight is entered, the operator presses ADVANCE key 48 to proceed. At this point, the message DIAMETER ESTIMATE appears (see FIG. 44) along with the aortic diameter calculated in cardiac monitor 18 from the patient's height, weight, age and sex. If the displayed aortic diameter appears credible, the operator can press key 48 and advance to the next step in the sequence. If the information appears inaccurate, the operator presses REVISE key 46 which, in this case, brings up AORTIC DIAMETER SOURCE (see FIG. 36). This allows the patient's aortic diameter to be recalculated or replaced with an otherwise obtained aortic diameter measurement.

If the operator pushes key 2 (known aortic diameter) instead of key 1 in response to the AORTIC DIAMETER SOURCE (FIG. 36), the prompt ENTER AORTIC DIAMETER (FIG. 45) appears instead of ENTER PATIENT SEX (FIG. 37). The operator responds to the prompt depicted in FIG. 45 by depressing the appropriate keys 1 through 0 to enter the patient's known aortic diameter in millimeters.

Figure 46:
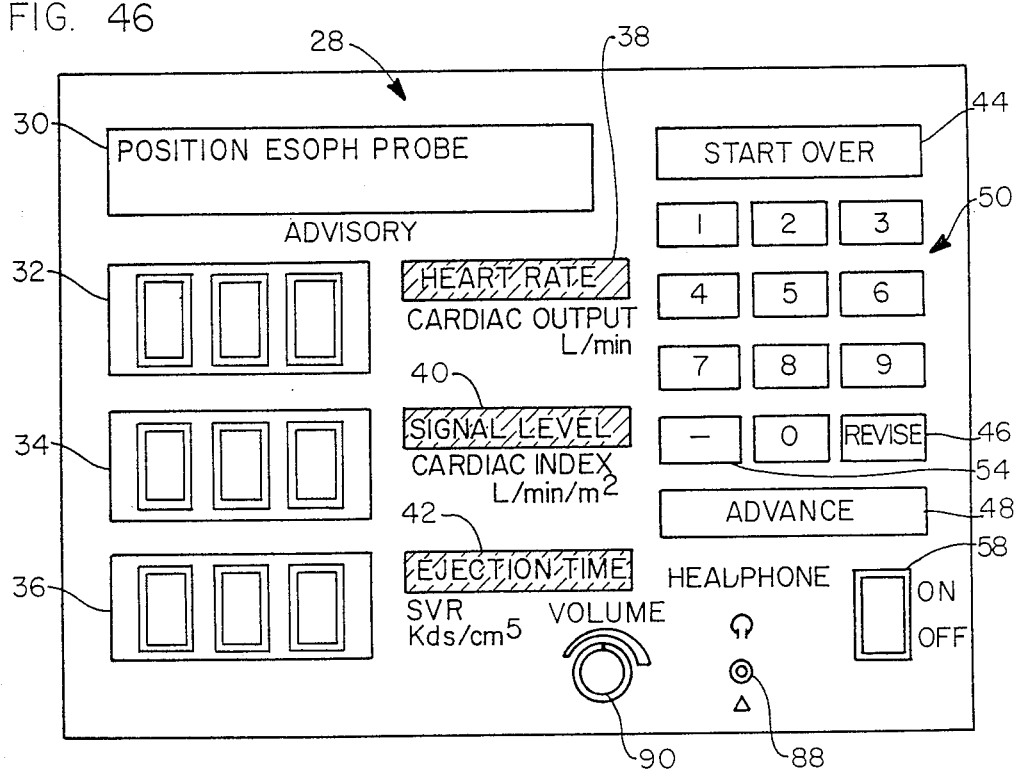

Once the patient's aortic diameter has been calculated or entered, the operator presses ADVANCE key 48, bringing up the instruction POSITION ESOPH PROBE (see FIG. 46).

At this point, the blacklighted LED displays, 38, 40, and 42 designated HEART RATE, SIGNAL LEVEL, and EJECTION TIME are illuminated.

The operator now introduces esophageal probe 220 into the patient's mouth and floats it downwardly through his or her esophagus in the same manner as an esophageal stethoscope. This is most easily accomplished with the patient in the supine position. A white stripe running down the probe (not shown) indicates the positions of the probe's transducer 236. The probe is inserted so that this stripe points posteriorly and slightly to the left when the probe is inserted. Generally, the probe is inserted as far as possible (40-45 cm) and then pulled out until it is inserted to a depth of 30-40 cm (typical for a normal adult).

After insertion, probe 220 is aimed by changing the depth of insertion and by rotating the probe until transducer 236 is aimed at the center of the patient's descending aorta 264.

As discussed above, esophageal probe 220 is properly positioned when transducer 236 is aimed at the center of descending aorta 264, and this happens when the signal visually displayed by LED 38 or heard through speaker 470 (FIG. 12G) or earphones plugged into jack 88 (FIG. 17) is at its maximum. This signal is related to the gain applied to amplifier 404 (see FIG. 12B) by the equation SIGNAL LEVEL$=100-10V_{AGC}$ where $V_{AGC}$ is the gain applied to amplifier 404. SIGNAL LEVEL rather than $V_{AGC}$ is employed in the aiming of esophageal probe 220 as an operator as is apt to be more accustomed to associating a high reading with proper positioning than a low reading.

The foregoing equation is solved by an elementary and conventional inverter/adder circuit shown in block diagram form in FIG. 12A and identified by reference character 499.

Figure 15:
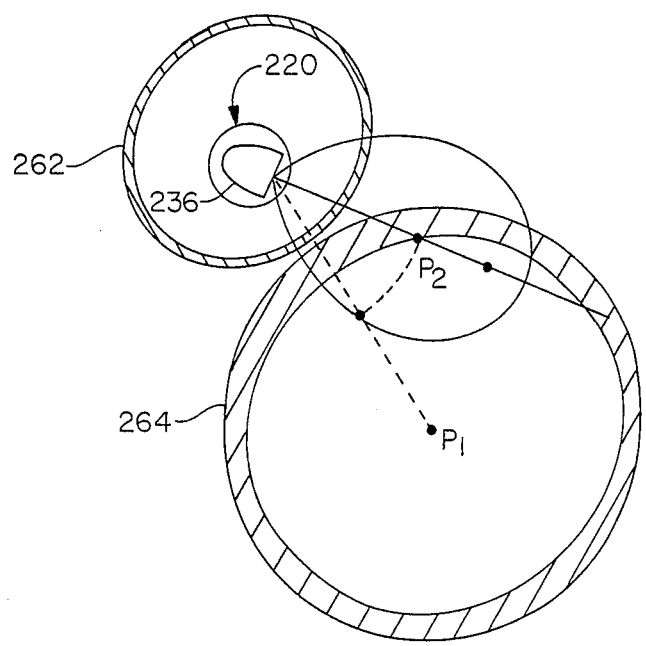
FIG. 15 shows the same probe incorrectly aimed by virtue of the esophageal probe transducer output signal strength having been used to aim the probe as has heretofore been done.

Heretofore, the signal utilized in aiming an esophageal probe of the type of concern at a patient's aorta was derived from the signal outputted from the transducer of the probe; and the probe was considered to be accurately aimed when this signal—proportional to the peak velocity of the blood flowing through the aorta—reached a maximum. We have discovered that this can result in an inaccurately aimed—i.e., offcenter—probe (see FIG. 15). This is because, as shown in FIG. 15 and also in FIG. 16, the peak velocity $P_2$ of the blood flowing through a patient's aorta may, and often is, not found at, or even close to, the center of the patient's aorta.

Figure 16:
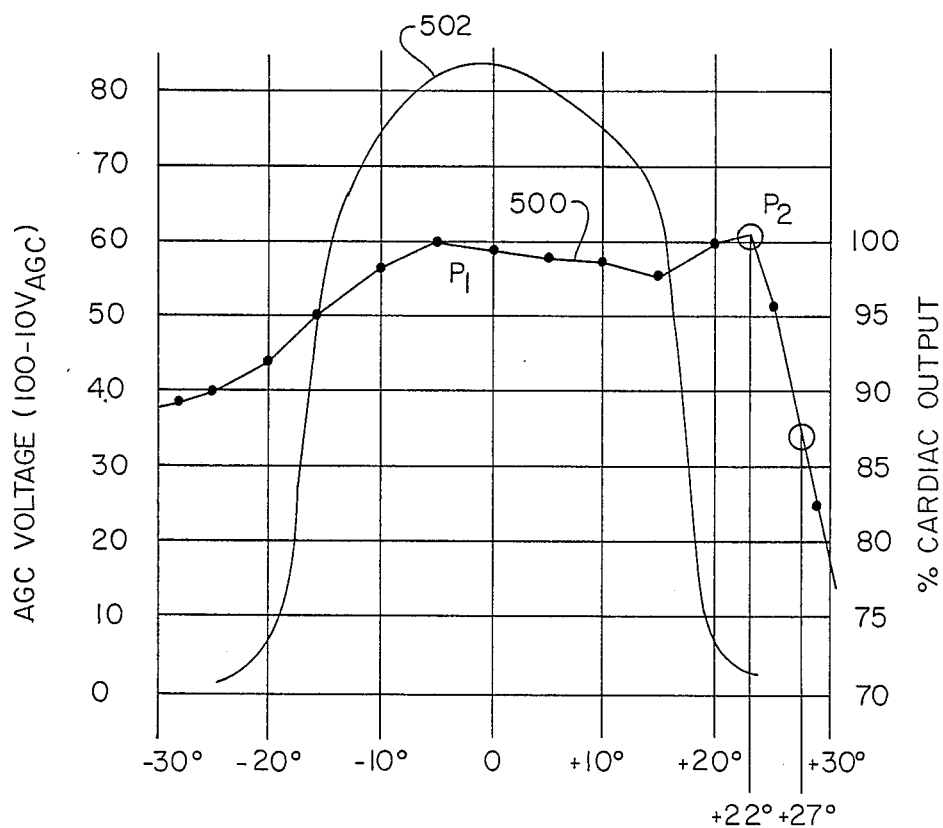
FIG. 16 shows, graphically, a typical relation between the transducer output signal strength and the level of gain in the receiver across the span of a patient's aorta.

In the representative example depicted in FIG. 16, for instance, a transducer aimed by a peak voltage signal would have been 22° off center; and a 5° misalignment (to 27° off center) would have resulted in a cardiac output reading almost 15 percent in error as is clear from the curve 500 representing cardiac output. Furthermore, it is the velocity at the center of the aorta ($P_1$ in FIGS. 5 and 16) which most accurately represents cardiac output, whether or not that velocity is the peak velocity of the blood flowing through the vessel at which the ultrasonic transducer is aimed. For this further reason, it is important that the ultrasonic probe be aimed at the center of the patient's aorta.

Figure 14:
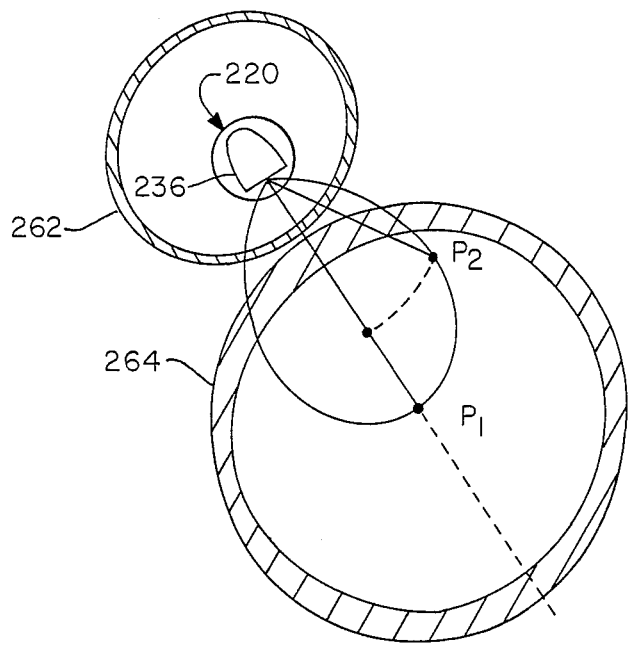
FIG. 14 depicts an esophageal probe as shown in FIG. 8 correctly aimed at the center of the patient's descending aorta by employing the level of the gain in the receiver of FIG. 12 to aim the probe.

Referring now to FIGS. 14 and 16, curve 502 represents the gain-related SIGNAL LEVEL. We have found and confirmed that this gain: (1) is independent of peak blood flow velocity $P_2$, (2) is accurately proportional to the velocity most accurately reflecting cardiac output, and (3) lowest when the frequency-shifted signal generating ultrasonic transducer 236 of esophageal probe 220 is aimed at the center of the descending aorta 264 or other blood vessel being monitored. As a consequence, SIGNAL LEVEL can be employed to unexpected advantage in aiming an ultrasonic transducer at a patient's aorta because that parameter is at a corresponding maximum when the transducer is aimed at the center of the patient's aorta.

Furthermore, only a slight rotation of the ultrasonic transducer 236 to each side of the aortic centerline results in a sharp drop off of SIGNAL LEVEL. Consequently, changes in this level associated with a slight rotation are easily detected, making accurate aiming easy to accomplish.

This is not true of the prior art, peak velocity-related aiming techniques. FIG. 16 shows that the blood flow velocity profile may typically not have a significant variation over as much as half of the span of the aorta being monitored. Thus, in the representative, FIG. 16 example, ultrasonic transducer 236 may be misaligned as much as $-10$, $+20°$ without there being any useful indication of the misalignment.

In employing our novel technique for aligning an ultrasonic transducer, esophageal probe 220 can be rotated until the gain-related signal is maximized. Alternatively, we have found that merely confirming that the visually and/or audibly presented SIGNAL LEVEL is above an appropriate threshold will insure that the probe is aimed with an acceptable degree of accuracy.

Thus, cardiac monitoring apparatus 18 may be programmed to present the advisory POSITION OK .... WAIT shown in FIG. 46A if SIGNAL LEVEL is at on above the retested threshold and the advisory OPT. SL THEN ADVANCE shown in FIG. 46B if the signal is below that level but strong enough to use in making a usable cardiac output calculation.

Figure 46A:
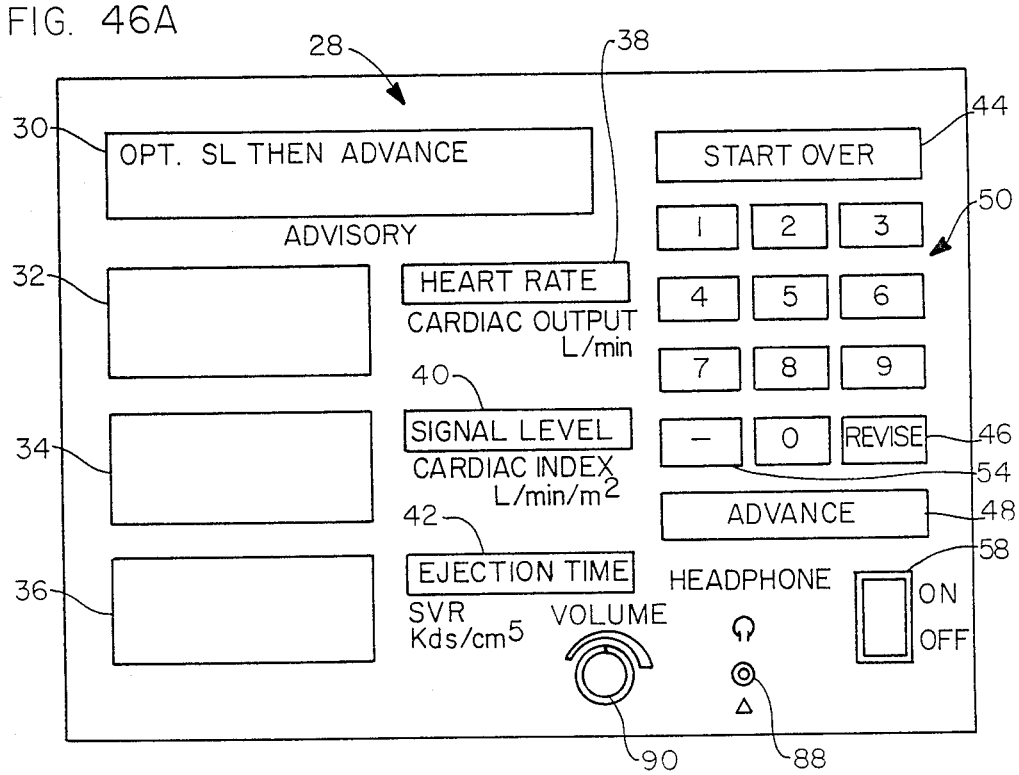

If the advisory shown in FIG. 46A appears, the monitoring apparatus will automatically advance to the next stage of operation. If the signal is below threshold level and the FIG. 46B advisory appears instead, the operator rotates esophageal probe 220 until satisfied that it is optimally positioned and then presses ADVANCE key 48.

Figure 47:
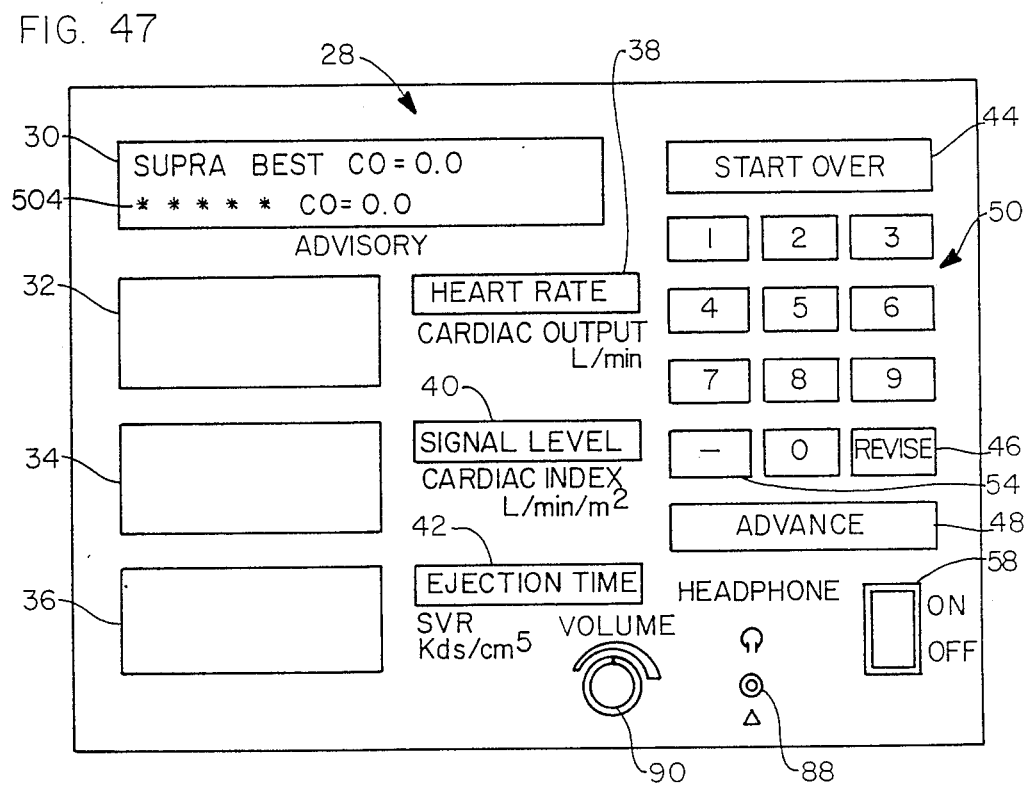

In both of the foregoing situations, the prompt shown in FIG. 47 will appear if the suprasternal notch probe method of calibration (FIG. 31) is employed. In response, the operator employs suprasternal notch probe 326 to measure the velocity of the blood flowing through the patient's ascending aorta in the manner discussed above in conjunction with FIGS. 2-7. Cardiac monitoring apparatus 18 uses this measured value to convert the velocity measured by esophageal probe 220 to a value indicative of the velocity of the blood flowing through the patient's ascending aorta 266.

As is shown in FIG. 47, two advisories are displayed during the aiming of supraternal notch probe 326. One (CO) is the current cardiac output, which may change as the probe is manipulated. The other (BESTCO) is the best output theretofore obtained in positioning the probe. Aiming is typically taken as completed and accurate when a value higher than BESTCO can not be obtained.

Figure 48:
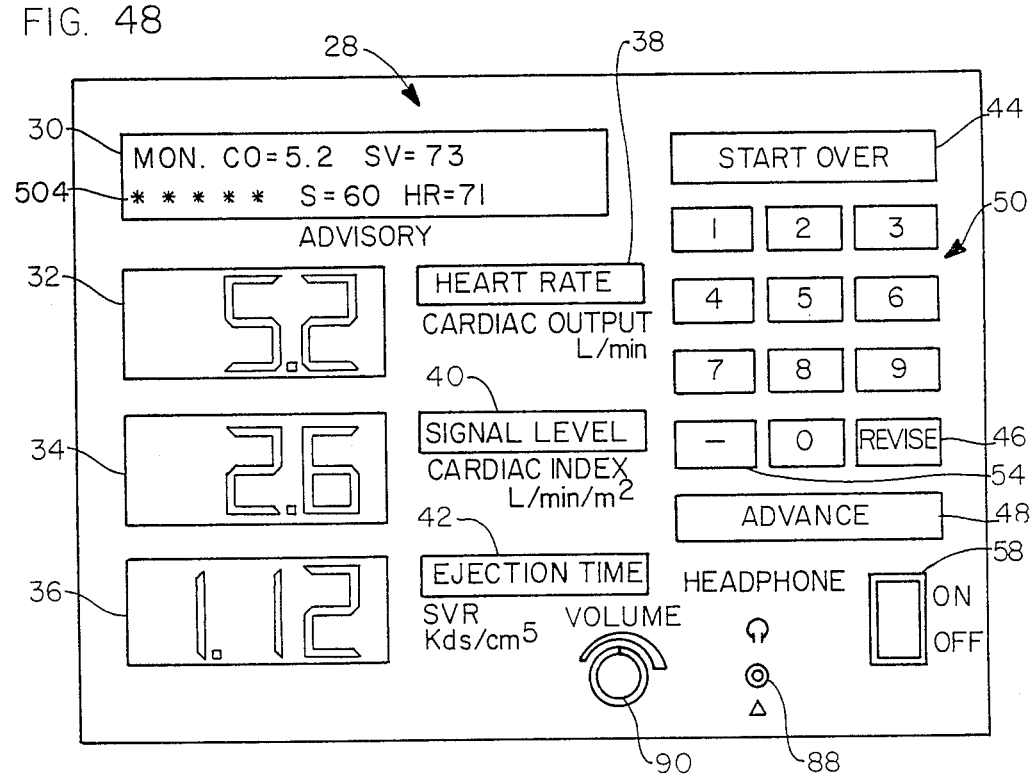
Figure 49:
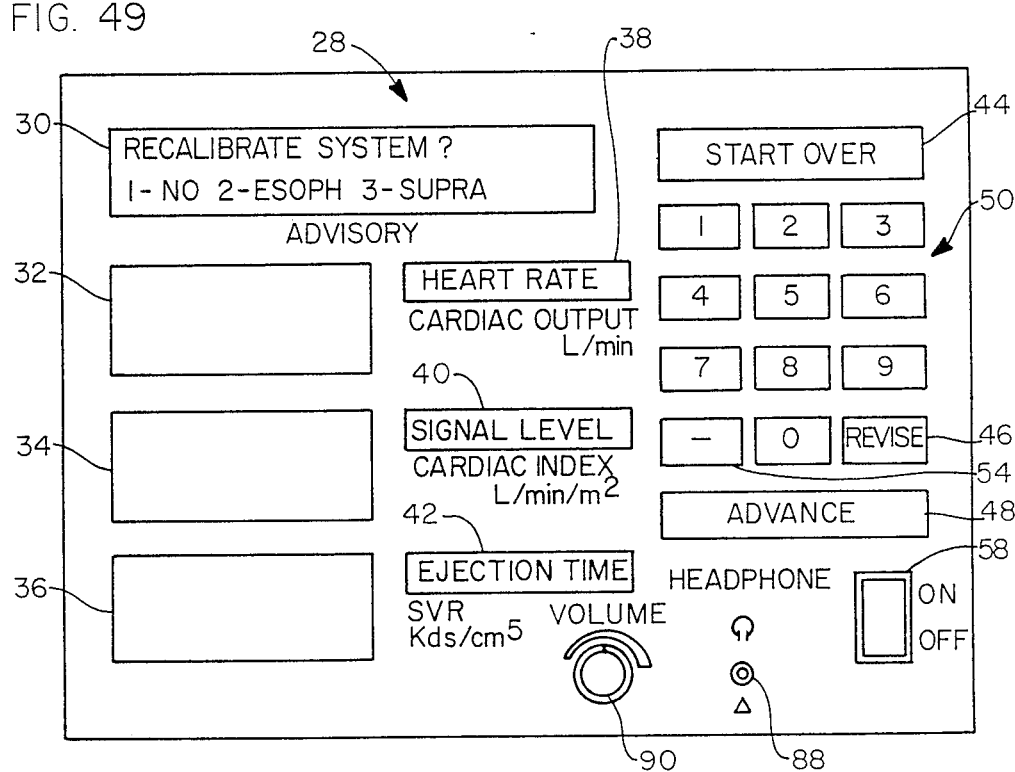
Figure 50:
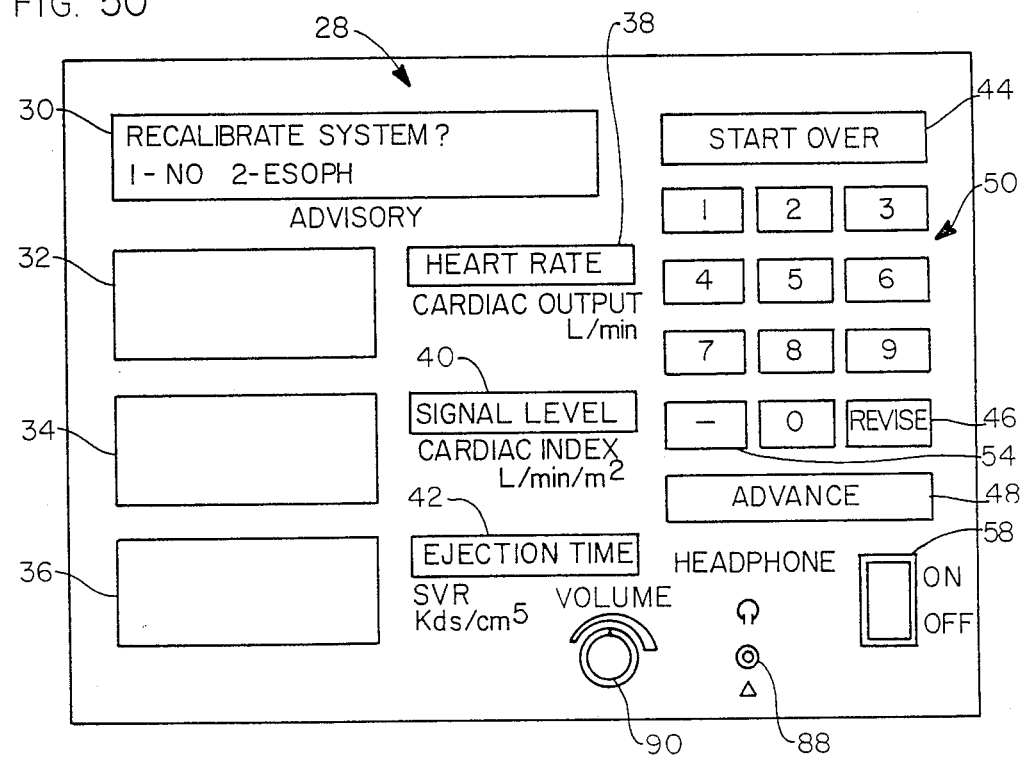
Figure 51:
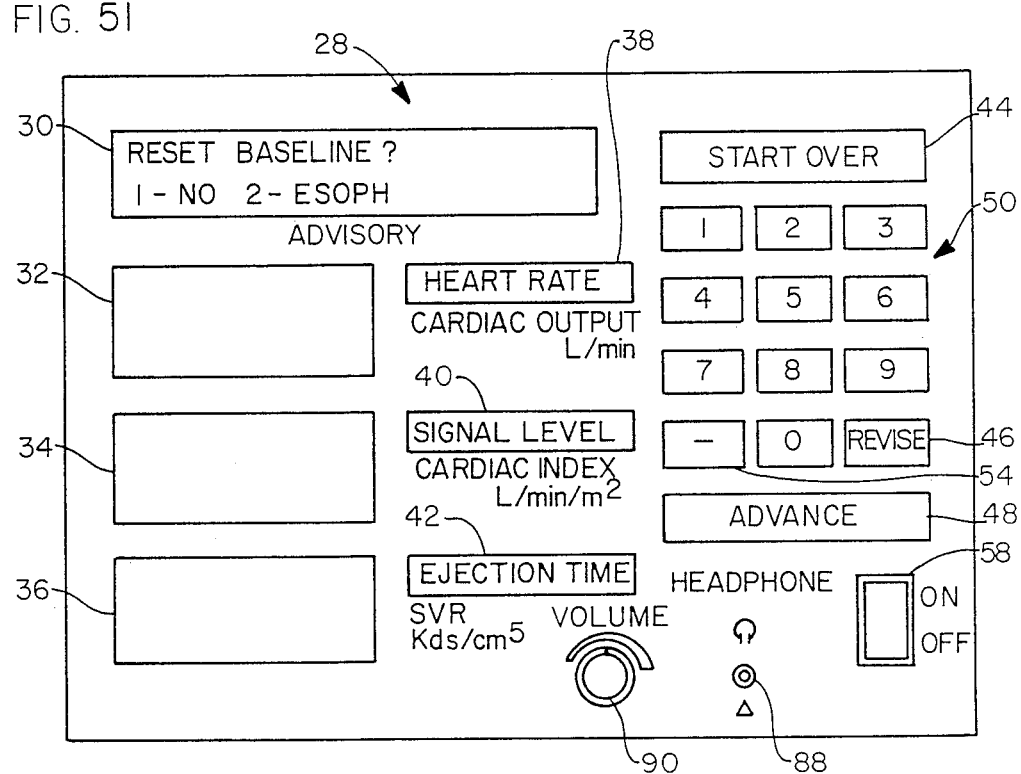

At this point, cardiac monitoring apparatus 18 switches to its monitoring mode. Representative values that may appear on monitor 28 are illustrated in FIG. 48. The cardiac output, cardiac index, and systemic vascular resistance values displayed in LED readouts 32, 34, and 36 are updated every 15 seconds unless cardiac output changes by $\pm 10\%$ or more. If this occurs, the information displayed in readouts 32, 34, and 36 is updated immediately.

As shown in FIG. 48, SIGNAL LEVEL is continuously displayed (at S) while cardiac monitoring apparatus 18 is in its monitoring mode. This is an important feature of the apparatus as a significant change in the value displayed will indicate to the operator that something is amiss; for instance, that esophageal probe 220 has shifted—in the course of moving the patient or movement on his or her own part, for example—and needs to be repositioned.

When percentage trending is selected as the calibration method, the trending percentages will be shown in LED displays 32, 34, and 36 of monitor 28. Advisory 30 will show percent stroke volume, cardiac output, and heart rate.

Cardiac monitoring apparatus 18 may be recalibrated at any time while it is in the monitoring mode. To accomplish this, REVISE key 46 is pressed, causing the prompt shown in FIG. 49 to appear. Three choices are then available. If key 1 on keyboard 50 is depressed to elect the first of these options, apparatus 18 is returned to the monitoring mode. If option two is selected, the prompt POSITION ESOPH PROBE (FIG. 46) will appear; and, if the third option is exercised by depressing key 3, the operator is returned to the step of suprasternal calibration; and the prompt shown in FIG. 47 appears.

Recalibration can also be effected if apparatus 18 is monitoring with a known cardiac output or percent trending is being employed. In this case, the prompt shown in FIG. 50 will appear. Two options are available. If the first is selected by depressing key 1, apparatus 18 will return to its monitoring mode. If the second option is selected, the operator is returned to the prompt (FIG. 46B) for reaiming esophageal probe 220.

Also, as will be apparent to the reader from the foregoing portion of this detailed description, any of the previously discussed prompts can be accessed by repeatedly pressing REVISE key 46 until the wanted prompt is reached.

Another option that is available is recalibration of apparatus 18 during trending. If REVISE key 46 is pressed while apparatus 18 is operating in that mode, the advisory shown in FIG. 51 will appear on monitor 28. If key 1 is then depressed, it will flash to indicate that the default selection has been made. Pressing ADVANCE key 48 will then select option NO and return system 18 to normal trending without recalibration.

Figure 52:
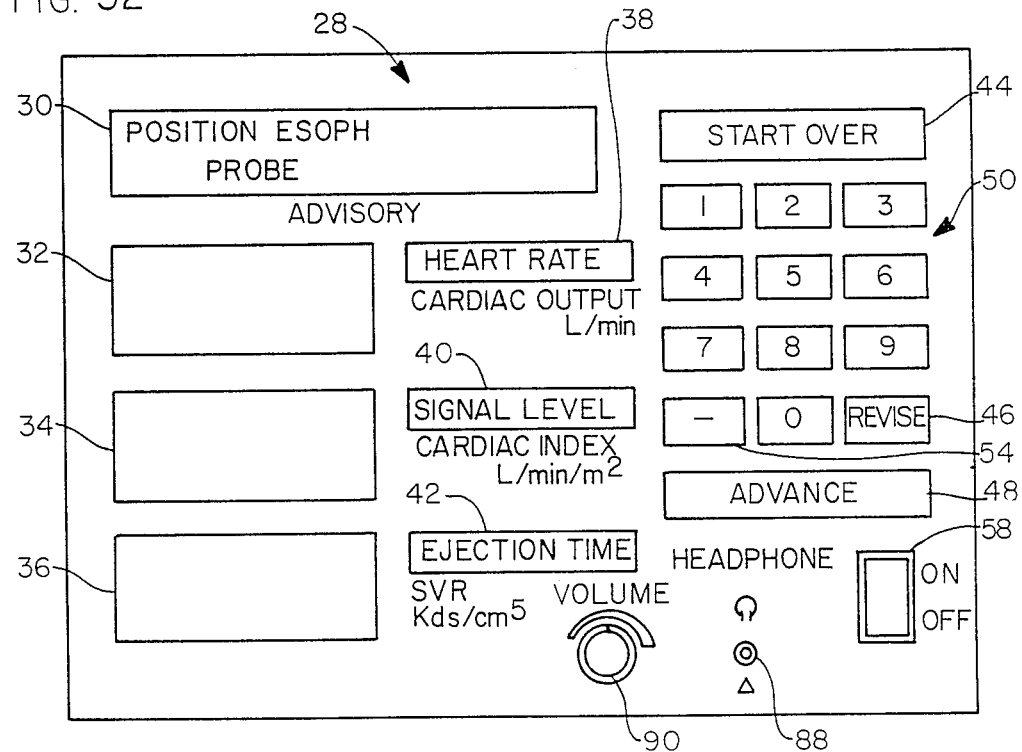

To reset the percentage baseline for trending, first key 2 and then ADVANCE key 48 are pressed, causing the prompt shown in FIG. 52 to appear. Esophageal probe 220 is then positioned as discussed above with the apparatus advancing to monitoring automatically (or when ADVANCE key 48 is pressed after the signal outputted by esophageal probe 220 has been optimized). Apparatus 18 will then begin trending at 100%, displaying cardiac output as a percentage of the new baseline.

Figure 52A:
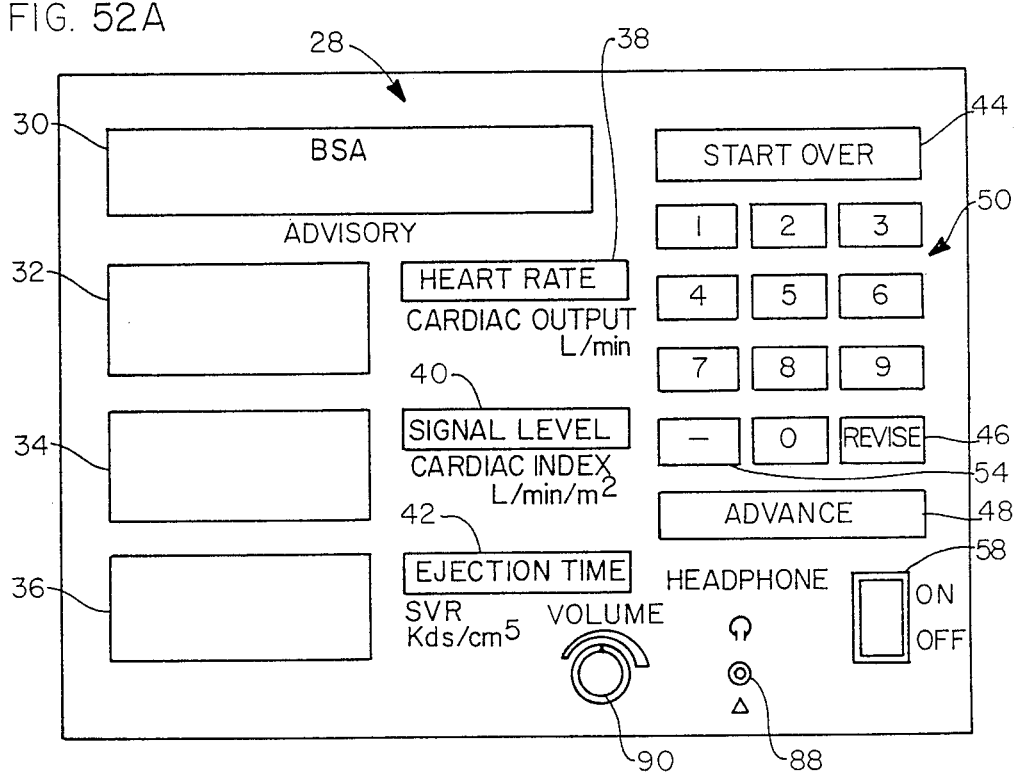
Figure 53:
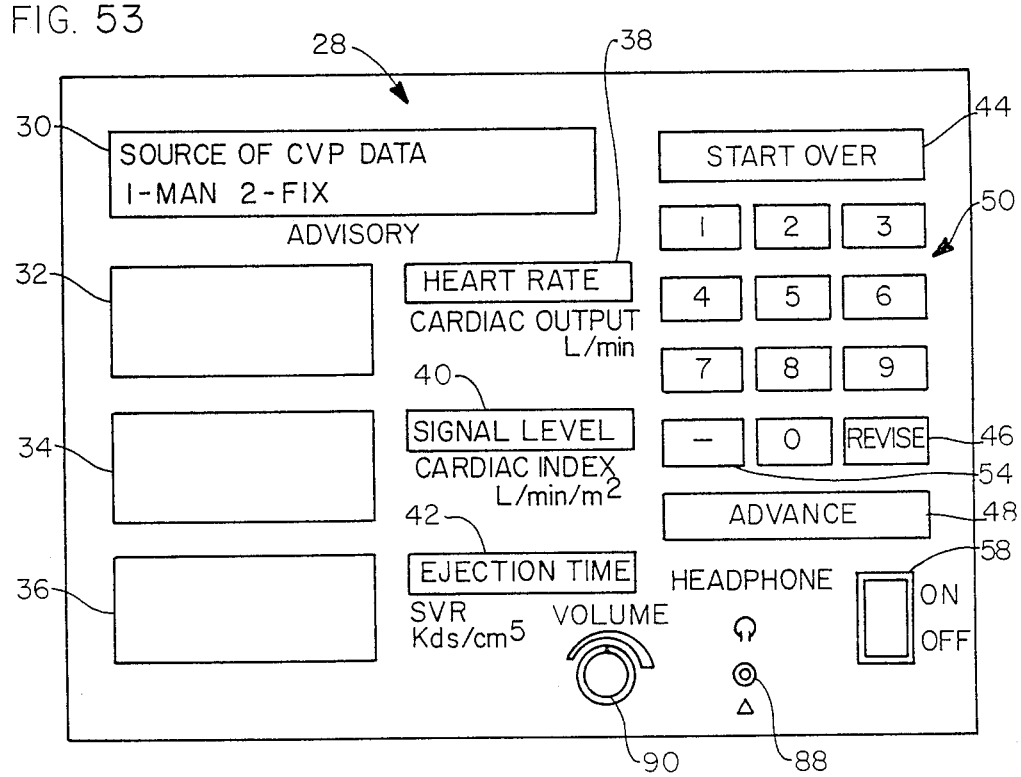
Figure 54:
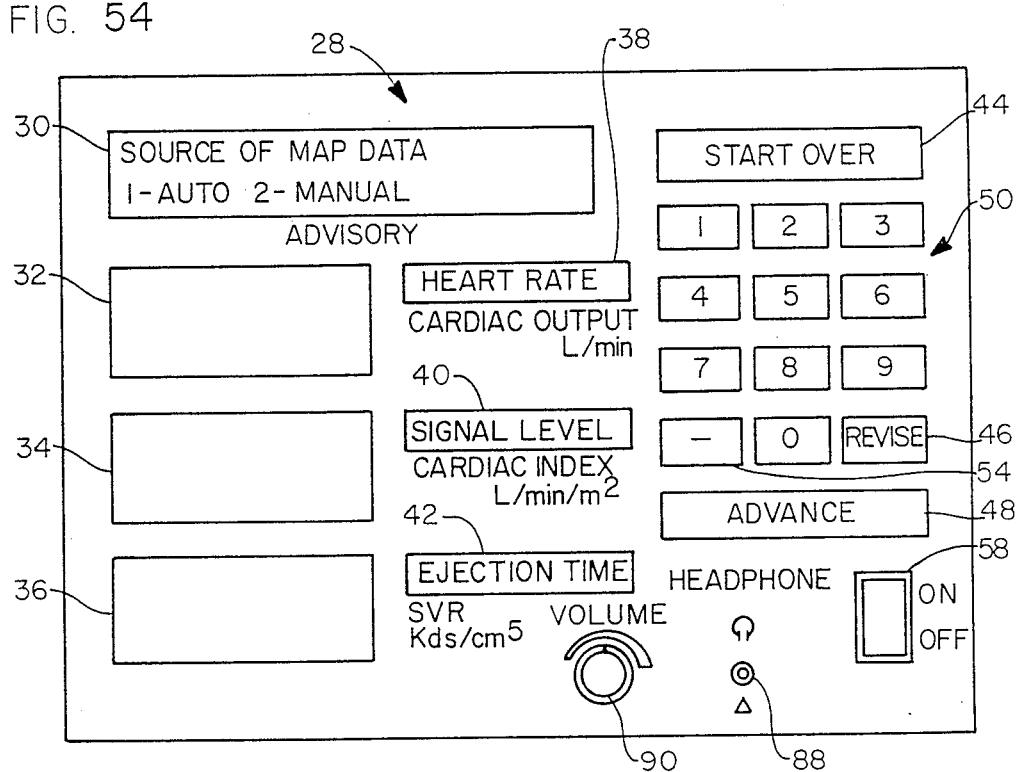

We pointed out above that cardiac monitoring apparatus 18 can be set up to display the patient's cardiac index and/or vascular resistance in addition to his or her cardiac output. If cardiac index is selected (see FIGS. 23, 24, and 27), it becomes necessary to take the patient's body surface area into account in the above-described sequence employed to ready apparatus 18 for monitoring. An appropriate prompt (shown in FIG. 52A) in this case appears at the appropriate point in the the sequence (after aortic diameter is accepted), and the operator presses ADVANCE key 48 to cause apparatus 18 to calculate the patient's body surface area from the previously entered height and weight.

If cardiac output is entered directly, the following steps are also required:

I. after entering aortic diameter or cardiac output and pressing ADVANCE key 48, the operator is prompted to enter the patient's height. He enters the height and presses ADVANCE key 48;

II. At the prompt for entering the patient's weight, the operator enters the weight and presses ADVANCE key 48. The calculated body surface area (BSA) is displayed on monitor 28. The operator presses ADVANCE key 48 to accept or REVISE key 44 to have the body surface area recalculated.

If the operator has elected to have systemic vascular resistance monitored (FIGS. 23, 25, and 26), he is prompted and instructed as follows though in a more abbreviated format:

I. If you have not selected SVR, you will then be prompted to position the esophageal probe 220 (see FIG. 46).

II. If you have selected SVR, the prompt shown in FIG. 53 will appear after the aortic diameter has been entered or computed (the same prompt also appears after the body surface area is calculated for cardiac index).

III. For manual input of CVP, press key 1 and then ADVANCE key 48. Use the keypad 50 to enter the data manually. You will be prompted to enter a new value every 7 minutes. Press ADVANCE key 48 after entering the value.

IV. If you wish to override the 7 minute update for blood pressure, press key 2 for FIX. Now enter the value manually. FIX allows monitoring apparatus 18 to continue to calculate SVR using the CVP entered manually until you change the value or select the MAN option.

V. After establishing the input of CVP, cardiac monitoring apparatus 18 requires the mean arterial pressure (MAP). The prompt (shown in FIG. 54) appears after the CVP data is entered.

VI. If you have a blood pressure monitor connected to cardiac monitoring apparatus 18, press key 1 for automatic reading of MAP. Then press ADVANCE key 48. Cardiac monitoring apparatus 18 requires a blood pressure update at least every seven minutes or calculations of SVR will be terminated.

VII. If you don't have a monitor attached, press key 2 and enter the data using the keypad manual input of MAP. You will be required to update the MAP value every 7 minutes. Press ADVANCE key 48.

Figure 55:
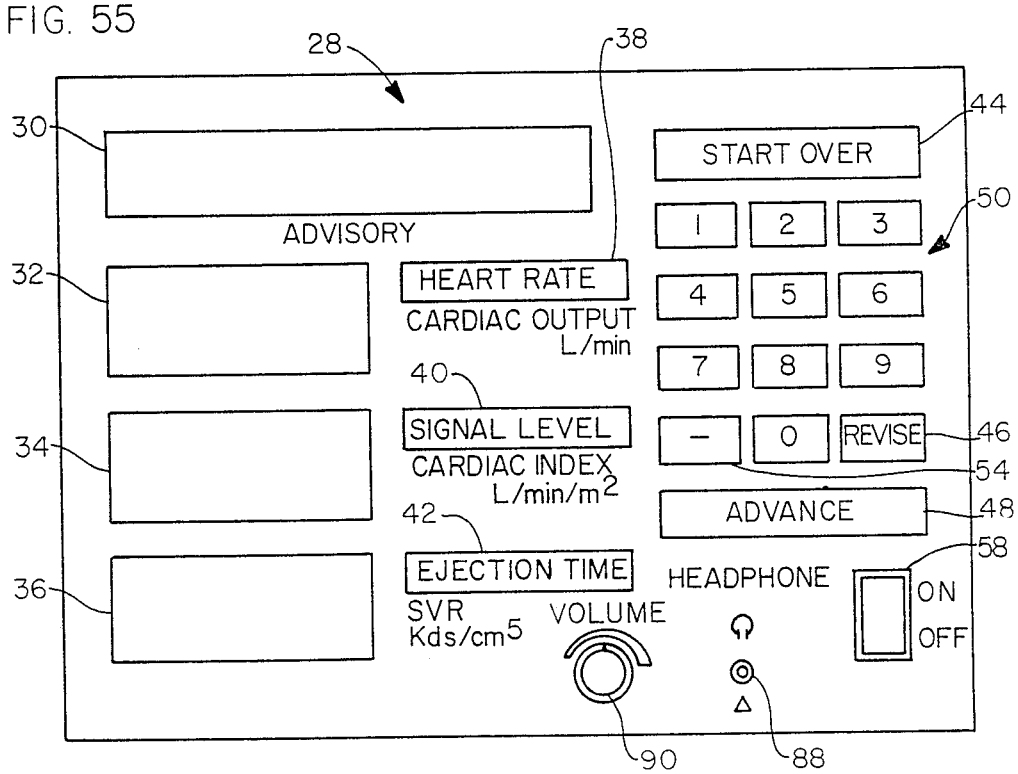

If the blood pressure value is not updated in the specified 7 minutes, the advisory shown in FIG. 55 appears. Permitted operator responses are: (a) pressing key 1 and entering the new information, and (b) pressing key 2 to cancel the SVR measurement. Inaction by the operator will result in SVR automatically being cancelled.

For the sake of conveniences and because it is currently the most important application of our invention, the latter has been described in relation to the aiming of an ultrasonic transducer at a patient's descending aorta. Our invention is however of much broader application in that it can advantageously be used to accurately aim an ultrasonic transducer at any visually obscured vessel through which a liquid is flowing as long as automatic gain is employed in processing the transducer output signal and the level of gain is the lowest when the transducer is aimed at the center of the vessel. Therefore, the detailed description of our invention is not intended to limit the scope of coverage to which we consider ourselves entitled.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A method of accurately aiming a transducer with an ultrasonic transmitter and a receiver for reflected ultrasonic energy toward the center of a blood vessel of a patient, said method including the steps of:
   a. converting the output from the transducer receiver to an electrical signal representing the frequency shift between the ultrasonic energy emitted from the transmitter and the energy reflected to the receiver;
   b. amplifying said electrical signal to a constant level by adjusting the gain of the circuit means employed to amplify said signal; and
   c. adjusting the position of the probe until the gain of the circuit means reaches a minimum.

2. A method of aiming an ultrasonic probe as defined in claim 1 wherein the probe is inserted in the patient's esophagus and the transducer of the probe is aimed toward the patient's descending aorta.

3. A method of aiming an ultrasonic probe as defined in claim 1 in which the gain of said circuit means is visually and/or audibly presented to enable an operator to identify the level of the gain.

4. A method of aiming an ultrasonic transducer as defined in claim 1 in which the transducer is mounted on the distal end of an esophageal probe.

5. A method of accurately aiming the transducer of an ultrasonic probe inserted in a patient's esophagus toward the center of the patient's aorta, said method comprising the steps of:
   a. converting the transducer output to an electrical signal representing the shift in frequency between the ultrasonic energy emitted from said transducer and the ulstrasonic energy reflected from the blood flowing through the aorta at which the transducer is aimed.
   b. amplifying said electrical signal to a constant level by adjusting the gain of the circuit means by which the signal is amplified; and
   c. manipulating said probe until the gain of the circuit means is at a minimum.

6. A method of aiming the transducer of an ultrasonic esophageal probe as defined in claim 5 wherein the level of gain is visually and/or audibly presented to an operator to facilitate the positioning of said transducer.

7. A method for ascertaining the cardiac output of a human patient, said method comprising the steps of:
   a. measuring the systolic velocity of the blood flowing through the patient's descending aorta;
   b. determining the cross-sectional area of the patient's ascending aorta; and
   c. calculating the patient's cardiac output from said systolic velocity and said aortic area;
   d. the systolic velocity of the blood flowing through the patient's descending aorta being measured by:
      (i) inserting an ultrasonic transducer in the esophagus of the patient,
      (ii) aiming said transducer toward the descending aorta of the patient,
      (iii) emitting ultrasonic energy from the transducer toward said descending aorta,
      (iv) detecting frequency shifted ultrasonic energy reflected from the blood flowing through said aorta,
      (v) generating an electrical transducer output indicative of the frequency shift between the emitted and reflected ultrasonic energy,
      (vi) amplifying said signal and so adjusting the gain of the signal amplifying circuitry as to keep the level of said signal at a constant value, and
      (vii) and reorienting said transducer until the gain reaches a minimum;
   e. whereby said transducer will be aimed at the center of said aorta and a signal accurately reflective of the patient's cardiac output will be obtained when said gain is at said minimum.

8. A method of measuring cardiac output as defined in claim 7 wherein the circuit gain is visually and/or audibly presented to an operator to facilitate the positioning of the ultrasonic transducer.

9. A method of measuring cardiac output as defined in claim 7 in which the ultrasonic transducer is mounted on the distal end of an esophageal probe.

10. A method of measuring cardiac output as defined in claim 7 in which the systolic velocity of the blood flowing through the patient's descending aorta is scaled upwardly to the velocity of the blood flowing through his or her ascending aorta before the calculation of the patient's cardiac output is made.

11. A method of measuring cardiac output as defined in claim 10 wherein said systolic velocity is measured with an esophageal probe and wherein the systolic velocity of blood flowing through the patient's descending aorta is scaled upwardly to the velocity of the blood flowing through his or her ascending aorta before the calculation of the patient's cardiac output is made by measuring the systolic velocity of the blood flowing through patient's ascending aorta, computing a scaling factor from the aforesaid systolic velocity and the systolic velocity of the blood flowing through the patient's descending aorta, and employing said factor to scale the systolic velocity of the patient's systolic velocity as aforesaid.

12. A method of measuring cardiac output as defined in claim 11 wherein the velocity of the blood flowing through the patient's ascending aorta is measured with an ultrasonic suprasternal notch probe.

13. A method of measuring cardiac output as defined in claim 7 wherein said cardiac output is calculated by: generating a signal representative of the systolic velocity of the blood flowing through the patient's descending aorta; upwardly scaling that signal from a calibration signal representing the velocity of the blood flowing through the patient's ascending aorta; subjecting said first systolic velocity to frequency spectrum analysis to produce a multicomponent velocity profile signal; integrating said velocity profile signal with respect to time to thereby produce a systolic velocity integral; computing stroke volume as a function of said cross-sectional area and said systolic velocity integral; summing the stroke volumes thus determined for n beats of the patient's heart; and dividing the resulting sum by the time spanning said n beats.

14. A method of measuring cardiac output as defined in claim 7 wherein the patient's aortic area is predictively determined by solving the equation:

$$AD = C_1 + [C_2 \times AGE] \times [C_3 \times SEX] + [C_4 \times HEIGHT] + [C_5 \times WEIGHT] \quad (1)$$

where:
$C_1$ is in the range of 8.06 to 14.88,
$C_2$ is in the range of 0.055 to 0.077,
AGE is the age of the patient in years,
$C_3$ is in the range of $-2.43$ to $-1.57$,
SEX is 0 if the patient is a male and one if the patient is a female,
$C_4$ is in the range of 0.108 to 0.208,
HEIGHT is the height of the patient in inches,
$C_5$ is in the range of 0.010 to 0.018, and
WEIGHT is the weight of the patient in pounds.

15. A method of aiming an ultrasonic transducer as defined in claim 14 wherein the constants in Equation (1) are:
$C_1$: 11.47
$C_2$: 0.066
$C_3$: $-2.0$
$C_4$: 0.158
$C_5$: 0.014

16. A method of determining the cardiac index of a human patient which includes the steps of determining the cardiac output of the patient by the method defined in claim 7 and dividing the thus determined cardiac output of the patient by his or her body surface area.

17. A method for measuring the systemic vascular resistance of a human patient which comprises the steps of determining the cardiac output of the patient by the method defined in claim 7 and dividing a value representing the inverse of the systolic blood pressure of the patient by the thus determined cardiac output of the patient.

18. Apparatus for measuring the cardiac output of a human patient, said apparatus including: means including an ultrasonic transducer for measuring the systolic velocity of the blood flowing through the patient's aorta, means operatively connected to said measuring means for generating a constant amplitude electrical signal representative of said velocity, and means operatively connected to the signal generating means for calculating the cardiac output of the patient from the thus determined systolic flow velocity and the aortic diameter of the patient, said signal generating means comprising an amplifier and means for controlling the gain of said amplifier and said apparatus further including means for displaying a gain-related value that can be employed to aim said transducer toward the center of the patient's aorta and thereby make said measuring means capable of accurately measuring said systolic flow velocity.

19. Apparatus for measuring cardiac output as defined in claim 18 which includes means for calculating that value of the aortic diameter of the patient which is employed in computing the cardiac output of the patient, said means comprising data processing means for solving the equation:

$$AD = C_1 + [C_2 \times AGE] \times [C_3 \times SEX] + [C_4 \times HEIGHT] + [C_5 + WEIGHT] \qquad (1)$$

where:

$C_1$–$C_5$ are constants,

AGE is the age of the patient in years,

SEX is 0 if the patient is male and one if the patient is female,

HEIGHT is the height of the patient in inches, and

WEIGHT is the weight of the patient in pounds.

20. Apparatus for measuring cardiac output as defined in claim 19 wherein the constants in the equation which said data processing is enabled to solve are as follows:

$C_1$ is in the range of 8.06 to 14.88, $C_2$ is in the range of 0.055 to 0.077, AGE is the age of the patient in years, $C_3$ is in the range of $-2.43$ to $-1.57$, SEX is 0 if the patient is a male and one if the patient is a female, $C_4$ is in the range of 0.108 to 0.208, HEIGHT is the height of the patient in inches, $C_5$ is in the range of 0.010 to 0.018, and WEIGHT is the weight of the patient in pounds.

21. Apparatus for measuring cardiac output as defined in claim 20 wherein the constants in the equation which the data processing means is enabled to solve are:

$C_1$: 11.47

$C_2$: 0.066

$C_3$: $-2.0$ $C_4$: 0.158

$C_5$: 0.014

22. Apparatus for measuring cardiac output as defined in claim 18 wherein said transducer means is incorporated in means for generating a first signal representative of the systolic velocity of the blood flowing through the patient's descending aorta, the apparatus also including: means for upwardly scaling that signal to a second signal representing the velocity of the blood flowing through the patient's ascending aorta; means for performing a frequency spectrum analysis of said first signal to thereby produce a multicomponent velocity profile signal; means for integrating said multicomponent velocity profile signal with respect to time to thereby produce a systolic velocity integral; means for computing stroke volume as a function of said cross-sectional area and said systolic velocity integral; means for summing the stroke volumes thus determined for n beats of the patient's heart; and means for dividing the results by the time spanning said n beats.

23. Apparatus for measuring cardiac output as defined in claim 22 which includes an ultrasonic suprasternal notch probe for providing a one-time or calibration measurement of the systolic velocity of the blood flowing through the patient's ascending aorta and means for computing a scaling factor from the velocity and the systolic velocity.

24. Apparatus for measuring cardiac output as defined in claim 18 wherein said transducer means is incorporated in an esophageal probe.

25. Apparatus for measuring cardiac output as defined in claim 18 which includes a touch-sensitive display means via which an operator can interact with the apparatus in the course of measuring the patient's cardiac output, said display means including means for displaying instructions to said operator and information on the status of the apparatus and the patient's cardiac output.

26. Apparatus for measuring cardiac output as defined in claim 25 which includes a means for displaying information on the patient's cardiac index.

27. Apparatus for measuring cardiac output as defined in claim 18 which includes means for dividing said cardiac output of the patient by his body surface area and thereby obtaining the cardiac index of the patient.

28. Apparatus for measuring cardiac output as defined in claim 18 which includes means for dividing a value representing the blood pressure of the patient by the cardiac output of the patient and thereby obtaining his systemic vascular resistance.

29. Apparatus for measuring cardiac output as defined in claim 28 which includes means for displaying information on the patient's systemic vascular resistance.

30. Apparatus for measuring cardiac output as defined in claim 18 which includes a means for solving the equation $$SIGNAL\ LEVEL = 100 - 10 V_{AGC},$$

where:

SIGNAL LEVEL is the gain-related value, and $V_{AGC}$ is the gain applied to said amplifier.

* * * * *